(12) United States Patent
Colvin et al.

(10) Patent No.: US 11,491,250 B2
(45) Date of Patent: Nov. 8, 2022

(54) SYSTEMS AND METHODS FOR PROVIDING ULTRAVIOLET STERILIZATION, DISINFECTION AND DECONTAMINATION OF GAMING EQUIPMENT

(71) Applicant: Gaming Arts, LLC, Las Vegas, NV (US)

(72) Inventors: David Colvin, Las Vegas, NV (US); Eric D. Colvin, Las Vegas, NV (US)

(*) Notice: Subject to any disclaimer, the term of this patent is extended or adjusted under 35 U.S.C. 154(b) by 0 days.

(21) Appl. No.: 17/225,072

(22) Filed: Apr. 7, 2021

(65) Prior Publication Data

US 2021/0322595 A1    Oct. 21, 2021

Related U.S. Application Data

(63) Continuation-in-part of application No. 15/930,255, filed on May 12, 2020.

(60) Provisional application No. 63/199,182, filed on Dec. 11, 2020, provisional application No. 63/012,817, filed on Apr. 20, 2020.

(51) Int. Cl.
| | |
|---|---|
| *A61L 2/10* | (2006.01) |
| *A61L 2/24* | (2006.01) |
| *G07F 17/32* | (2006.01) |
| *A61L 2/26* | (2006.01) |

(52) U.S. Cl.
CPC .............. *A61L 2/10* (2013.01); *A61L 2/24* (2013.01); *A61L 2/26* (2013.01); *G07F 17/3216* (2013.01); *A61L 2202/11* (2013.01); *A61L 2202/14* (2013.01); *A61L 2202/15* (2013.01)

(58) Field of Classification Search
CPC .......... A61L 2/10; A61L 2/24; A61L 2202/11; G07F 17/3209; G07F 17/3216
See application file for complete search history.

(56) References Cited

U.S. PATENT DOCUMENTS

| | | | | |
|---|---|---|---|---|
| 7,975,908 B1* | 7/2011 | Greco | ................... | G07F 7/1091 |
| | | | | 235/379 |
| 2009/0252646 A1* | 10/2009 | Holden | ................... | A61L 2/202 |
| | | | | 422/24 |

* cited by examiner

*Primary Examiner* — Reginald A Renwick
(74) *Attorney, Agent, or Firm* — FisherBroyles, LLP; Rob L. Phillips

(57) ABSTRACT

Systems and methods for providing ultraviolet (UV) sterilization, disinfection and decontamination of electronic gaming machines (EGMs), gaming chips, dice, playing cards, currency, TITO tickets, etc. The ultraviolet sterilization, disinfection and decontamination may include a plurality of UV LEDs or RGB-UV LEDs of such wavelengths to be effective in reducing or eliminating viruses or the like. Pass through or planar arrays of UV or RGB-UV LEDs are mounted to or installed within a variety of gaming devices or equipment such as EGMs, chip trays, dice holders, automatic card shufflers, bill validators, magnetic card readers, currency counting or currency dispensing devices, printers, etc.

85 Claims, 44 Drawing Sheets

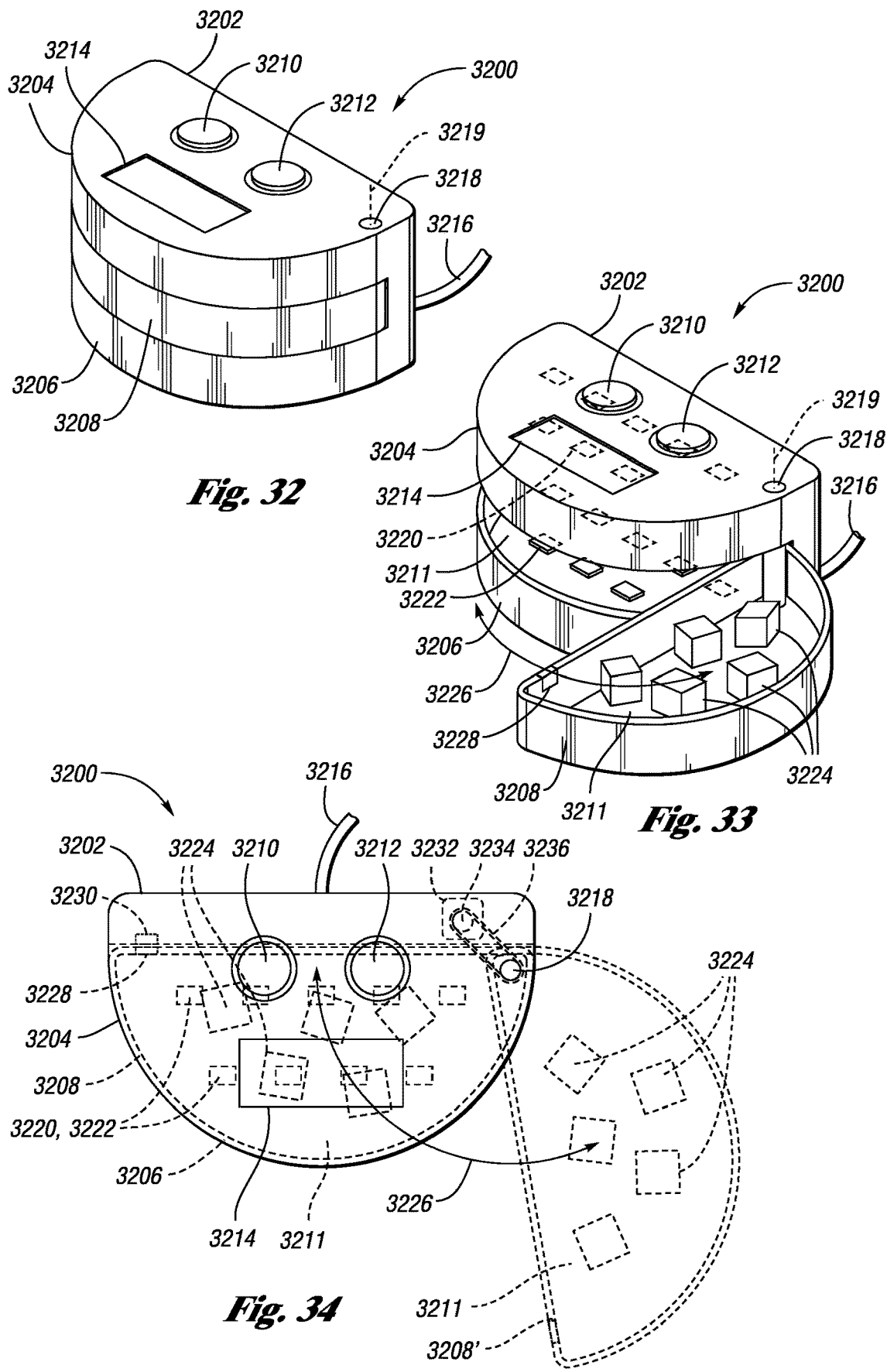

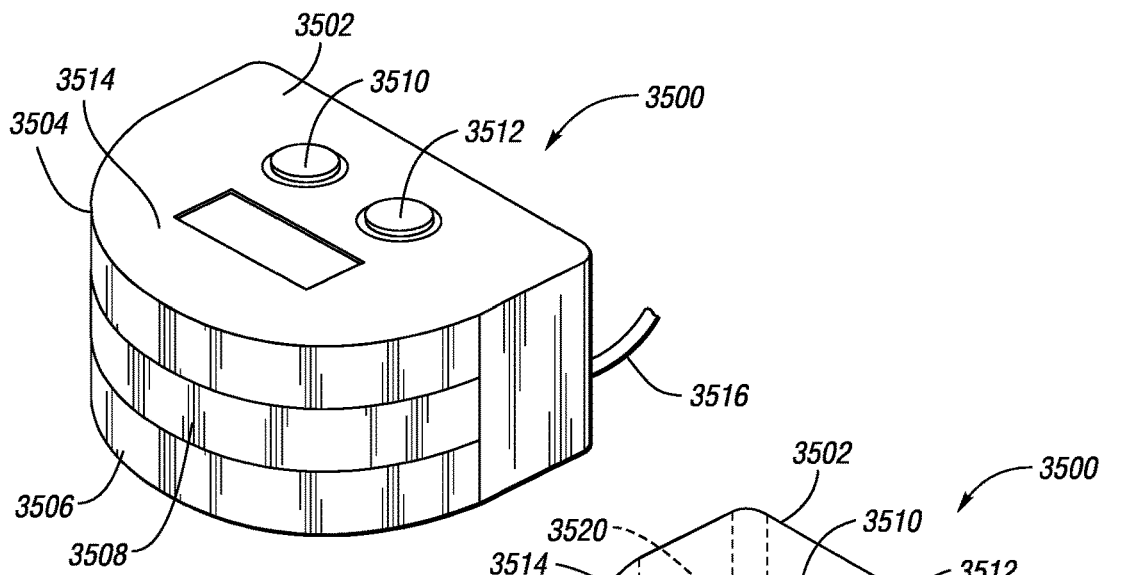
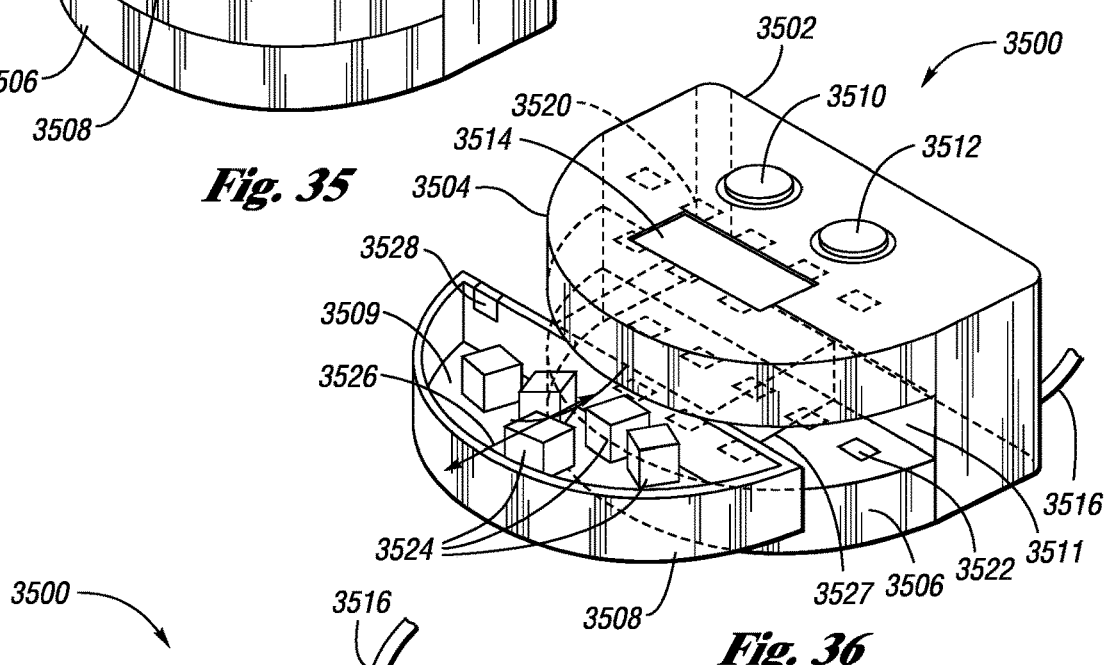
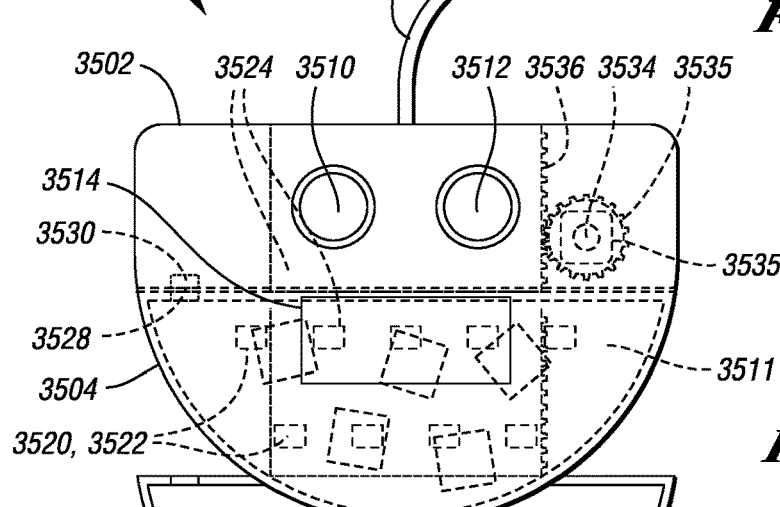
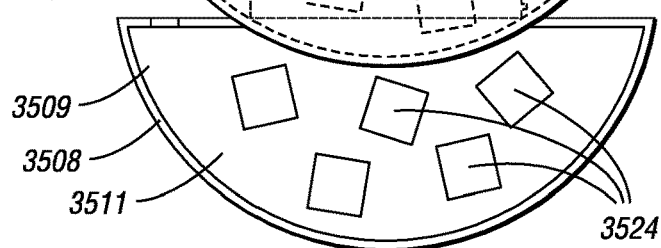

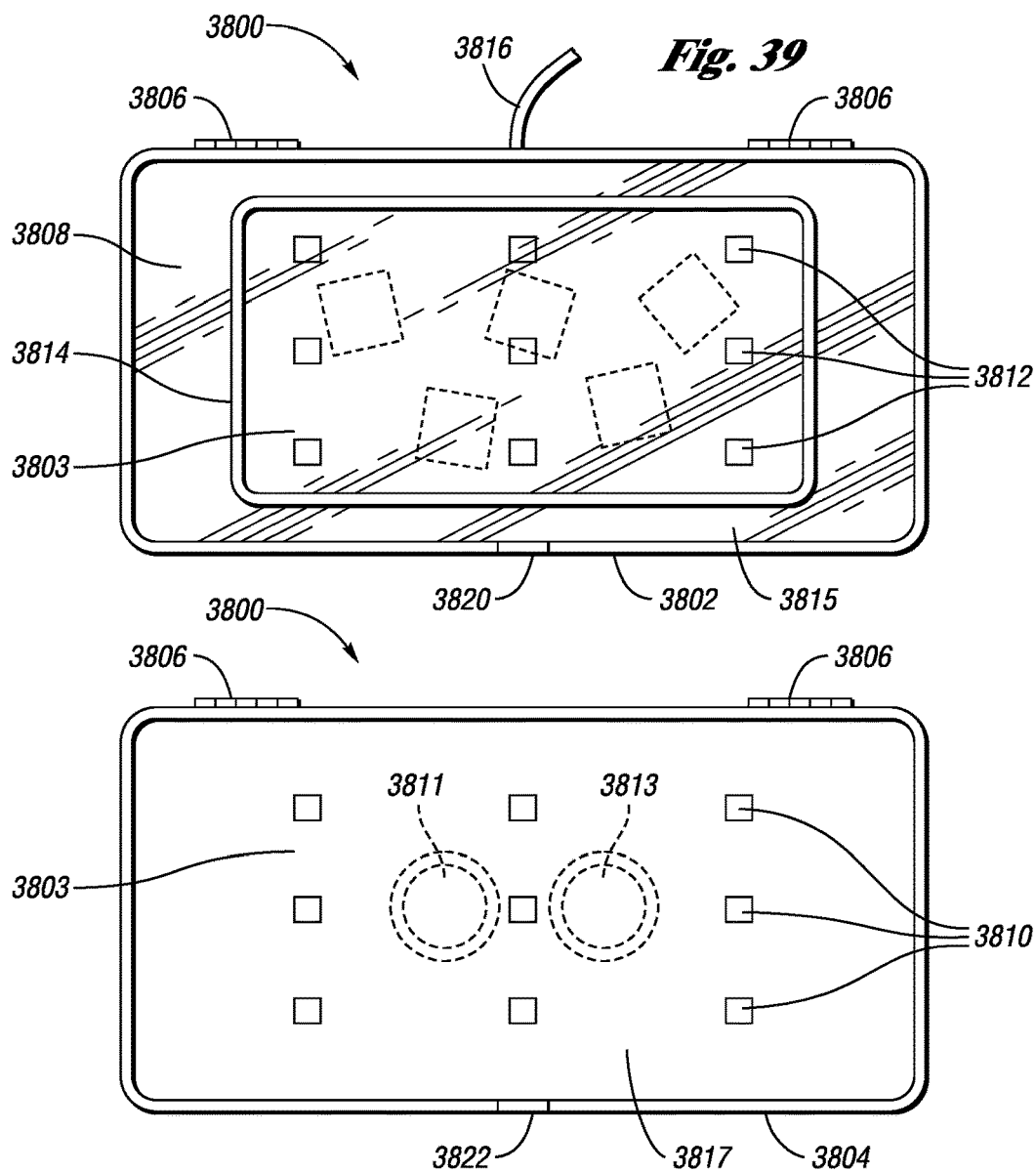
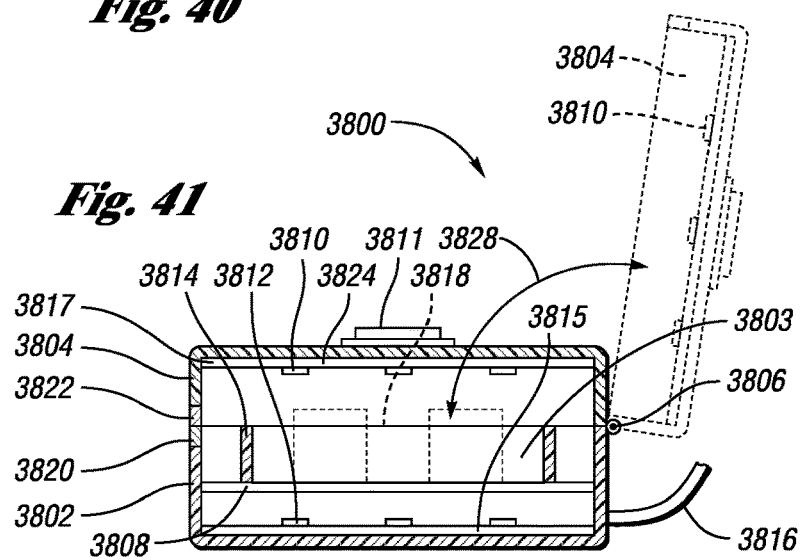

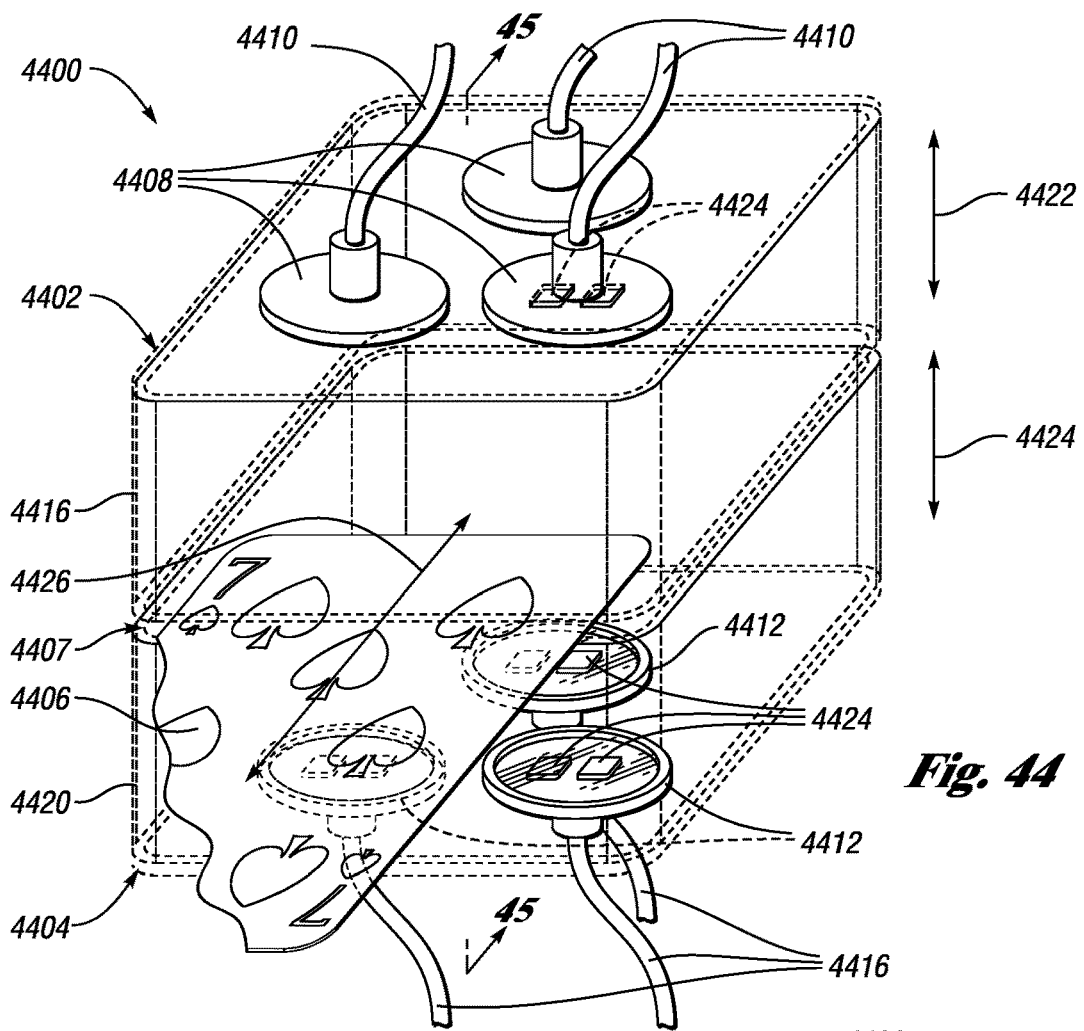
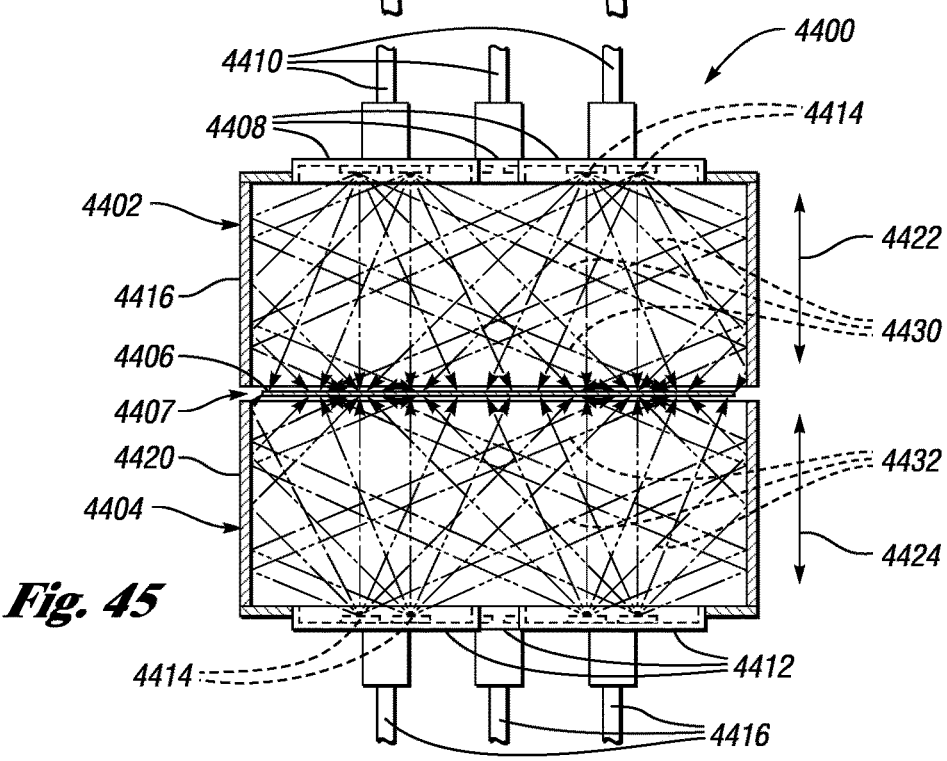

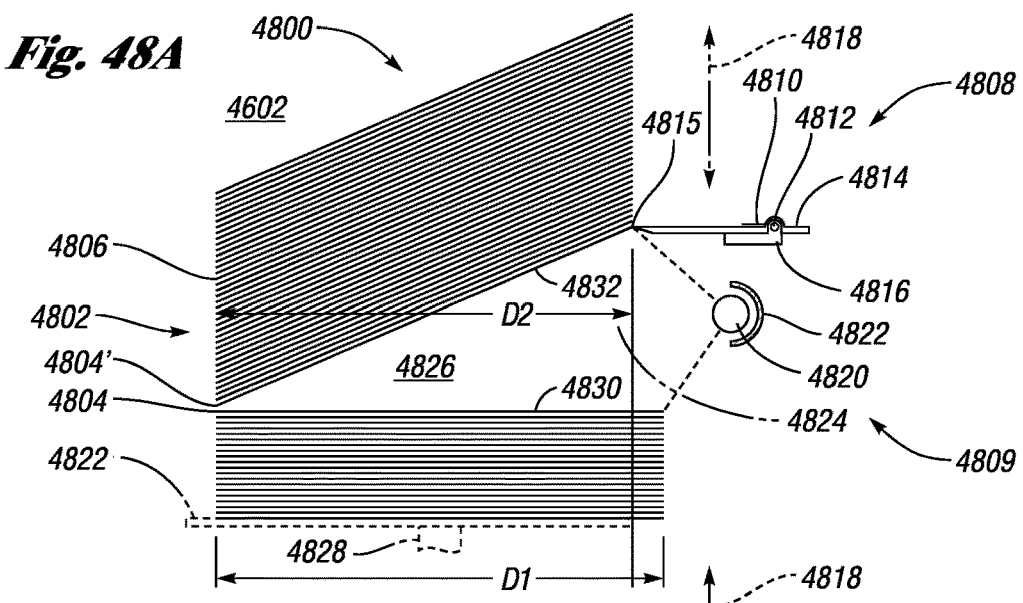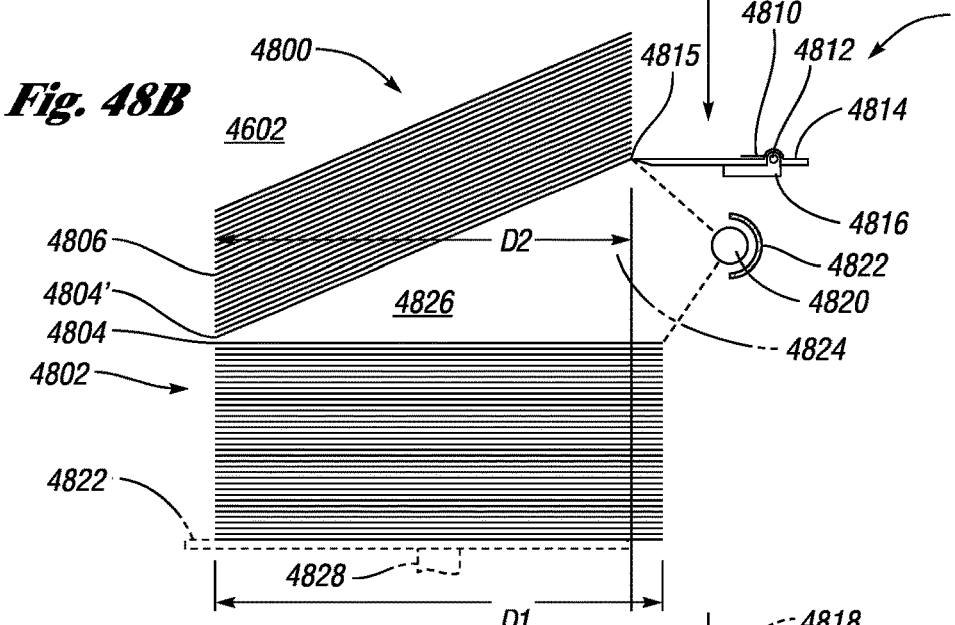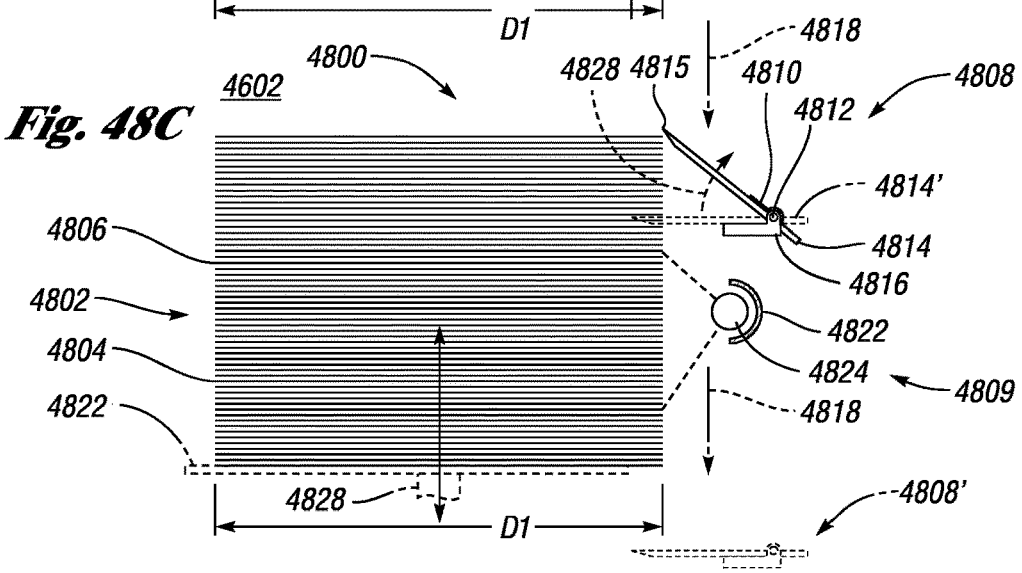

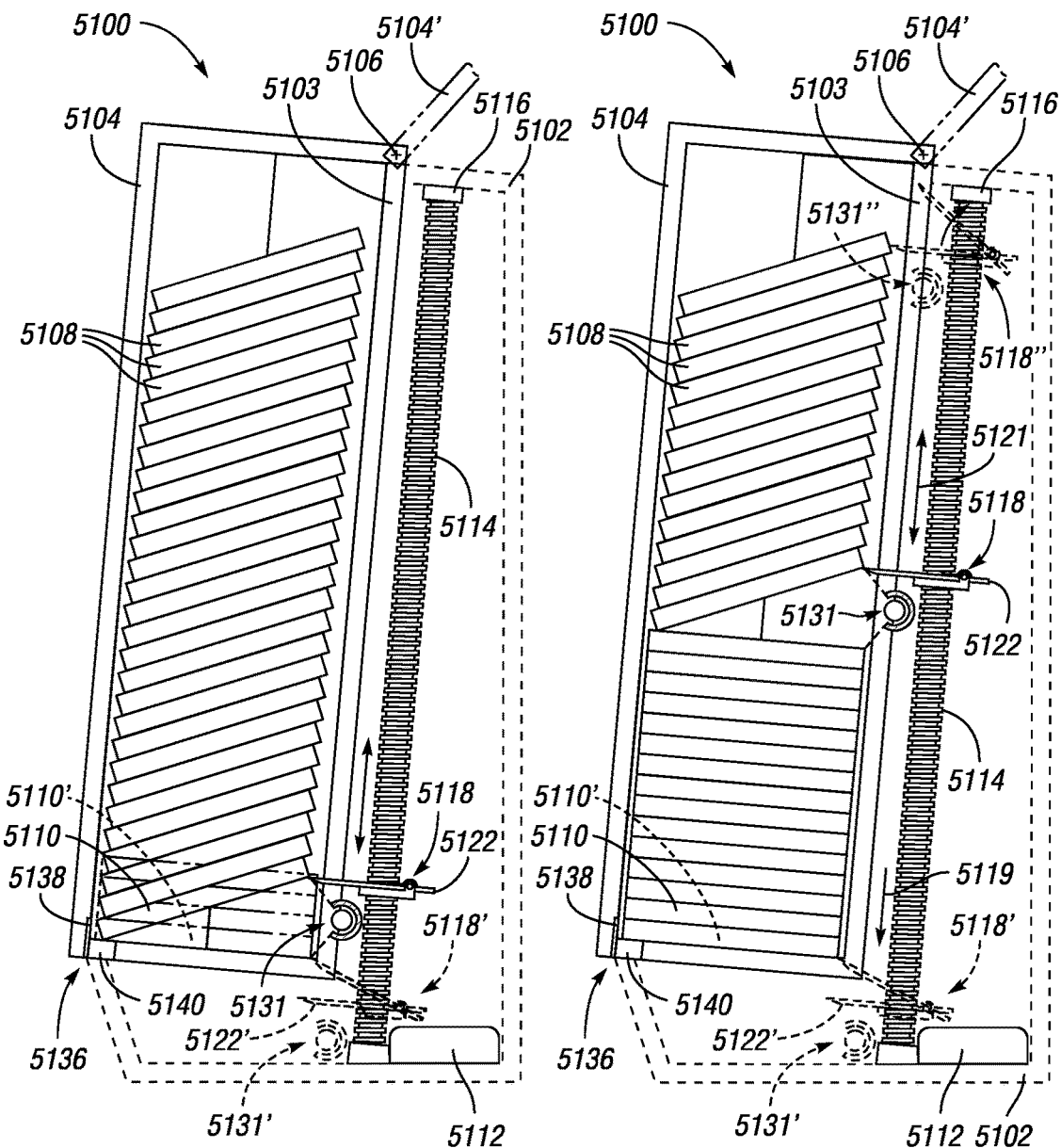
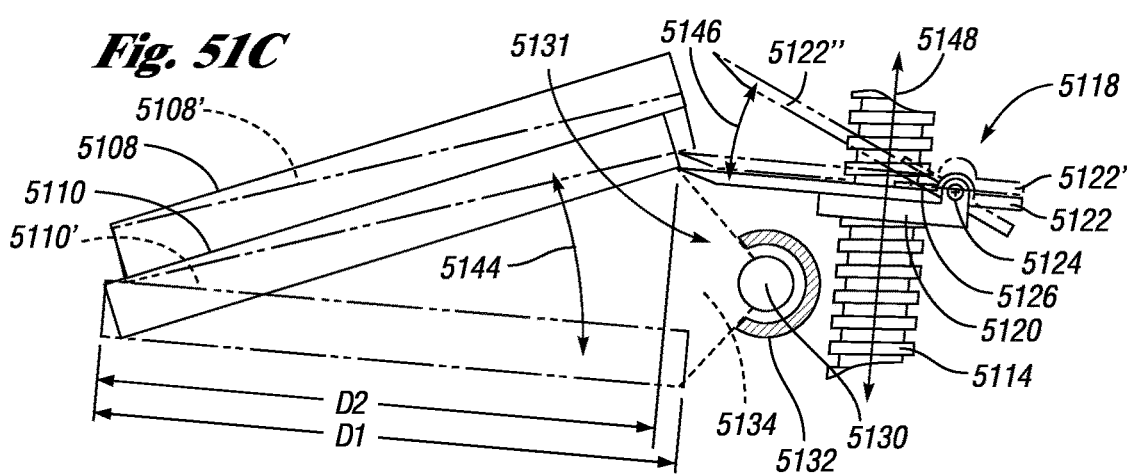
Fig. 51A    Fig. 51B
Fig. 51C

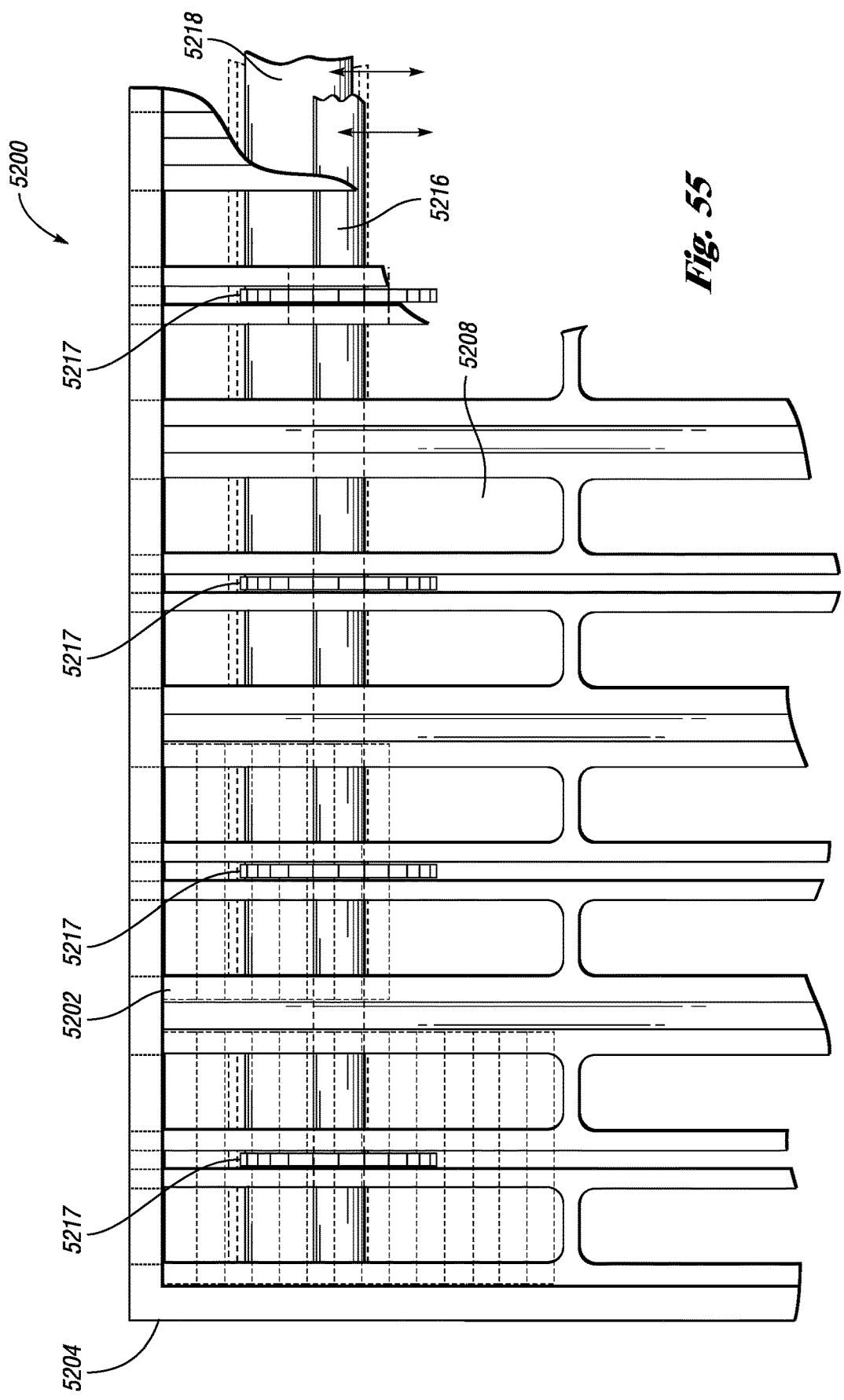

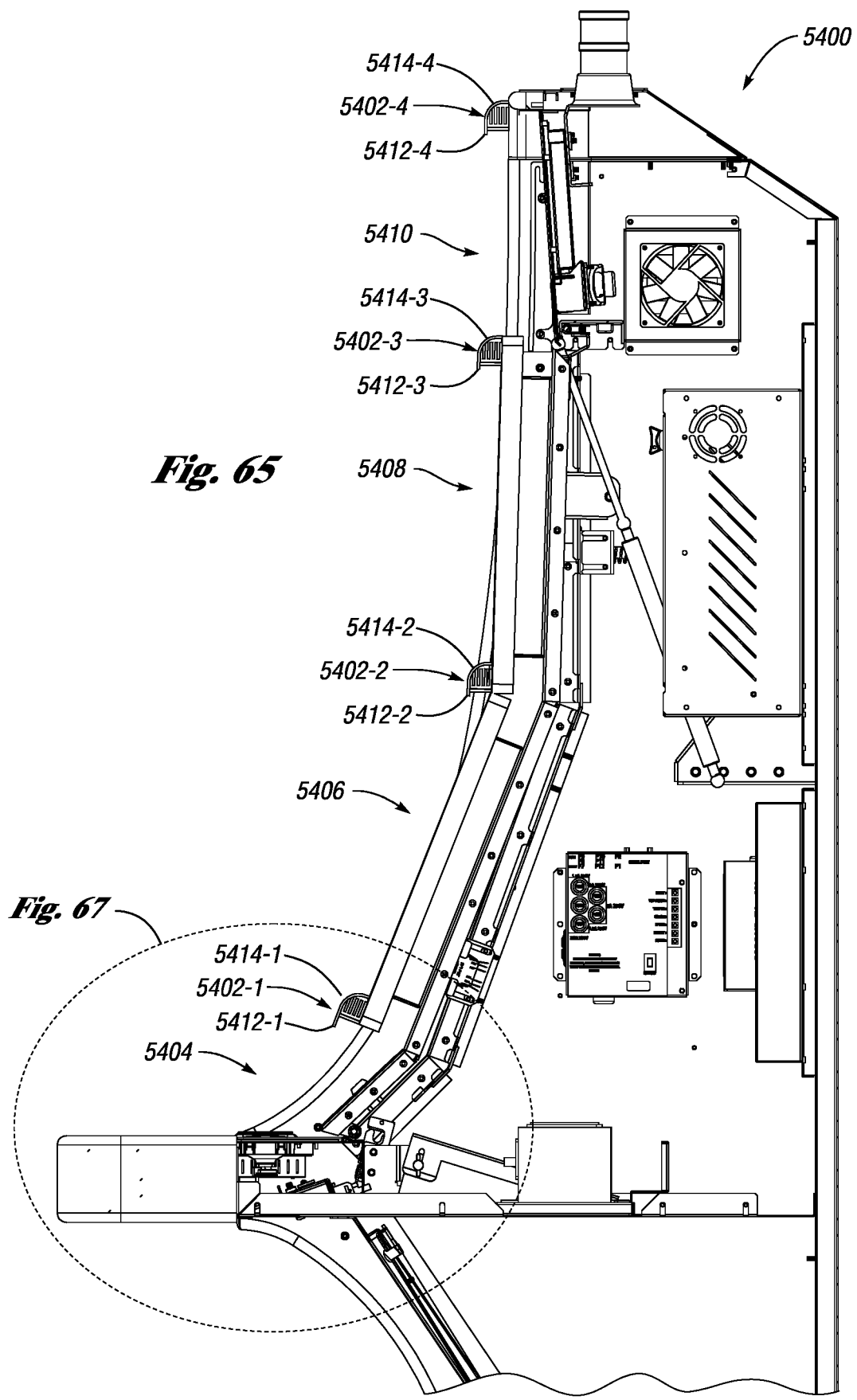

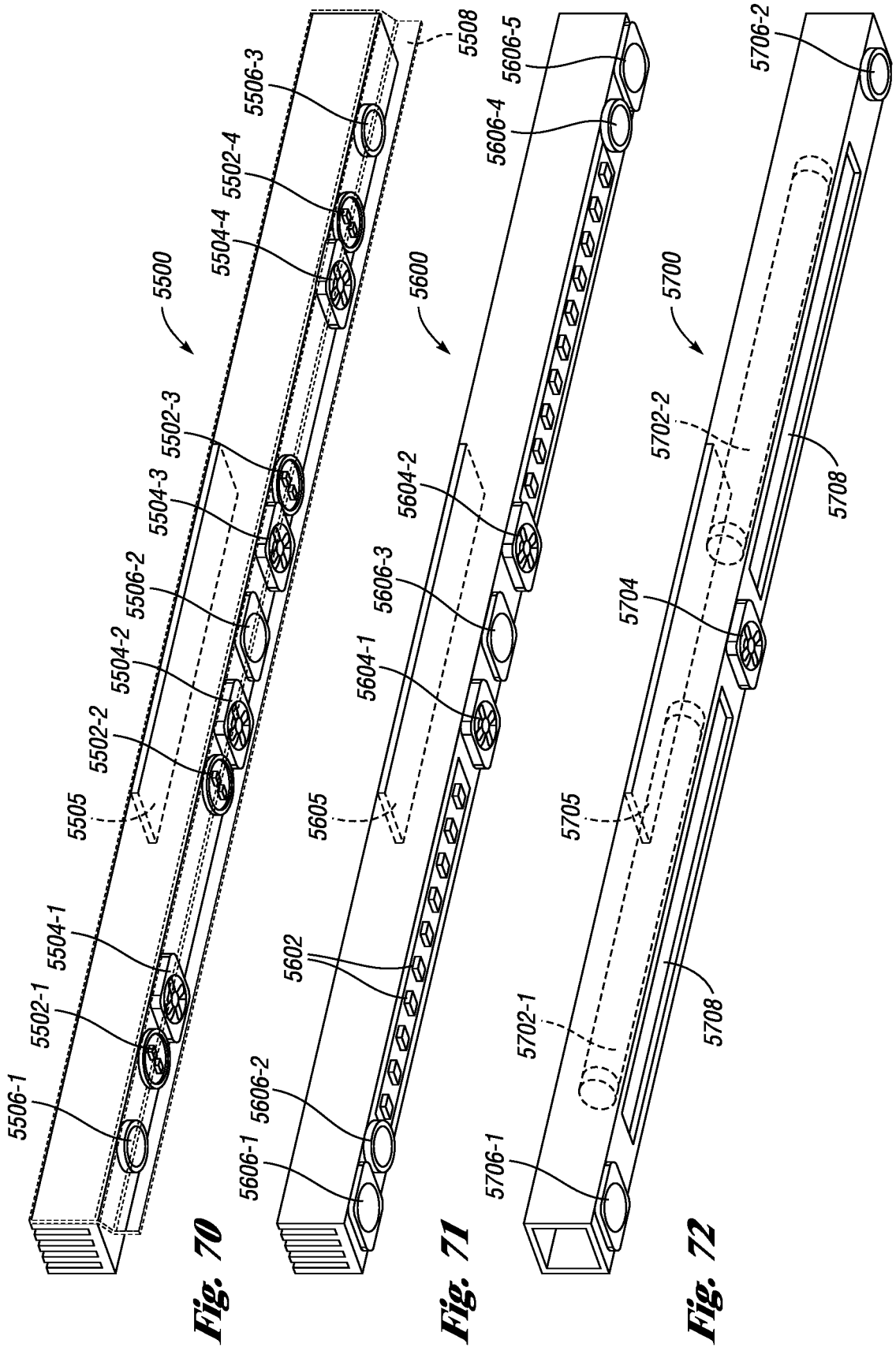

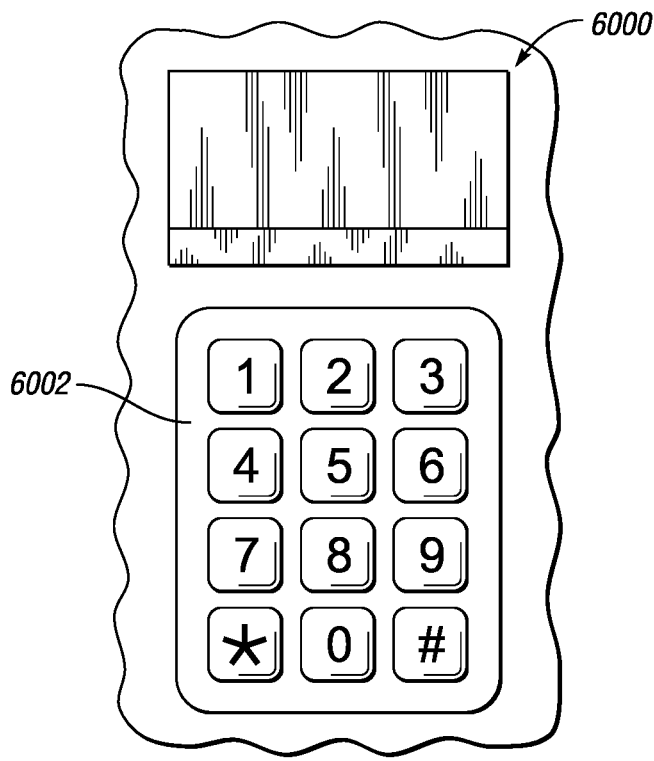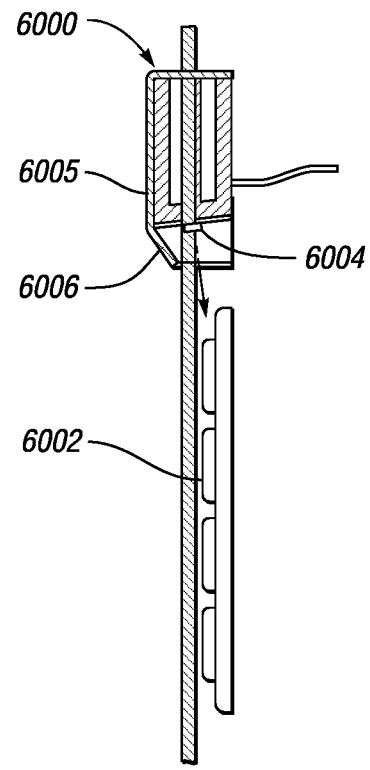
*Fig. 81*     *Fig. 82*
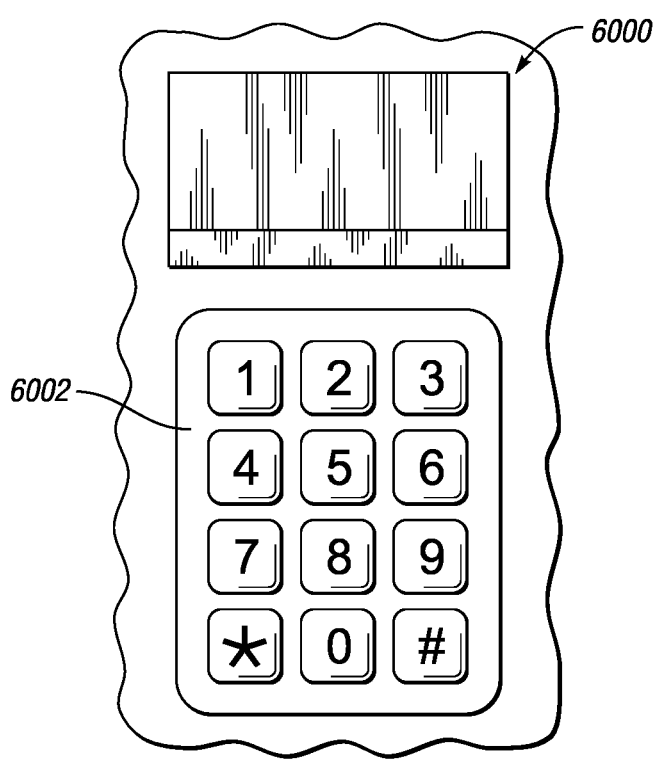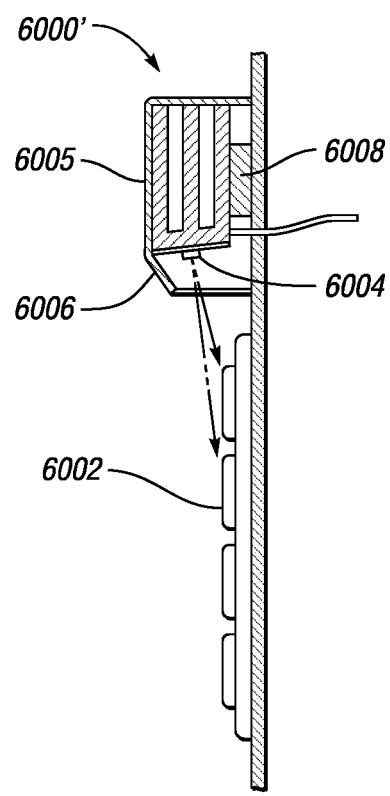
*Fig. 83*     *Fig. 84*

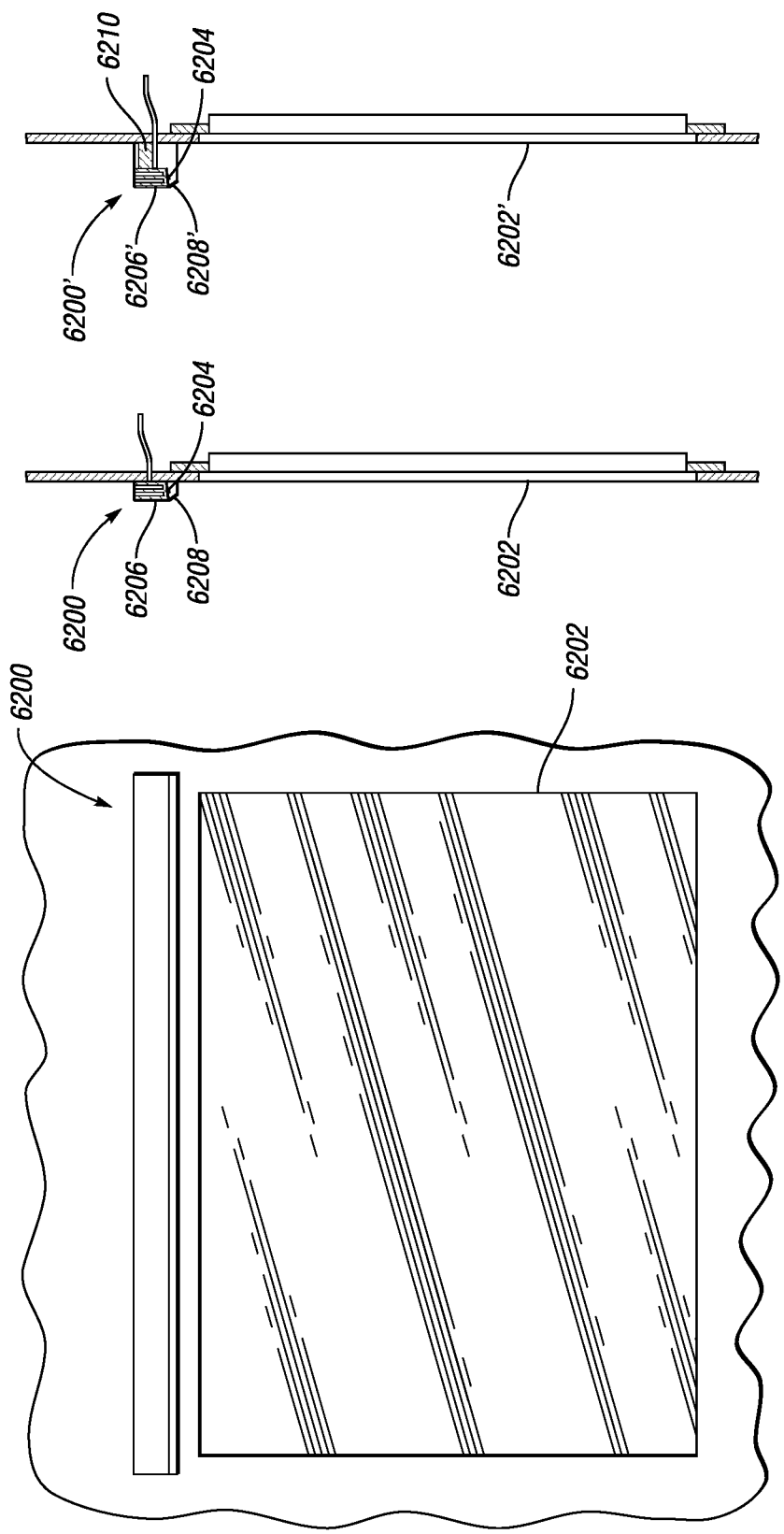

SYSTEMS AND METHODS FOR PROVIDING ULTRAVIOLET STERILIZATION, DISINFECTION AND DECONTAMINATION OF GAMING EQUIPMENT

CROSS-REFERENCE

This application is a continuation-in-part of, and claims priority to, U.S. patent application Ser. No. 15/930,255 filed May 12, 2020, which claims priority to U.S. Patent Application No. 63/012,817 filed Apr. 20, 2020 and this application claims priority to U.S. Patent Application No. 63/199,182 filed Dec. 11, 2020, all of which are incorporated herein by reference for all purposes.

FIELD OF THE INVENTION

The embodiments of the present invention relate to systems and methods for providing ultraviolet sterilization, disinfection and decontamination of gaming machines and components, including mechanical and electronic gaming machines (EGMs) and other gaming equipment and mechanisms utilizing ultraviolet light sources. The embodiments of the present invention contemplate both retrofitting existing and legacy EGMs and other gaming equipment and mechanisms, and future EGMs and other gaming equipment and mechanisms for new installations. Embodiments include a single ultraviolet light source or a plurality of ultraviolet light sources mounted on or in the EGM or other gaming equipment and mechanisms or proximate thereto.

BACKGROUND

Casinos derive much of their gaming revenue from electronic gaming machines ("EGMs") otherwise known as slot machines, either electronic or electromechanical, and a variety of casino table games such as blackjack, roulette, craps, baccarat, etc. In the year 2020, the world is coping with a viral pandemic known as Covid-19 which has effectively caused the closure of most casinos around the globe and substantially all or all casinos and gaming establishments in North America. This closure not only extends to casinos but almost all gaming establishments including sports books, poker parlors, card rooms, bingo halls, keno lounges, etc.

SUMMARY

One skilled in the art will recognize that certain types of EGMs, generally utilized in regulated casino environments, are still commonly referred to as "slot machines." Although the etymology of the term "slot machine" was originally derived from a coin slot in the gaming machines at the time, coin slots have long since generally been replaced by payment input devices or bill validators which only accept paper currency or ticket-in-ticket-out vouchers and/or electronic fund transfer means, such as card readers, mobile device payment means, account interfaces, etc., yet EGMs are still commonly referred to as slot machines. As a result, the terms EGM and slot machine are used interchangeably and are defined to mean an electronic gaming machine entirely different than a laptop or desktop computer, cell phones, tablet computer gaming devices and the like. Although EGMs are discussed in detail, the embodiments of the present invention have similar utility for any type of gaming machine such as electronic, electromechanical or mechanical and regulated as Class II, Class III, VLT, pull tab, etc., type gaming machines.

The embodiments of the present invention provide systems and methods for providing ultraviolet sterilization, disinfection or decontamination of gaming machines and other mechanisms and objects used within a casino environment. The terms sterilization, disinfection and decontamination as used herein, include any partial or full reduction in viruses and the like and include scenarios where no sterilization, disinfection or decontamination of objects can occur but with repeated exposure to the various embodiments disclosed herein before full or partial sterilization, disinfection or decontamination does occur. The embodiments of the present invention allow for a social distancing method so that players may be physically seated at smaller distances than may be suggested by governmental authorities such as a recommended physical separation of at least six feet or 72 inches. As most gaming positions have a physical separation of approximately 28 inches between players, such as in EGM placements or table games, the only alternative without shielding or ultraviolet sterilization, disinfection and decontamination is to turn off, remove, or otherwise eliminate two out of three adjacent gaming positions to create the recommended minimum distance of 72 inches although some casino operators may close off or turn off every other machine, if allowed. This dramatic reduction in gaming positions will essentially force the closure of a great many gaming establishments as revenues will be reduced by approximately up to 70%. For example, a casino with 1,800 EGMs will need to reduce the number to 600 operable EGMs, blackjack tables with six gaming positions will need to reduce to two gaming positions, roulette tables that normally accommodate eight players will need to reduce to two gaming positions, etc. However, social distancing may not fully or even significantly reduce the risk of a virus transmission due to the many other risk factors posed within a casino environment that are not solved by social distancing. The embodiments of the present invention provide systems and methods for providing ultraviolet sterilization, disinfection and decontamination of gaming machines and associated equipment or components for mechanical and electronic gaming machines (EGMs) or casino gaming tables and objects and associated equipment that may allow gaming operators to resume to substantially normal operations. Those skilled in the art will recognize the terms light, lighting, radiate and radiation along with their variations, refer to the production of UV radiation and/or visible light.

Many players, especially in the high spend demographic, are in the 50 to 75 yearold range and have a very different perception of the Covid-19 virus compared to younger people. They have good cause for concern due to age and/or preexisting conditions. Many will be disturbed or concerned when sitting next to unknown players. The embodiments of the present invention help solve this issue and future such issues. In the current environment, one cannot underestimate the number of high spend players that will have ongoing concerns. Although younger people are less concerned, one cannot underestimate a dramatically different view from older, at risk players, who often comprise the highest player spend group. It is important to appreciate that a pandemic will stay for long periods of time, including the Covid-19 virus. Only an effective vaccine will end a pandemic which is typically at least a year or two away with current testing and approval procedures and protocols. As with many viruses, the creation of a vaccine may be elusive and take longer to develop or may not even be possible. While the current Covid-19 pandemic may subside to a large degree in 2021, if and when a vaccine is developed and distributed to the general public, it is sure not to be the last such pandemic which routinely occur in nature. One only needs to look to history to underscore the point. Most recently, the world dealt with the Zika virus in 2015 and still present, the Ebola virus of 2014-2016, the H1N1 Swine Flu pandemic of 2009 to 2010, the Aids pandemic which began in the early 1990s and continues to the present, and the Asian Flu of 1957 to 1958, just to mention the most recent. However, this is the first time in history that the world community has responded with such aggressive preventative and containment measures. It is possible that future pandemics will see similar aggressive actions which may be mitigated if certain sterilization, disinfection and decontamination measures are taken ahead of time. Such is an object of the embodiments of the present invention as it relates to the gaming industry and beyond. When people speak of flattening the infection curve, it is just that, flattening, not eliminating. As an example, while a major city may experience about 800 deaths per day at a certain point, as New York City experienced in early 2020, when the curve flattens, they may still expect 50 to 200 deaths a day for many subsequent months. The same will apply around a country and globe. Currently, as anticipated in the late spring or summer of 2020, when many casinos reopen, they will either be forced or voluntarily choose the turn off every other or two out of three gaming machines as typical slot distancing is only about 28 inches. This, every other or every third machine scenario, will most likely be more prevalent for commercial casinos subject to regulatory authorities than tribal casinos. While this may conform to social distancing guidelines and may help to alleviate player concerns and the spread of a virus, it will cause a dramatic reduction in casino revenues. While a property may reopen, it may not be profitable under this scenario or may even be forced to permanently close. Additionally, this scenario may cause issues with normal consumer traffic as there may not be enough machines on occasion or a player's favorite machine may be turned off, removed, or taken by another player and casino pits and associated table games may not reopen or if they do, only to a very limited degree.

The systems and methods herein for providing ultraviolet sterilization, disinfection and decontamination utilize ultraviolet (UV) light which falls in the range of the electromagnetic spectrum between visible light and X-rays. It has frequencies of about $8 \times 10^{14}$ to $3 \times 10^{16}$ cycles per second, or hertz (Hz), and wavelengths of about 400 nanometers ($1.5 \times 10^{-5}$ inches) to about 10 nm ($4 \times 10^{-7}$ inches). UV is generally divided into three sub-bands:

UVA, or near UV (315-400 nm)
UVB, or middle UV (280-315 nm)
UVC, or high UV (100-280 nm)
Far-UVC (207-222 nm)

UV radiation has enough energy to break chemical bonds. Due to their higher energies, UV photons can cause ionization, a process in which electrons break away from atoms. The resulting electron vacancy affects the chemical properties of the atoms and causes them to form or break chemical bonds that they otherwise would not. This can be useful for chemical processing, or it can be damaging to materials and living tissues. This damage can be beneficial, for instance, in disinfecting surfaces, but it can also be harmful, particularly to skin and eyes, which are most adversely affected by higher-energy UVB and certain UVC radiation. Generally, when bacteria, viruses and protozoa are exposed to adequate UV light, the UV energy destroys the genetic material (DNA) within, eliminating their ability to reproduce and cause infection. Unable to multiply, the microorganisms are "inactivated," and no longer pose a health risk. Accordingly, the proper wavelength ranges need to be selected to balance the disinfecting properties of the UV lighting while not presenting harmful effects on humans. Generally, the proper wavelengths for use with the embodiments of the present invention will fall into the far-UVC range but the shorter UVA wavelength range or even the longer UVB wavelengths may be utilized on occasion. Although perhaps not as efficient as UVC radiation in killing viruses and the like, a tradeoff exists between effectiveness and safety for humans. However, many embodiments of the present invention are designed and constructed to be operable only when humans are not present through the use of various sensors and timers or designed for use only for short periods of time when humans may be present. These embodiments are more effective and in particular, wavelengths of approximately 254 nm and 264 nm or about 207 nm to 222 nm may be very impressive at killing germs, viruses and bacteria. Fortunately, UVC radiation can pass through air without creating ozone, so UVC lamps or LEDs can be used in air to disinfect surfaces. Moreover, the UVC radiation may be shielded in order to radiate only given surfaces as opposed to surrounding areas and such use would generally be for short periods of time. Many lamp types may be used to produce UV radiation such as low-pressure or high-pressure lamps but in the case of the embodiments of the present invention, UV LEDs may be preferable due to size and adaptability to lighting effects and lighting methods used for most EGMs and small size for other gaming mechanisms or objects. In many cases, where humans may be exposed to the UV radiation, far-UVC light, with a wavelength of about 207-222 nm may be the best choice as the wavelength range has been generally proven to be safe for humans yet very effective in killing viruses and the like. Those skilled in the art will recognize that certain embodiments may utilize differing UV wavelengths depending on application, virus characteristics, human exposure factors, and effectiveness.

Those skilled in the art will recognize that casino environments may put humans at more risk than other environments. For instances, over the course of a 24-hour period, a significant number of players will play a particular EGM, potentially contaminating many surfaces on the EGM. EGMs will typically receive a very large number of cash insertions into the EGM for a large number of players, wherein some or many of the bills inserted may be contaminated, printed ticket-in-ticket-out (TITO) paper may have been handled by a number of people prior to filling an EGM printing device and may have been contaminated, numerous players cards may have been inserted into the magnetic card reader thereby potentially contaminating the magnetic card reader, etc. Similar conditions and chances of transmitting viruses also exist in a table games environment. For instance, playing cards are distributed to a significant number of different players over a period of time, including different dealers which is commonplace, any of which could contaminate one or more playing cards or even extend to automatic card shufflers and thereby pose the risk of contaminating other players or dealers.

As playing cards pose a contamination risk, so do gaming chips. In a typical table games environment, gaming chips are routinely transferred from a player to the chip tray or rack when a player loses and conversely leave the chip tray or rack when a dealer awards a payout to a winning player or exchanges them for cash buy-ins. Accordingly, a single gaming chip may often be handled by a multitude of players and dealers over a short time period. While table games utilizing playing cards pose a risk of contamination, similar risks exist on other table games that do not utilize playing cards. Table games such as craps utilize dice during play. Typically, a new player selects two dice from a plurality of dice presented by a craps dealer. Not only may the dice have already been contaminated by a previous player or "shooter" or dealer, it is commonplace for a player to kiss the dice, blow on the dice, spit on the dice, etc., for luck, posing even a greater risk of contamination.

In addition to the risks mentioned, similar contamination risks exist with cash transactions in a casino environment. Typically, cash, usually in the form of currency or even coins, circulate through a casino either from the slot floor or table games to a casino cage, ATMs, and the like. Part of the process in casinos is to drop the slot floor by emptying slot machines or pickup cash boxes from table games. Afterwards, the cash is taken to the count room for counting, accounting and/or other functions. The cash is then either deposited or returned into circulation by the casino cage, filling of ATMs, etc. Not only may the cash have been contaminated prior to a player inserting bills into an EGM or presenting to a table games dealer to obtain gaming chips, it may have already been contaminated prior to a player receiving it from a bank or other financial institution, an ATM, or the casino cage, etc. Accordingly, cash transactions pose a significant risk of contaminating players or casino staff.

Various embodiments of the present invention serve to reduce or eliminate the risk of contamination to player or casino staff through UV decontamination, disinfection and/or sterilization systems and methods. Those skilled in the art will recognize that the terms decontamination, disinfection or sterilization include only partial decontamination, disinfection or sterilization and although a goal would be to fully sterilize, disinfect or decontaminate, often only partially sterilization, disinfection or decontamination of objects used within a casino environment will be accomplished but taken as a group, any reduction of a virus spread is considered a positive advance. Moreover, as objects circulate through a casino environment, they may repeatedly pass through one or more sterilization, disinfection or decontamination stations to increase the effectiveness of the overall sterilization, disinfection and decontamination process.

Embodiments of the present invention may be independent UV generating elements, either shielded or unshielded, as in the case of EGMs or grouped together as adaptive devices for various mechanisms, such as automatic playing card shufflers, ATMs, cash counters, for example. In the case of mechanisms where cash, chips, playing cards, etc., are processed, embodiments of the present invention may be integral with the mechanisms or added to the mechanism, internally or externally, as applicable. As various objects passthrough a sterilization, disinfection and decontamination station of the base mechanism, the UV generating elements may reside on one side, two sides, three sides or all sides of a generally rectangular pass-through window within or attached to the base mechanism. Moreover, for further effectiveness, multiple sterilization, disinfection and decontamination stations may reside in or on the base mechanism. If the sterilization, disinfection or decontamination station is housed within the base mechanism with little or no exposure outside of the interior of the mechanism, higher intensity or alternate UV wavelengths may be employed.

Those skilled in the art will recognize that while UV sterilization, disinfection or decontamination methods for EGMs and various other equipment utilized in a casino environment have been described in detail, similar systems and methods also apply to bar top EGMs, and ancillary gaming equipment, such as bill validators, EGM printers, cash counting devices, card shufflers, ATMs, magnetic card readers, chip trays, chip counters or cleaners, dice trays, etc., or other similar equipment beyond the gaming industry where circumstances warrant.

Those skilled in the art will recognize that the terms approximate, approximately, about, or similar terms, when describing angles or measurements, are not intended to represent exact numbers or limit the scope as additional variations and modifications exist within the scope and spirit of the embodiments of the present invention as described. Instead they are intended as guidelines where the range may be plus or minus up to 20% of the number specified herein. For example, player tracking modules for EGMs are generally mounted on the peripheral deck either vertically or at an angle up to approximately 45° from vertical but may include angles of plus or minus 20% of the 45° specified and the vertical specified may include plus or minus 10° from vertical. Accordingly, a range of approximately 0° from vertical to 45° may be interpreted to include a range of substantially between −10° from vertical to 55° from vertical. Similarly, the terms approximate, approximately, about, or similar terms when referring to wavelengths, may include wavelengths either below or above the stated wavelength. By example, a far-UVC wavelength of about 215 nm may encompass wavelengths between 200 nm and 222 nm.

Other variations, embodiments and features of the present invention will become evident from the following detailed description, drawings and claims.

BRIEF DESCRIPTION OF THE DRAWINGS

FIG. 32 illustrates a perspective view of an automated dice boat UVC disinfecting unit according to the embodiments of the present invention.

FIG. 33 illustrates a perspective view of an automated dice boat UVC disinfecting unit according to the embodiments of the present invention shown in a loading/unloading position.

FIG. 34 illustrates a top plan view of an automated dice boat UVC disinfecting unit according to the embodiments of the present invention shown in a loading/unloading position.

FIG. 35 illustrates a perspective view of an automated dice boat UVC disinfecting unit according to the embodiments of the present invention.

FIG. 36 illustrates a perspective view of an automated dice boat UVC disinfecting unit according to the embodiments of the present invention shown in a loading/unloading position.

FIG. 37 illustrates a top plan view of an automated dice boat UVC disinfecting unit according to the embodiments of the present invention shown in a loading/unloading position.

FIG. 39 illustrates a section view taken along lines 39-39 in FIG. 38 of a manual opening UVC dice disinfecting unit according to the embodiments of the present invention shown in a loading/unloading position.

FIG. 40 illustrates a section view taken along lines 40-40 in FIG. 38 of a manual opening UVC dice disinfecting unit according to the embodiments of the present invention shown in a loading/unloading position.

FIG. 41 illustrates a section view taken along lines 41-41 in FIG. 38 of a manual opening UVC dice disinfecting unit according to the embodiments of the present invention shown in a loading/unloading position.

FIG. 44 illustrates a perspective view of an upper and lower UVC chamber according to the embodiments of the present invention.

FIG. 45 illustrates a cross section view of an upper and lower UVC chamber according to the embodiments of the present invention further illustrating the paths of direct and reflective UVC radiation.

FIG. 48A illustrates a perspective view of a playing card disinfecting unit including a stack separator mechanism according to the embodiments of the present invention in a first position.

FIG. 48B illustrates a perspective view of a playing card disinfecting unit including a stack separator mechanism according to the embodiments of the present invention in a second position.

FIG. 48C illustrates a perspective view of a playing card disinfecting unit including a stack separator mechanism according to the embodiments of the present invention in a third position.

FIG. 51A illustrates a cross section view of a gaming chip disinfecting unit including a stack separator mechanism according to the embodiments of the present invention in a first position.

FIG. 51B illustrates a cross section view of a gaming chip disinfecting unit including a stack separator mechanism according to the embodiments of the present invention in a second position.

FIG. 51C illustrates a cross section view of a gaming chip disinfecting unit including a stack separator mechanism according to the embodiments of the present invention in a third position.

FIG. 55 illustrates an enlarged broken away top plan view of a gaming chip disinfecting unit including a stack separator mechanism according to the embodiments of the present invention.

FIG. 65 illustrates a cross section side view of an electronic gaming machine further illustrating various placement options of a UVC disinfection bar according to the embodiments of the present invention.

FIG. 70 illustrates a perspective view of a UVC disinfection bar according to the embodiments of the present invention utilizing UVC LED modules, cooling fans, and associated sensors.

FIG. 71 illustrates a perspective view of a UVC disinfection bar according to the embodiments of the present invention utilizing individual UVC LEDs, cooling fans, and associated sensors.

FIG. 72 illustrates a perspective view of a UVC disinfection bar according to the embodiments of the present invention utilizing UVC lamps, one or more cooling fans, and associated sensors.

FIG. 81 illustrates a partial front elevation view of a UVC disinfection bar according to the embodiments of the present invention attached above a keypad.

FIG. 82 illustrates a partial side cross section view of a UVC disinfection bar according to the embodiments of the present invention attached above a keypad.

FIG. 83 illustrates a partial front elevation view of a UVC disinfection bar according to the embodiments of the present invention attached above a keypad including a spacer.

FIG. 84 illustrates a partial side cross section view of a UVC disinfection bar according to the embodiments of the present invention attached above a keypad including a spacer.

FIG. 85 illustrates a partial front elevation view of a UVC disinfection bar according to the embodiments of the present invention attached above a touch screen display.

FIG. 86 illustrates a partial side cross section view of a UVC disinfection bar according to the embodiments of the present invention attached above a touch screen display.

FIG. 87 illustrates a partial side cross section view of a UVC disinfection bar according to the embodiments of the present invention attached above a touch screen display including a spacer.

DETAILED DESCRIPTION

Figure 1:
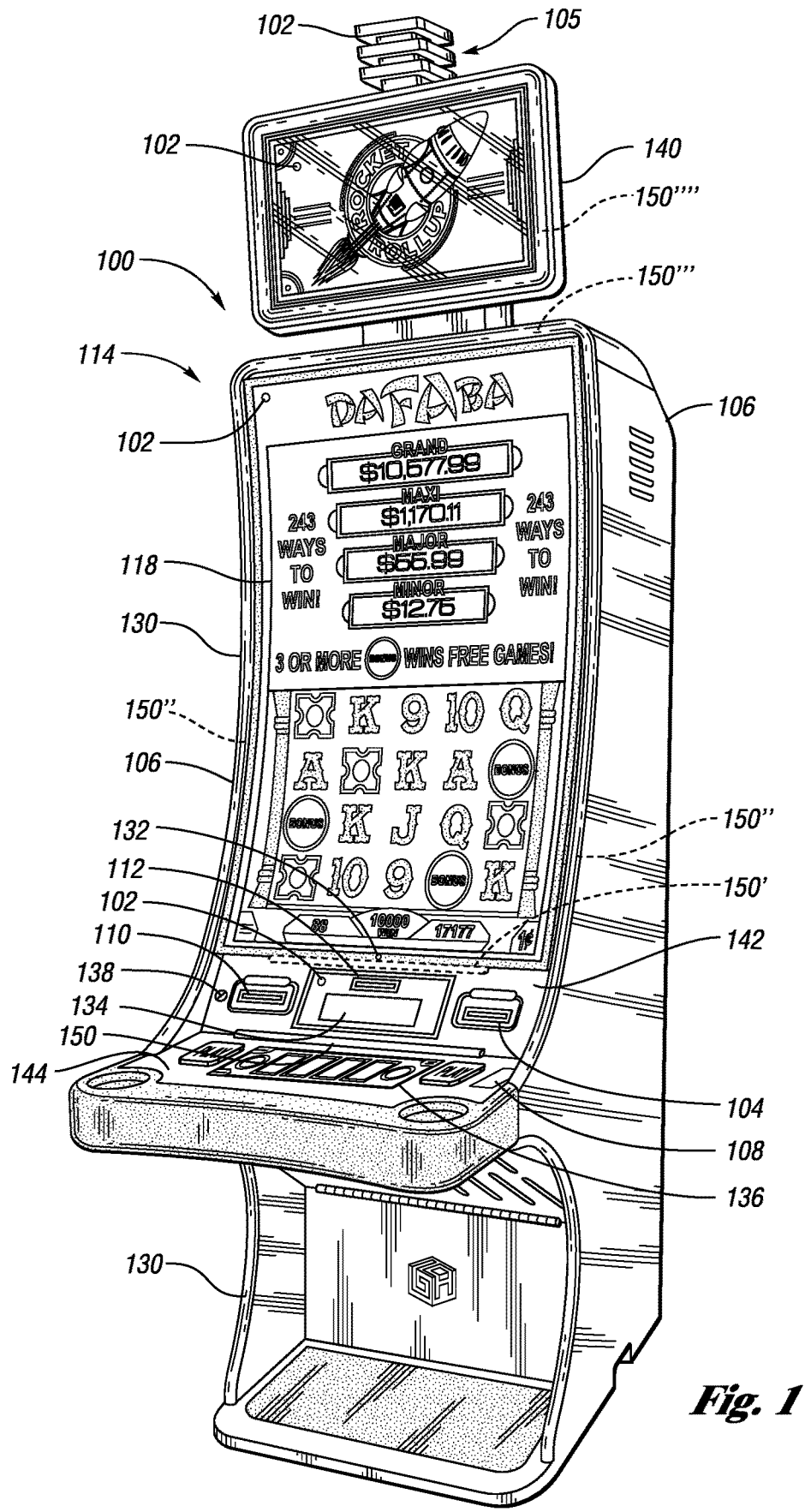
FIG. 1 illustrates a conventional floor mounted or slant type (also known as a hybrid EGM) electronic gaming machine including UV sterilization, disinfection and decontamination elements of the embodiments of the present invention.

For the purposes of promoting an understanding of the principles in accordance with the embodiments of the present invention, reference will now be made to the embodiments illustrated in the drawings and specific language will be used to describe the same. It will nevertheless be understood that no limitation of the scope of the invention is thereby intended. Any alterations and further modifications of the inventive feature illustrated herein, and any additional applications of the principles of the invention as illustrated herein, which would normally occur to one skilled in the relevant art and having possession of this disclosure, are to be considered within the scope of the invention claimed. While the present invention may be embodied in many different forms, as may be shown in the drawings and described herein in specific detail, this disclosure is to be considered as an exemplification of the principles of the invention as well as the best mode of practicing same and is not intended to limit the broad aspects or scope of the invention or claims to the specific embodiments illustrated or described.

One skilled in the art will recognize that the present invention is described below in such detail required to construct a sterilization, disinfection and decontamination mechanism of the various embodiments of the present invention.

As will be appreciated by one skilled in the art, aspects of the present invention may be embodied as a system or method.

FIG. 1 is an illustration of an exemplary electronic gaming machine (EGM) 100 that may be used with the systems and methods described herein. In one embodiment, EGM 100 is a gaming device 114. EGM 100 may include one or more comp indicators 102, which may be incorporated into, or implemented by, a candle device 105, lighting element 130, displayed on monitor 118, displayed on the player tracking module 134, displayed as an LED indicator on button panel 136 which is located on the button deck 144, or another device. One or more cameras 132 may be provided with or as part of the EGM 100 to capture images of the player or other aspects of game play. In addition to capturing images of a player or other aspects of the game, the camera 132 may be an infrared or combination infrared and normal light range camera that is able to take an infrared photo of a player and determine the body temperature of a player. If a processor determines that the temperature of a player exceeds preestablished limits, it can notify management and/or staff through the slot accounting system, can notify the player directly via a visual or audio message on the game, player tracking module display, or LCD button deck, can notify staff via a signal on the EGM candle 105, can process a signal to a player via their cell phone or a monitoring person's cell phone, or any other convenient means of notification. In this way, when an operator is notified, they may be able to ask the high temperature player to leave the premises, recommend medical attention or further evaluation, restrict the player's movement, trace the player's movements, notify other guests or players, notify the player's friends or family, or similar, The button deck of hybrid or slant type EGMs generally projects outwardly from the main cabinet and may be horizontally disposed or at slight angles from horizontal and also serves as an armrest for the play. Button decks on upright type EGMs generally project out less from the main cabinet and may not contain enough room to serve as an armrest for the player. Button decks of bar top EGMs are located below the main game screen, closer to the player, with the armrest provided by the bar top itself or bar top armrest or bar rail.

The EGM 100 includes one or more screens and may include a curved portrait mounted screen 118 although other screens or screen configuration may also be employed such as, flat screen, J-curve, reverse J-curve, S-curve multiple horizontal monitors, etc. The screen 118 may be configured to display game content to the player or any other information regarding the game, the casino, rules, pay tables, promotions, advertisements, or any multimedia content. In one embodiment, the screen 118, also referred to as a primary game display, may comprise multiple, separate displays. Additional lights 130 may be incorporated into the gaming machine to providing lighting for the player or ornamentation for the EGM 100.

A scanner 108 is provided to scan tickets which have bar or box codes, or for scanning money, cards, or any other media. In addition, scanner 108 may include other connectivity means such as blue tooth communications, near field communications or similar. Similar, a card reader 112 is provided to read one or more aspects of cards, such as player tracker or rewards cards, personal identification cards, electronic funds transfer (EFT) cards, and/or credit cards and is located on the peripheral deck 142. The EGM 100 may also include a printer 110. The printer 110 may print on any type media depending on the printer capabilities. Any type content may be printed including but not limited to cash out tickets (also known as ticket-in-ticket-out or TITO tickets or vouchers), coupons, gift certificates, comps, prizes, gaming codes, redemption codes, bar or box codes, receipts, IRS reporting documents, or any other type of information. Also, part of this embodiment is a cash acceptor 104 configured to accept paper money, ticket-in-ticket-out vouchers, or any type physical item associated with the gaming machine 100. A USB port 138 or other type charging or I/O port such as an induction charging unit is provided for phone charging or interfacing the user's phone to the gaming machine. Numerous other buttons and player interface elements are presented with the gaming machine to accept player input. The screen 118 may be configured as a touch screen.

As illustrated, the EGM 100 includes sterilization, disinfection and decontamination mechanism 150 of the embodiments of the present invention attached at the junction of the button deck 144 and peripheral deck 142 of the EGM 100. Those skilled in the art will recognize that while the sterilization, disinfection and decontamination mechanism 150 is shown at the junction of the button deck and peripheral deck, this is but one location that will serve the purpose of the embodiments of the present invention. As used herein "sterilization, disinfection and decontamination mechanism" may include one or more active members (e.g., UV LEDs). Many alternative locations exist for one or a plurality of sterilization, disinfection and decontamination mechanisms. Such mechanisms may even be built into the conventional LED lighting strips 130 wherein two separate LED strips, one a RGB LED strip and the other a UV LED strip, are included within the LED lens or cover or every other LED may be a RGB LED alternating with UV LEDS, or similar. Alternate locations of the sterilization, disinfection and decontamination mechanisms of the embodiments of the present invention are shown in locations, 150', 150", 150'" and 150"", and 150""'. These locations may be independent or part of a plurality of sterilization, disinfection and decontamination mechanisms operating together. Similar alternate locations exist for all of the various embodiments of the present invention. The only true limitation associated with locating the sterilization, disinfection and decontamination mechanisms is the ability of the radiated UV light to reduce the virus, bacteria or similar life form that it is intended to control. Those ordinarily skilled in the art will recognize that the LED lighting strips 130 may be flush with the surface of the EGM 100, may be raised above the surface of the EGM 100, may be in the form of edge lit lighting panels attached to the EGM 100, etc. In addition, several locations may serve not only to allow for convenient attachment to the EGM 100 but at the same time shield the UV radiation from direct exposure to the player. Such locations may also allow for increased UV intensity, if desired. For instance, UV location 150' may attach to the EGM 100 display 118. If the UV lighting is located on the exterior bezel of display 118, it will allow for direct exposure to not only portions of the EGM 100 but to the player as well. Alternatively, the UV location may be mounted on the bottom face of the display 118 housing whereas the UV radiation will be generally directed downwardly and be generally directed onto the button deck 144 and peripheral deck 118. However, as illustrated, display 118 is raised or floats above a support structure which allows for the UV location 150' to be located on the underside of display 118 or the bottom face of a recessed display support structure, where the lower edge portion of display 118 will shield UV location 150' allowing exposure to the button deck and peripheral devices but not or at least limited direct exposure to the player generally beyond their arms and hands. Of course, the angularity of the non-shielded UV lighting will be governed by the geometric relationship between location 150' and the display 118.

Figure 2:
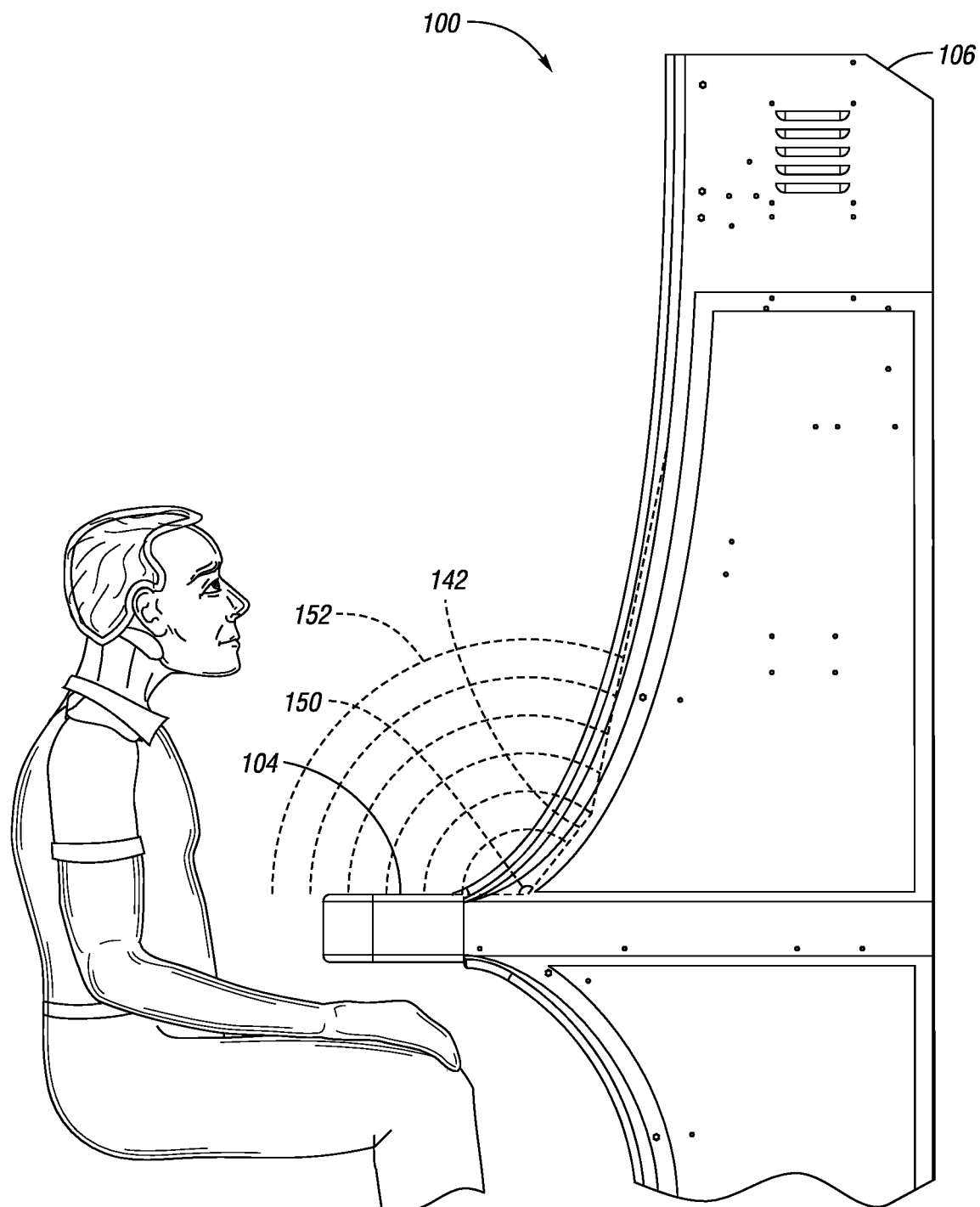
FIG. 2 illustrates a side view of a conventional slant style electronic gaming machine, normally placed on the casino floor, including UV sterilization, disinfection and decontamination elements of the embodiments of the present invention.

FIG. 2 illustrates an elevational side view of a conventional slant style electronic gaming machine 100 including the EGM cabinet 106 and sterilization, disinfection and decontamination mechanism 150 of the embodiments of the present invention. As illustrated, the sterilization, disinfection and decontamination mechanism 150 of the embodiments of the present invention is located at the junction of the button deck and peripheral deck. The UV radiation radiates from the sterilization, disinfection and decontamination mechanism 150 of the embodiments of the present invention and is illustrated as curved broken lines 152. As illustrated in FIG. 1, many different locations may exist for the sterilization, disinfection and decontamination mechanism 150 of the embodiments of the present invention.

Figure 3:
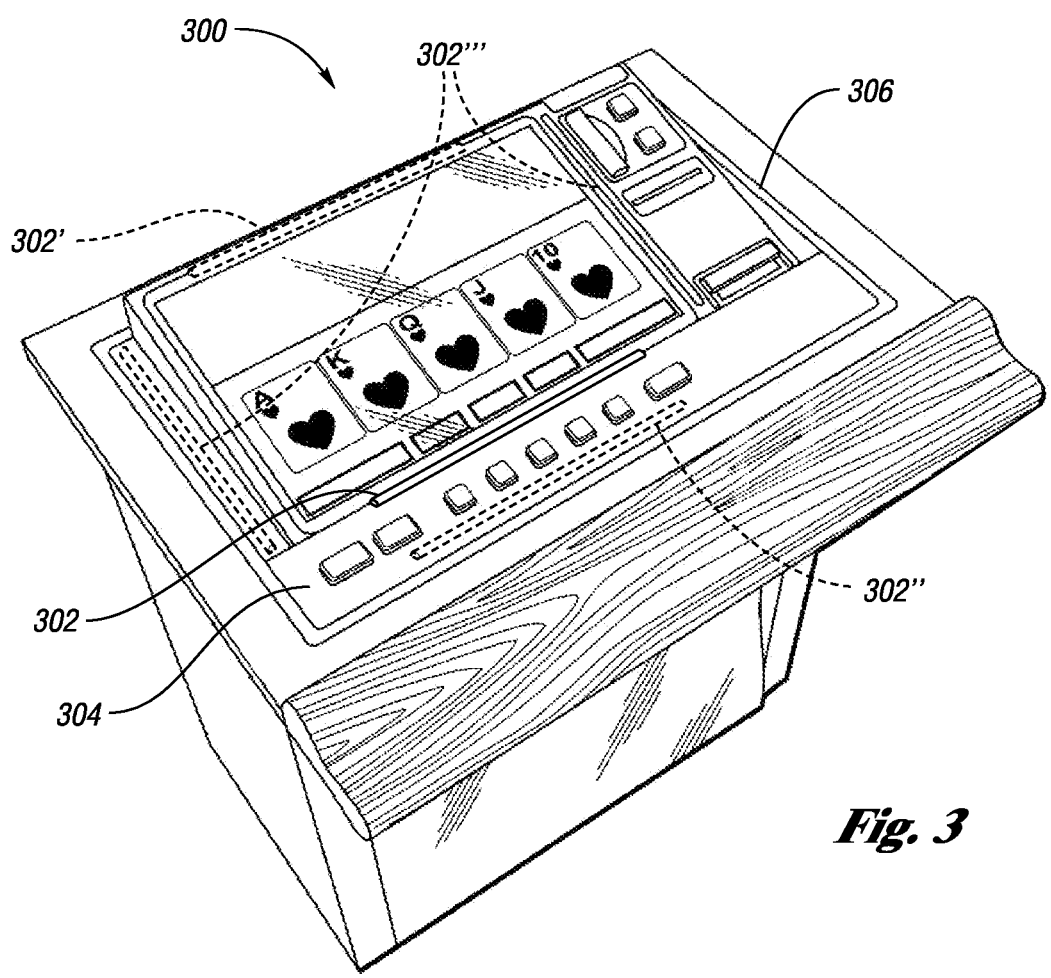
FIG. 3 illustrates a conventional bar top type electronic gaming machine including UV sterilization, disinfection and decontamination elements of the embodiments of the present invention.

FIG. 3 illustrates a conventional bar top type electronic gaming machine 300 including the EGM cabinet 306 and sterilization, disinfection and decontamination mechanism 302 of the embodiments of the present invention. As illustrated, the sterilization, disinfection and decontamination mechanism 302 of the embodiments of the present invention is located on the button deck 304. Many different locations may exist for the sterilization, disinfection and decontamination mechanism 302 of the embodiments of the present invention as shown in locations 302', 302" and 302'". Either a single sterilization, disinfection and decontamination mechanism may be utilized or a plurality of sterilization, disinfection and decontamination mechanisms may also be employed as shown with sterilization and decontamination mechanism 302'".

Figure 4:
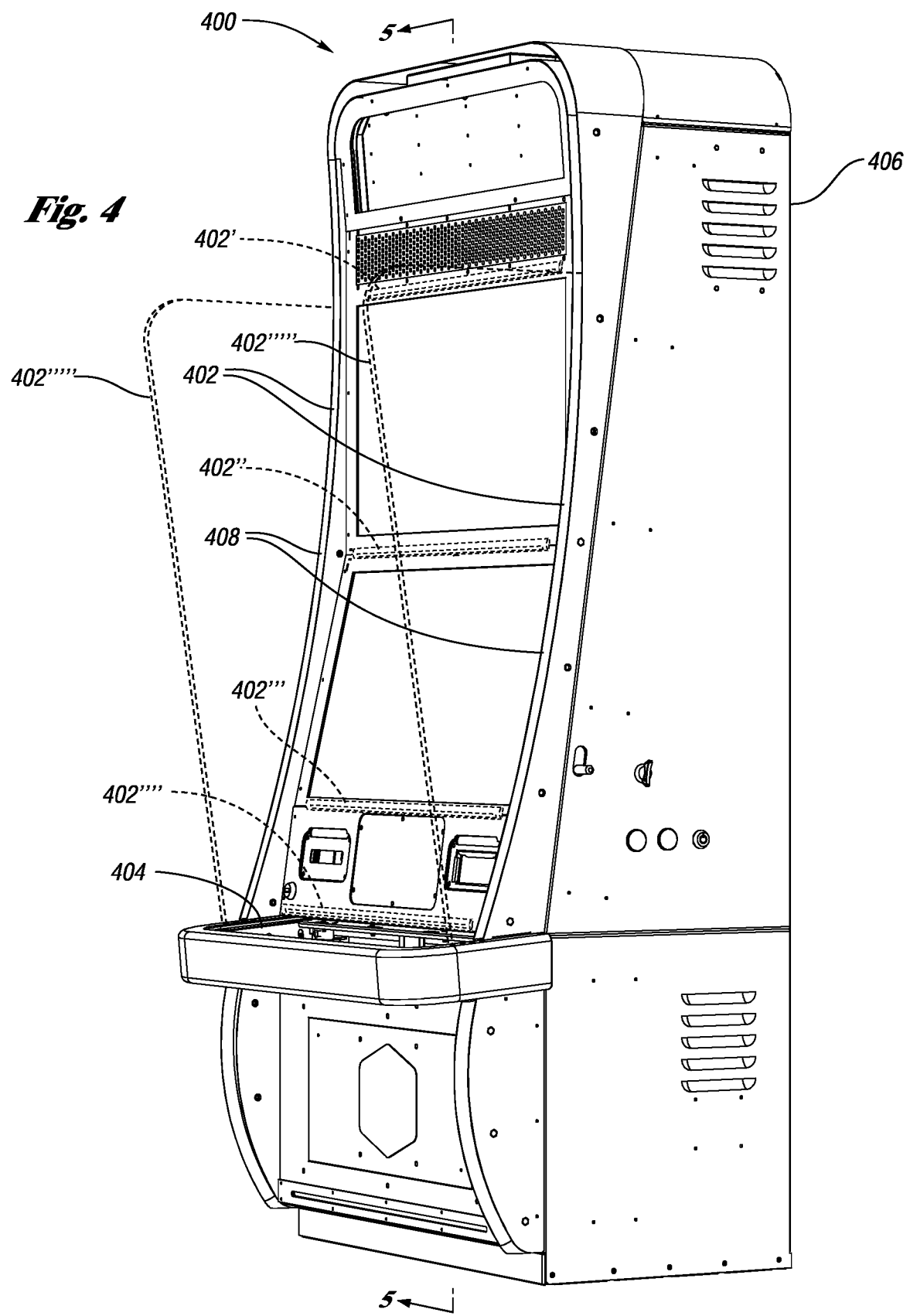
FIG. 4 illustrates a side elevational view of a conventional upright style electronic gaming machine, normally placed on a slot stand, including UV sterilization, disinfection and decontamination elements of the embodiments of the present invention.

FIG. 4 illustrates a side perspective view of a conventional upright style gaming machine 400. The conventional upright gaming 400 machine includes cabinet 406 and button deck 404. The sterilization, disinfection and decontamination mechanism 402 in this embodiment exists within the decorative LED lighting strips 408 but may be located in any convenient and effective location such as 402', 402", 402'", 402"", 402""', or other location. Shown in phantom lines are edge lit side panels 402"'" to which the sterilization, disinfection and decontamination mechanism 402 may be attached. Those ordinarily skilled in the art will recognize that the LED lighting strips 400 may be flush with the surface of the EGM 400, may be raised above the surface of the EGM 100, may be in the form of edge lit lighting panels 402"'" attached to the EGM 400, etc.

Figure 5:
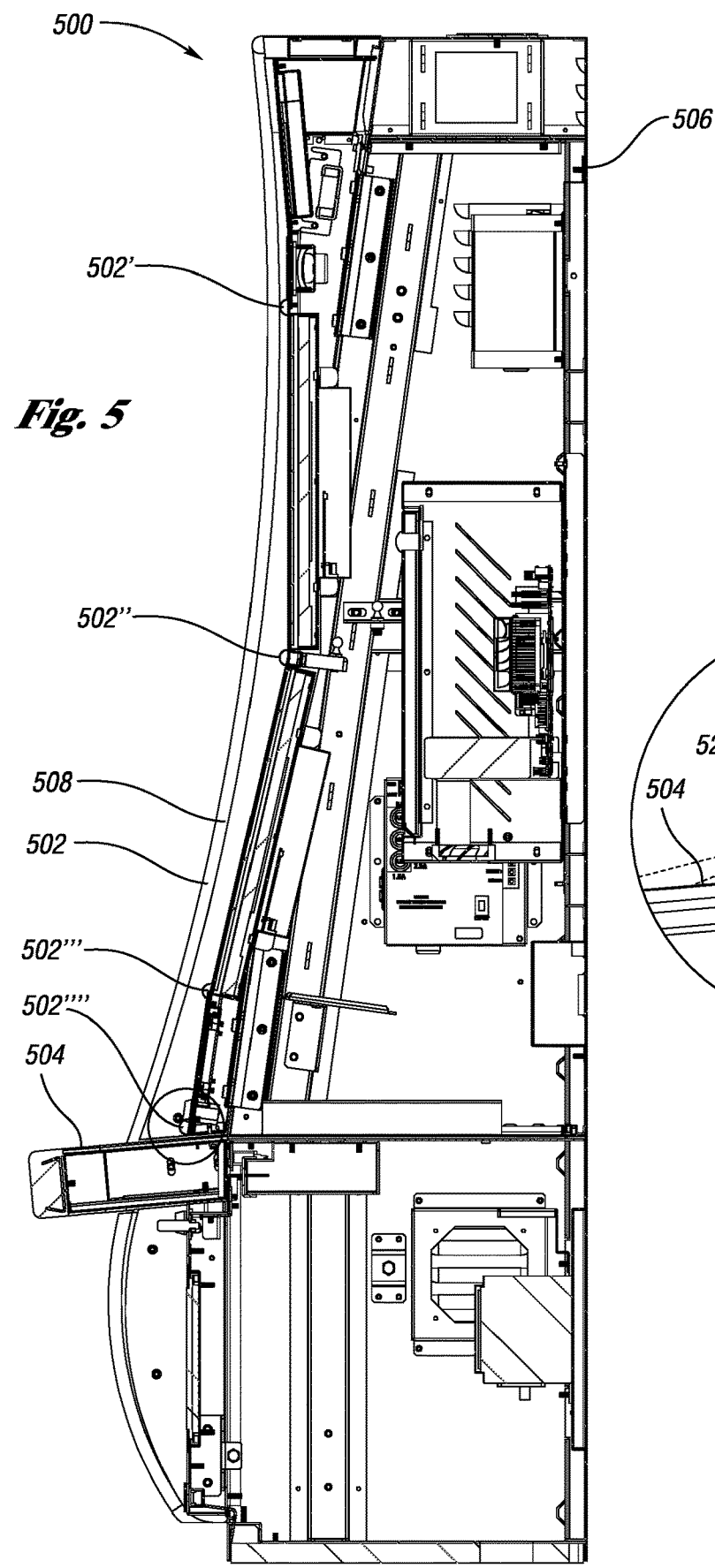
FIG. 5 illustrates a cross section view of a conventional upright style electronic gaming machine, generally placed on a slot stand, including UV sterilization, disinfection and decontamination elements of the embodiments of the present invention.

FIG. 5 illustrates a cross section view of an upright style gaming machine 500. The conventional upright gaming 500 machine includes cabinet 506 and button deck 504. The sterilization, disinfection and decontamination mechanism 502 in this embodiment is part of the decorative LED lighting strips 508 but may be located in any convenient and effective location such as 502', 502", 502'", 502"" or other location.

Figure 5A:
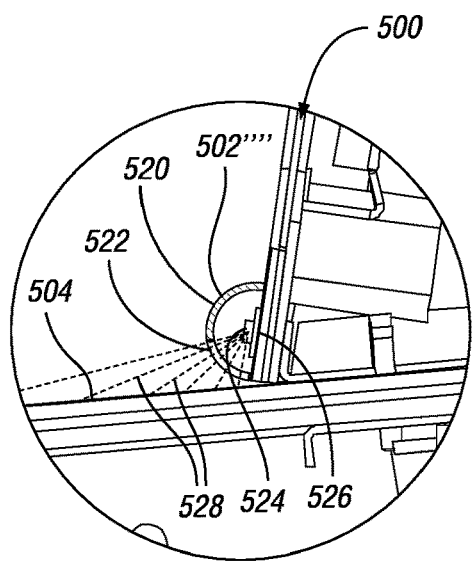
FIG. 5A illustrates an enlarged cross section view of an upright style gaming machine including UV sterilization, disinfection and decontamination elements of the embodiments of the present invention.

FIG. 5A illustrates an enlarged cross section view of an upright style gaming machine 500. As previously described, the sterilization, disinfection and decontamination mechanism 502 may be located in any convenient location on the gaming machine 500 such as that illustrated. In any embodiment of the present invention, it may be desirable to shield the UV radiation to minimize potential detrimental effects to humans, whether real or imagined. As shown, sterilization, disinfection and decontamination mechanism 502 includes a shielding housing member 520 that at least partially encloses a UV strip 526 and UV light source 524. Passage 522 in the sterilization, disinfection and decontamination mechanism 502 allows for the UV radiation to escape from the sterilization, disinfection and decontamination mechanism 502 and radiate the top of the button deck 504, thereby sterilizing, disinfecting and decontaminating the button deck surface, buttons, and other features on the button deck 504 as illustrated by schematic radiation lines 528. Passage 522 may be an open passage, a clear lens, a translucent lens, or similar. As illustrated, the radiation is largely unable to reach the player due to the shielding mechanism 520 which largely prohibits direct radiation beyond the button deck 504. UV light source 524 may be a single or a plurality of UV light sources such as UV LEDs or other type UV light sources. In any embodiment of the present invention, it may be desirable to also include RGB or similar LED lighting to enhance the aesthetics of the gaming machine 500. Such aesthetics can also be obtained by use of a combination RGB-UV LED or alternating RGB and UV LEDs. Typically, for this or any embodiment of the present invention, it may be desirable to utilize addressable LEDs to enhance lighting effects or moderate the UV radiation, whether they be separate LEDs or combination RGB-UV LEDs.

Figure 6:
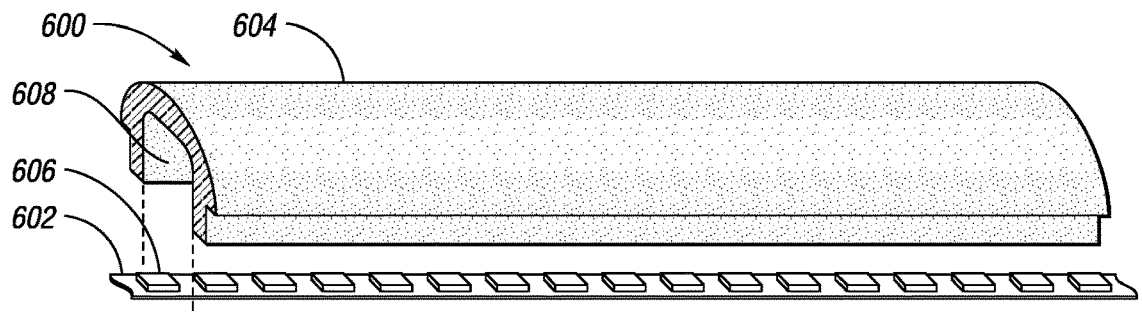
FIG. 6 illustrates an exploded perspective view of prior art decorative RGB LED strip lighting used on gaming machines along with a translucent cover or lens.

FIG. 6 illustrates an exploded cross section perspective view of prior art decorative RGB LED strip lighting assembly 600 used on gaming machines including a RGB LED light strip 602 along with a translucent cover or lens 604. As illustrated, the RGB light strip 602 includes a plurality of individual RGB LEDs 606 which are received within a channel 608 defined by the translucent cover or lens 604.

Figure 7:
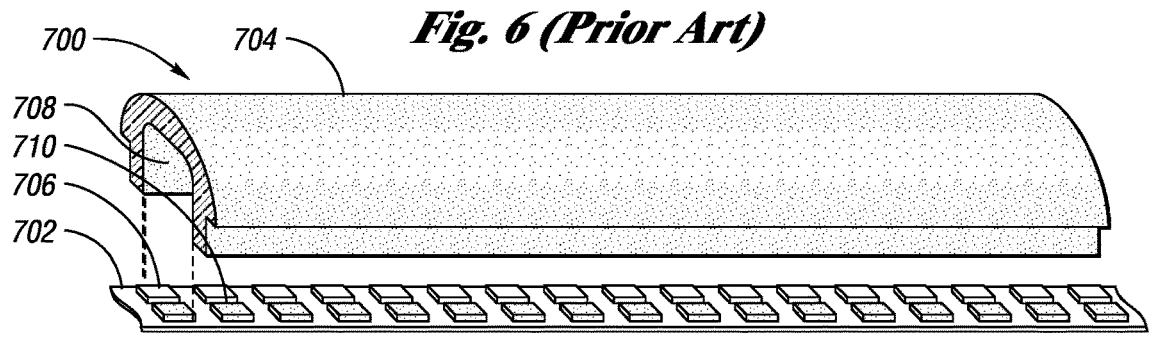
FIG. 7 illustrates an exploded perspective view of decorative RGB LED strip lighting plus an UV LED strip used together on gaming machines along with a translucent cover or lens to provide sterilization, disinfection and decontamination elements of the embodiments of the present invention.

FIG. 7 illustrates an exploded cross section perspective view of decorative RGB-UV LED strip lighting assembly 700 used on gaming machines including a RGB-UV LED light strip 702 along with a translucent cover or lens 704. As illustrated, the RGB-UV light strip 702 includes a plurality of individual RGB LEDs 706 and a plurality of UV LEDs 710 which are received within a channel 708 defined by the translucent cover or lens 704. Although shown on common strip 702, the plurality of RGB LEDs 706 may reside on a first strip and the UV LEDs 710 may reside on a second separate strip. As used throughout this disclosure, the LEDs may be addressable or non-addressable.

Figure 8:
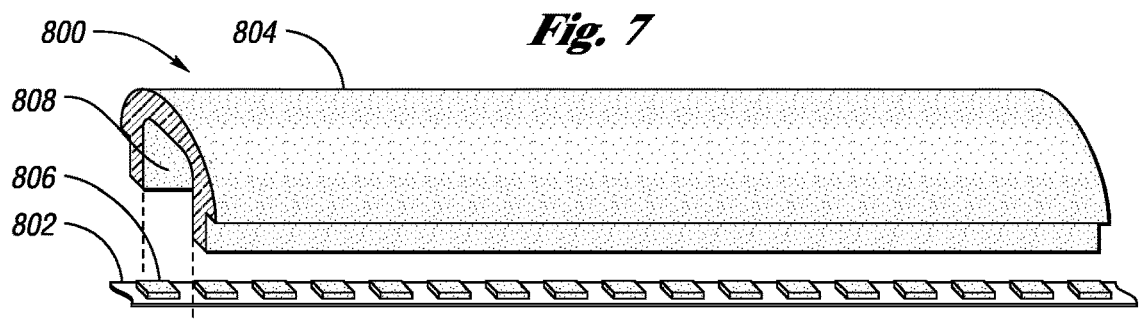
FIG. 8 illustrates an exploded perspective view of UV LED strip used on gaming machines along with a translucent cover or lens to provide sterilization, disinfection and decontamination elements of the embodiments of the present invention.

FIG. 8 illustrates an exploded cross section perspective view of another embodiment of a decorative UV LED strip assembly 800 used on gaming machines including a UV LED strip 802 along with a translucent cover or lens 804. As illustrated, the UV light strip 802 includes a plurality of individual UV LEDs 806 received within a channel 808 defined by the translucent cover or lens 804.

Figure 9:
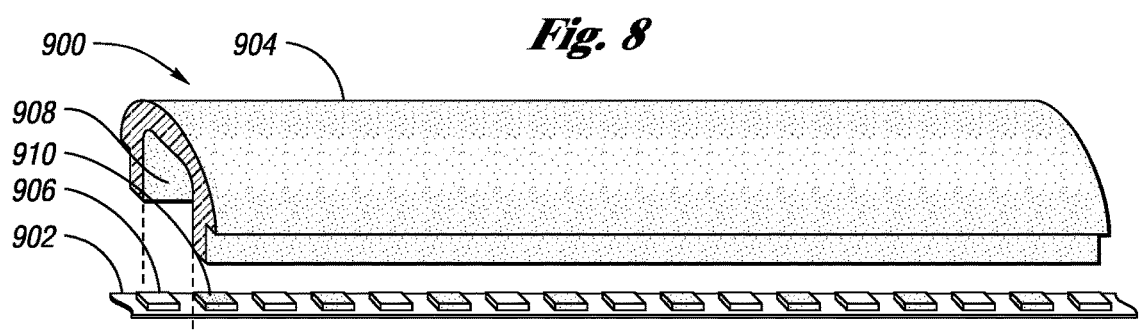
FIG. 9 illustrates an exploded perspective view of decorative RGB LED lighting used on gaming machines including alternating UV LED along with a translucent cover or lens to provide sterilization, disinfection and decontamination elements of the embodiments of the present invention.

FIG. 9 illustrates an exploded cross section perspective view of another embodiment of a decorative RGB-UV LED strip lighting assembly 900 used on gaming machines including a RGB-UV LED light strip 902 along with a translucent cover or lens 904. As illustrated, the RGB-UV LED light strip 902 includes a plurality of individual RGB LEDs 906 and a plurality of UV LEDs 910 which alternate on the RGB-UV LED strip 902 which is received within a channel 908 defined by the translucent cover or lens 904. Those skilled in the art will recognize that any convenient alternating spacing may be utilized such as every other LED is an UV LED, every third LED is an UV LED, or any similar alternating or spacing arrangement.

Figure 10:
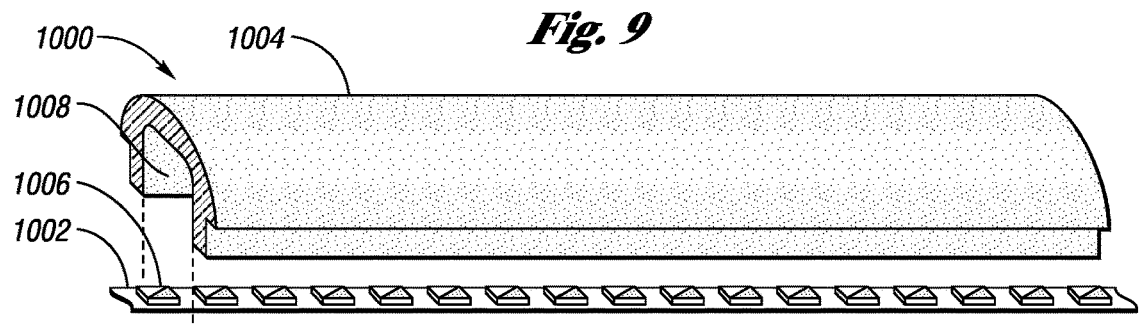
FIG. 10 illustrates an exploded perspective view of hybrid RGB-UV LED lighting used on gaming machines along with a translucent cover or lens to provide sterilization, disinfection and decontamination elements of the embodiments of the present invention.

FIG. 10 illustrates an exploded cross section perspective view of another embodiment of a decorative RGB-UV LED strip assembly 1000 used on gaming machines including a RGB-UV LED strip 1002 along with a translucent cover or lens 1004. As illustrated, the RGB-UV LED light strip 1002 includes a plurality of individual RGB-UV LEDs 1006 received within a channel 1008 defined by the translucent cover or lens 1004. One aspect of the embodiments of the present invention is the combining of a plurality of LEDs into one multi-wavelength RGB-UV LED.

Figure 11:
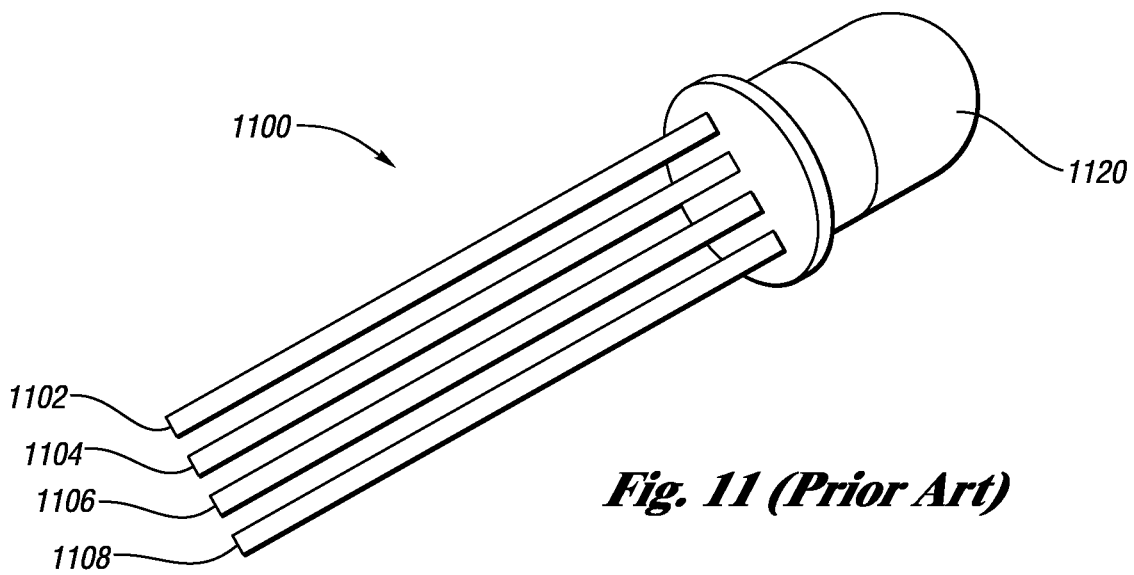
FIG. 11 illustrates a simplified perspective view of a prior art RGB LED including four pins.

FIG. 11 illustrates a simplified perspective view of a prior art RGB LED 1100 including four pins 1102, 1104, 1106 including one common pin 1108. As shown, pin 1102 is attached to a red LED, pin 1104 is attached to a green LED and pin 1106 is attached to a blue LED. Those skilled in the art will recognize that the sequence of pins can follow any order. Moreover, those skilled in the art will recognize that if two or more individual LED are always energized simultaneously in any embodiment, two or more of the separate pins may be combined into a second common pin. The various internal components of the RGB LED are then encapsulated within housing 1120. In addition, those skilled in the art will recognize that although a simplified view of a representative LED is illustrated, LEDs of the embodiments of the present invention may be fabricated in a very large variety of sizes and shapes which are known in LED manufacturing industries.

Figure 12:
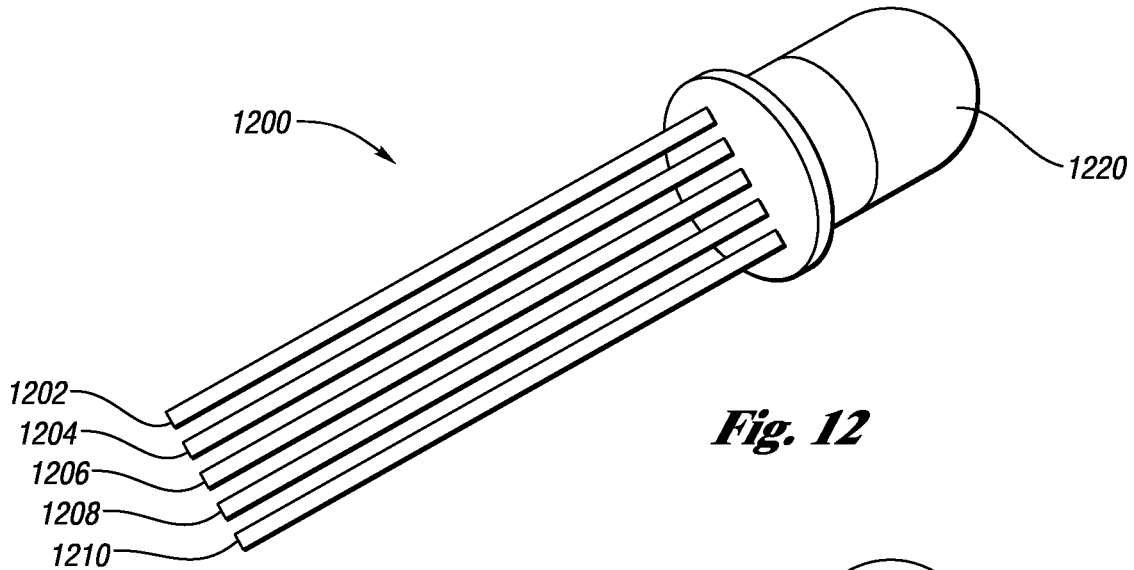
FIG. 12 illustrates a simplified perspective view one embodiment of the present invention including five pins capable of producing RGB-UV LED lighting including the production of UV radiation.

FIG. 12 illustrates a simplified perspective view of an embodiment of the present invention which is a RGB-UV LED. The RGB-UV LED 1200 includes five pins 1202, 1204, 1206, and 1208 along with one common pin 1210. As shown, pin 1202 is attached to a red LED, pin 1204 is attached to a green LED, pin 1206 is attached to a blue LED, and pin 1208 is attached to a UV LED. Those skilled in the art will recognize that the sequence of pins can follow any order. Moreover, those skilled in the art will recognize that if two or more individual LED are always energized simultaneously in any embodiment, two or more of the separate pins may be combined into a second common pin. The various internal components of the RGB LED are then encapsulated within housing 1220. In addition, those skilled in the art will recognize that although a simplified view of a representative LED is illustrated, LEDs of the embodiments of the present invention may be fabricated in a very large variety of sizes and shapes which are known in the LED manufacturing industries.

Figure 13:
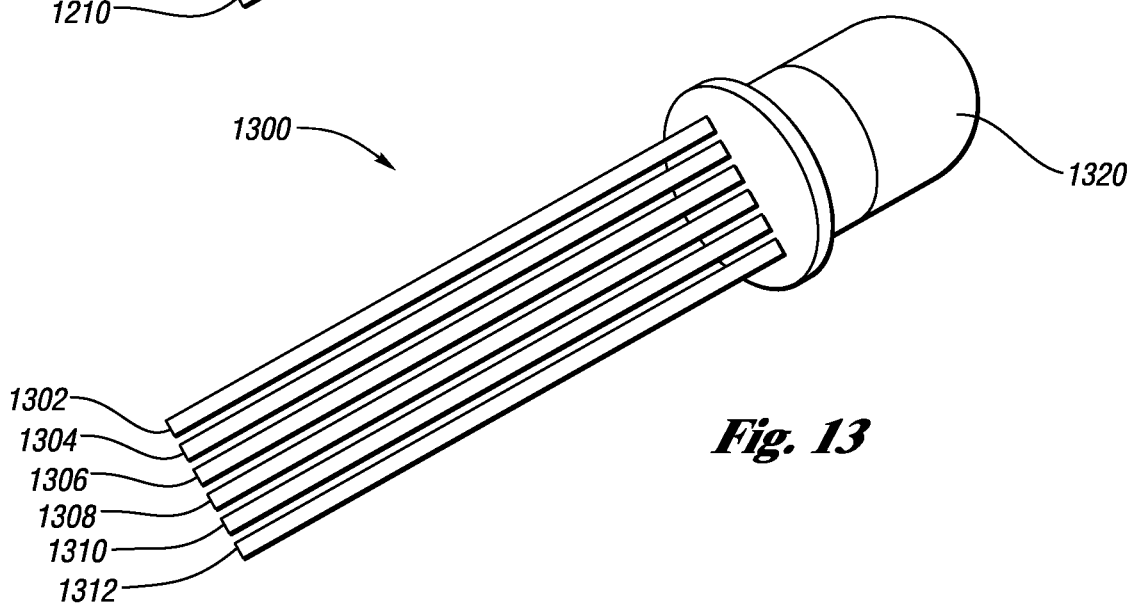
FIG. 13 illustrates a simplified perspective view one embodiment of the present invention including six pins capable of producing RGB-UV LED lighting including the production of UV radiation.

FIG. 13 illustrates a simplified perspective view of another embodiment of the present invention which is a RGB-UV LED with multiple wavelength UV LEDs. The RGB-UV LED 1300 includes six pins 1302, 1304, 1306, 1308, and 1310 along with one common pin 1312. Although this embodiment illustrates a RGB-UV LED with two separate UV wavelength LEDs, any number of differing wavelengths UV LEDs may be incorporated into the embodiments of the present invention. As shown pin 1302 is attached to a red LED, pin 1304 is attached to a green LED, pin 1306 is attached to a blue LED, pin 1308 in attached to one wavelength UV LED, and pin 1310 is attached to a different wavelength UV LED. Those skilled in the art will recognize that the sequence of pins can follow any order. Those skilled in the art will recognize that if two or more individual LED are always energized simultaneously in any embodiment, two or more of the separate pins may be combined into a second common pin. The various internal components of the RGB LED are then encapsulated within housing 1320. In addition, those skilled in the art will recognize that although a simplified view of a representative LED is illustrated, LEDs of the embodiments of the present invention may be fabricated in a very large variety of sizes and shapes which are known in the LED manufacturing industries. Those skilled in the art will recognize that in addition to the embodiments of FIG. 12 and FIG. 13, white LEDs can also be combined in a similar manner with one or more UV LEDs.

As set forth above, the strip lighting assemblies may be integral with a newly manufactured EGM or may be installed as a retrofit. When installed as a retrofit there are numerous methods for attaching the strip lighting assemblies. A first method involves replacing existing EGM lighting with the desired UV strip lighting assemblies including the UV radiation sources. With such a method, the existing translucent cover or lens (see, FIG. 6) is removed, and the existing EGM lighting is replaced with desired UV strip or RGB-UV strip lighting assemblies or one or more UV LED strip lighting assemblies may be installed adjacent to the existing EGM lighting. Alternatively, the desired UV strip lighting assemblies may be installed without accessing the existing EGM lighting. For example, the UV strip lighting assemblies may be adhered to the EGM using adhesive backing (or other means such as mechanical fasteners, extensions and/or hook and loop type fasteners commonly sold under the Velcro® brand) and then covered with a translucent cover or lens. In one embodiment, the UV strip lighting assemblies include the integral translucent cover and simply need to be adhered to the EGM and connected to a power source. The power source may be separate from the EGM or integral therewith. Those skilled in the art will recognize that the UV strip lighting assemblies may be attached to hardware which is then attached to the EGM. In other words, the UV light assemblies need not be attached to the EGM directly but may utilize intermediary hardware components such as the side panels shown in FIG. 4.

With these retrofit embodiments, it is a relatively simple task to position the UV strip lighting assemblies to radiate near the button deck, touch-screen display, bill validator, card reader and other peripherals associated with the EGM. Advantageously, lighting on EGMs is common such that the additional UV strip lighting assemblies can be positioned to blend in and interact with existing decorative EGM lighting so as not to unnecessarily raise player concerns or take away from the overall design of the EGM. The retrofit systems may be permanent or used as an interim solution until the EGMs may be completely overhauled to incorporate an integral UV lighting system.

In one embodiment, the UV strip lighting assemblies are passive in nature such that they are constantly in an on state. In another embodiment, the UV strip lighting assemblies may intermittingly cycle between an on state and an off state to control the amount of UV radiation received by the player. In another embodiment, the UV strip lighting is in an on state while no player is playing the EGM and in an off state when the EGM is being played. It is also conceivable that the state of the UV strip lighting assemblies may be premised on the EGM state of multiple adjacent EGMs or a bank of EGMs. In one embodiment, for example, when three neighboring EGMs are inactive, their respective UV strip lighting assemblies are in the on state whereas if any one of the three EGMs is being played, each of the respective UV strip lighting assemblies is in an off state. Such UV strip lighting may also be addressable by the processor to control function.

Regardless of the state operation of the UV strip lighting assemblies, the UV strip lighting assemblies may or may not be connected to the electronics of the EGM. In a first embodiment, the UV strip lighting assemblies may be controlled by the EGM's processor or other internal electronics. This is true for newly manufactured EGMs or more in-depth retrofits. With such an embodiment, the EGM state (i.e., being played or idle), determined by an inserted player card or operation of a play button, dictates the operation of the UV strip lighting assemblies. Alternatively, the UV strip lighting assemblies may be controlled by their own independent controller or processor. In one such embodiment, a sensor or similar article associated with the UV strip lighting assemblies is positioned to determine the EGM state. The sensor output thus dictates the state of the UV strip lighting assemblies. The processor or controller may be programmed to control the UV light source in any manner conceivable to kill the virus and protect the player from UV radiation. In one embodiment, a central processor (e.g., server) controls the UV light source for a plurality of EGMs to which it communicates.

In one embodiment, the UV strip lighting assemblies include UV LEDs of different strengths whereby less potent UV LEDs are in an on state when the EGM is being played and the more potent UV LEDs are only in an on state when the EGM is not being played.

To further protect players and persons nearby from any side effects associated with UV radiation exposure, the UV strip lighting assemblies may be outfitted with reflectors, deflectors and/or directors to focus or direct the UV radiation at the specific desired point of contact with the EGM such as the touch-screen display or button deck of the EGM which contains the various player inputs (e.g., play button, cash out button, etc.). In this manner, the UV radiation is not being unnecessarily transmitted into contact with the player.

In one embodiment, multiple EGMs or a bank of EGMs may share a common arrangement of UV strip lighting assemblies or other UV light sources. For example, a bank of EGMs may utilize a common arrangement of UV light sources hanging from signage associated with the bank of EGMs or otherwise positioned above the EGMs forming the bank. In one embodiment, the common arrangement of UV light sources may be raised and lowered relative to the bank of EGMs. The state of the common arrangement of UV light sources may be controlled in the same manner as detailed above. In one embodiment, different portions of the common arrangement of UV light sources may be in different states simultaneously. Those skilled in the art will recognize that any of the previously described functions or functionality may exist for either retrofit applications, new machine installations, or any combination thereof.

Figure 14:
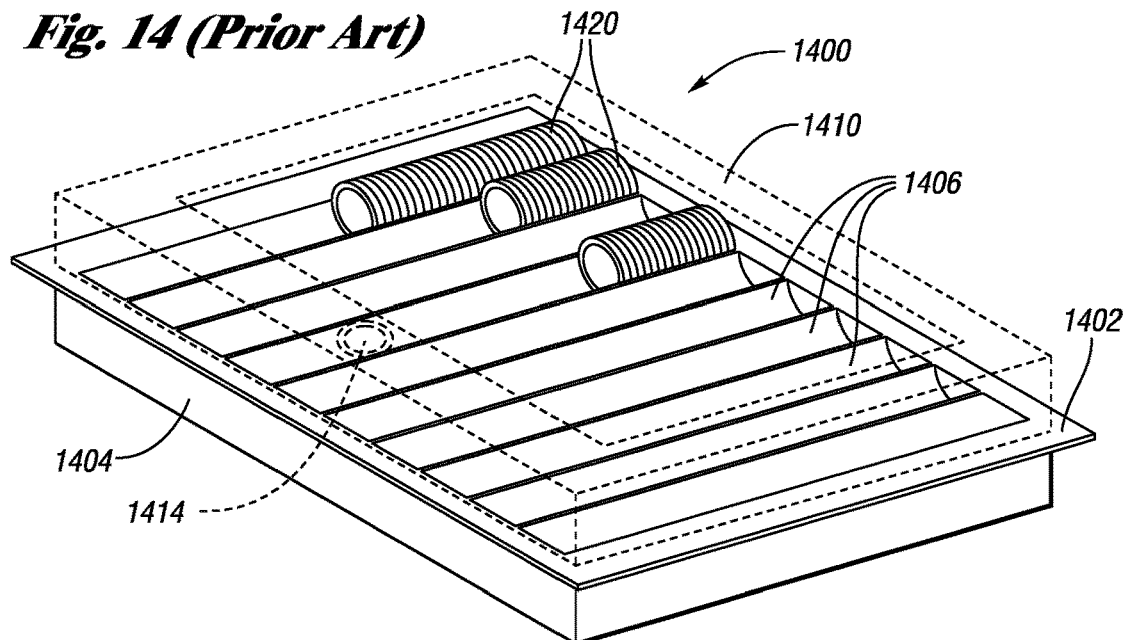
FIG. 14 illustrates a prior art chip tray that is commonplace on casino table games.

FIG. 14 illustrates an isometric view of a prior art gaming chip tray which are commonplace in the table games or "pit" section of casinos. As illustrated, gaming chip tray 1400 is generally rectangular in shape and often includes a flange 1402 which seats on the gaming table once the lower section 1404 is lowered into place. Gaming chip tray 1400 also includes a plurality of semi-circular profile recesses 1406 constructed to receive a plurality of gaming chips 1420. Also shown in broken line is the gaming chip tray cover 1410 which generally contains a lock 1414 to safeguard the gaming chips 1420 when a gaming table is not in use.

Figure 15:
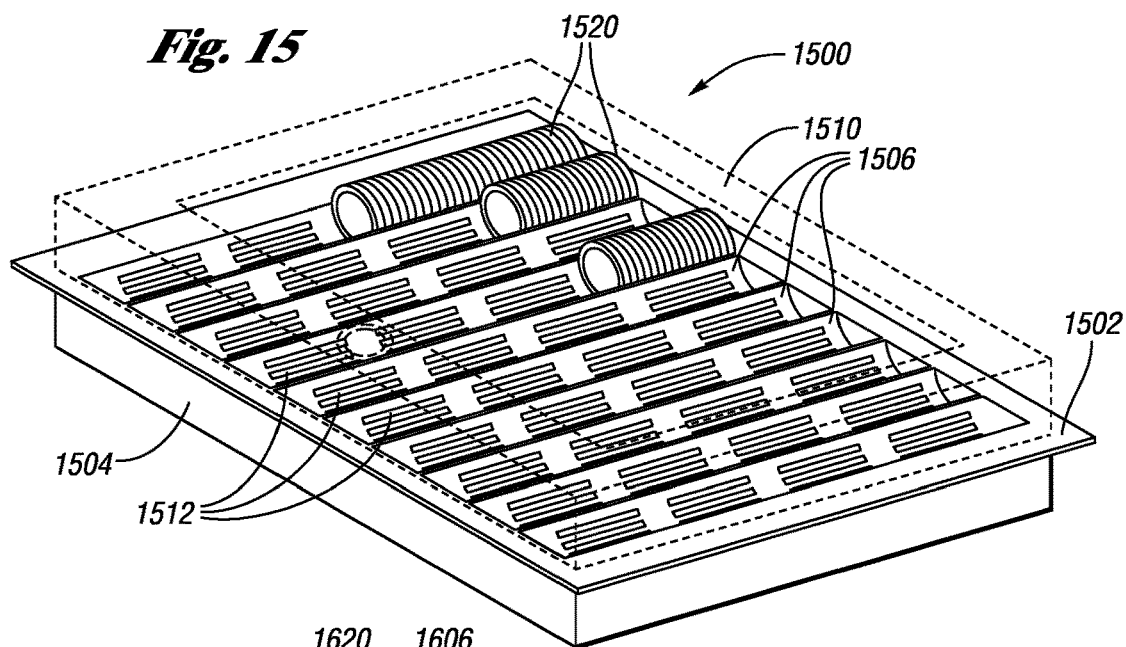
FIG. 15 illustrates a chip tray of the embodiments of the present invention which sterilizes, disinfects and decontaminates gaming chips while in use in a casino.

FIG. 15 illustrates an isometric view of gaming chip tray embodiment of the present invention. As illustrated, gaming chip tray 1500 is generally rectangular in shape and often includes a flange 1502 which seats on the gaming table once the lower section 1504 is lowered into place. Gaming chip tray 1500 includes a plurality of semi-circular profile recesses 1506 constructed to receive a plurality of gaming chips 1520. Also shown in broken line is the gaming chip tray cover 1510 which generally contains a lock 1514 to safeguard the gaming chips when a gaming table is not in use. As illustrated gaming chip tray 1500 includes a plurality of semi-circular profile recesses 1506 constructed to receive a plurality of gaming chips 1520 and within each of the plurality of semi-circular profile recesses 1506 is a plurality of openings 1512 that allow for the transmission of light or radiation to pass through from under the top portion of the gaming chip tray 1500. The plurality of openings 1512 may be open, may be transparent, may be translucent or similar. Those skilled in the art will recognize that the openings 1512 can be of many shapes as long as they provide a means of transmission. In addition, some materials may allow for the passage of UV radiation and as such, no openings may be required as long as the UV radiation can reach the gaming chips. During use, gaming chip tray 1500 will be filled with a variety of differing denomination gaming chips such as $1 chips, $5 chips, $25 chips, $100 chips, etc., arranged for easy counting in the event a dealer must pay a player once they have won a wager. As the table game progresses, the gaming chips routinely go out and then come back for placement in the gaming chip tray 1500 depending on the outcomes of wagering activities. Accordingly, the chips 1520 will be exposed to the UV radiation to the extent necessary to reduce or eliminate contamination form viruses and the like. Those familiar with the art will recognize that while the contamination of the gaming chips 1520 may only be slightly reduced or even not reduced on a particular placement, the repeated placement and replacement into the gaming chip tray 1500 may be additive to the overall decontamination of the gaming chips 1520. This repeated exposure of objects may occur in many embodiments of the present invention. Those skilled in the art will recognize that the embodiment illustrated is representative of many chip holding and handling devices such as roulette chippers, chip cleaners, and the like.

Figure 16:
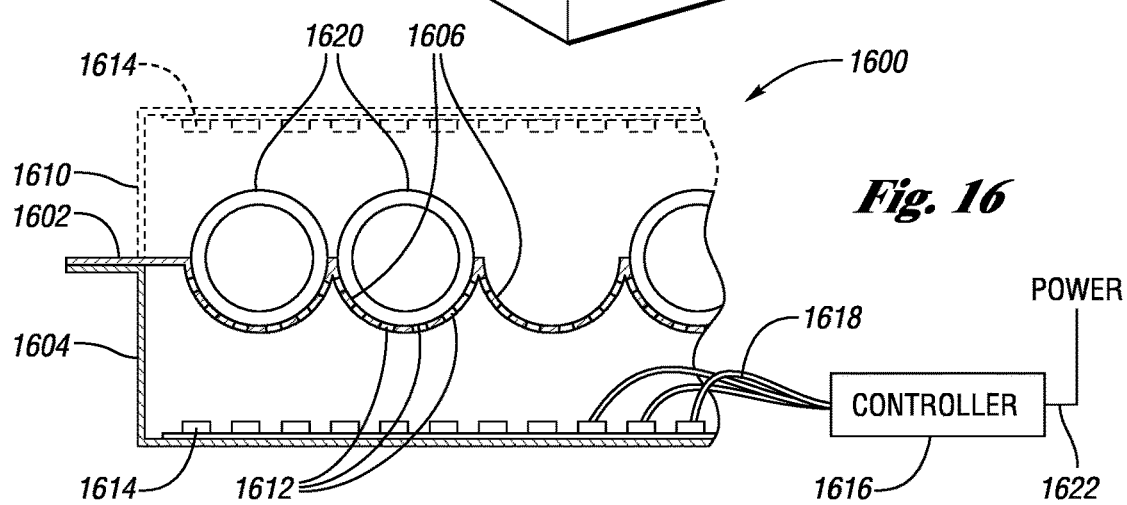
FIG. 16 illustrates a cross section of the chip tray of the embodiments of the present invention illustrated in FIG. 15 which sterilizes, disinfects and decontaminates gaming chips while in use in a casino.

FIG. 16 illustrates a partial cross section view of gaming chip tray embodiment of the present invention. As illustrated, gaming chip tray 1600 is generally rectangular in shape and often includes a flange 1602 which seats on the gaming table once the lower section 1604 is lowered into place. Gaming chip tray 1600 includes a plurality of semi-circular profile recesses 1606 constructed to receive a plurality of gaming chips 1620. As illustrated gaming chip tray 1600 includes a plurality of semi-circular profile recesses 1606 constructed to receive a plurality of gaming chips 1620 and within each of the plurality of semi-circular profile recesses 1606 is a plurality of openings 1612 that allow for the transmission of light or radiation to pass through from under the top portion of the gaming chip tray 1600. Those skilled in the art will recognize that the openings 1612 can be of many shapes as long as they provide a means of transmission. In addition, some materials may allow for the passage of UV radiation and as such, no openings may be required as long as the UV radiation can reach the gaming chips. During use, gaming chip tray 1600 will be filled with a variety of differing denomination gaming chips such as a $1 chips, $5 chips, $25 chips, $100 chips, etc., arranged for easy counting in the event a dealer must pay a player once they have won a wager. As the table game progresses, the gaming chips routinely go out and then come back for placement in the gaming chip tray 1600 depending on the outcomes of wagering activities. Accordingly, the chips will be exposed to the UV radiation to the extent necessary to reduce or eliminate contamination form viruses and the like. As illustrated, a series of UV or RGB-UV LEDs 1614 are located beneath the upper chip holding section of the gaming chip tray 1600. Placement is such that the UV radiation is allowed to pass through the openings 1612 and radiate the gaming chips, thereby reducing or eliminating the contamination of the gaming chips. Those familiar with the art will recognize that while the contamination of the gaming chips 1620 may only be slightly reduced or even not reduced on a particular placement, the repeated placement and replacement into the gaming chip tray 1600 may be additive to the overall decontamination of the gaming chips 1620. This repeated exposure of objects may occur in many embodiments of the present invention. The series of UV or RGB-UV LEDs 1614 which are located beneath the upper chip holding section of the gaming chip tray 1600 are controlled by controller 1616, as schematically shown, which includes a power supply 1622. As illustrated, the location if the series of UV or RGB-UV LEDs 1614 may also be located above the gaming chip tray 1600 on the underside of cover 1610 as shown in broken line. When this is the case, the gaming chips are decontaminated when the cover is closed or in applications where distribution may be automatically controlled.

Figure 17:
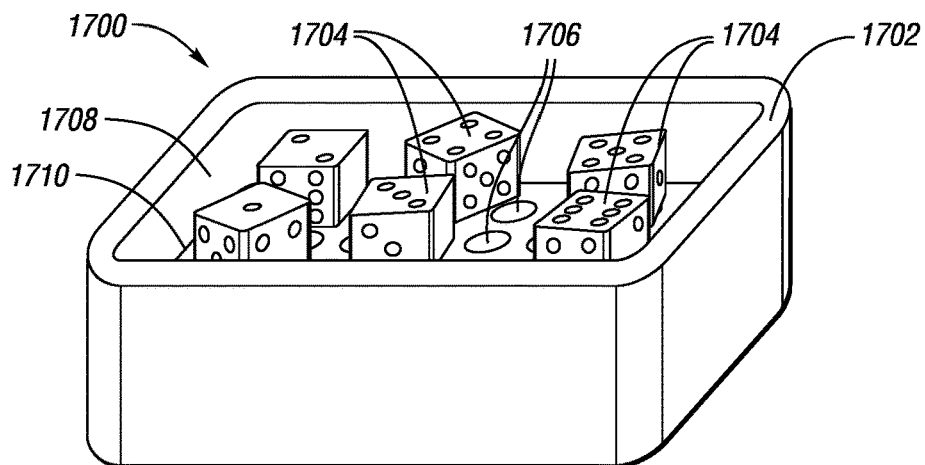
FIG. 17 illustrates an isometric view of a dice holding device embodiment of the present invention which sterilizes, disinfects and decontaminates dice while in use in a casino.

FIG. 17 illustrates an isometric view of a dice holding device embodiment 1700 of the present invention which sterilizes, disinfects and decontaminates dice while in use in a casino. As illustrated the dice holding device housing 1702 includes a rectangular opening 1708 which receives a plurality of dice 1704 which sit on the bottom structure 1710 which includes a plurality of openings 1706. Those skilled in the art will recognize that dice holding device 1700 may also include a cover or lockable cover (not shown). The plurality of openings 1706 are provided to allow for the passage of UV radiation which sterilize, disinfect and decontaminate the dice 1704. Those skilled in the art will recognize that the openings 1706 can be of many shapes as long as they provide a means of transmission of the UV radiation. In addition, some materials may allow for the passage of UV radiation and as such, no openings may be required as long as the UV radiation can reach the gaming dice. Those familiar with the art will recognize that while the contamination of the dice 1704 may only be slightly reduced or even not reduced on a particular placement, the repeated placement and replacement into the dice holding device 1700 may be additive to the overall decontamination of the dice 1704. This repeated exposure of objects may occur in any embodiments of the present invention. The dice holding device 1700 may be permanently mounted to a gaming table, such as a craps table or similar or movable as long movable placement allows for a power supply and controller, if needed.

Figure 18:
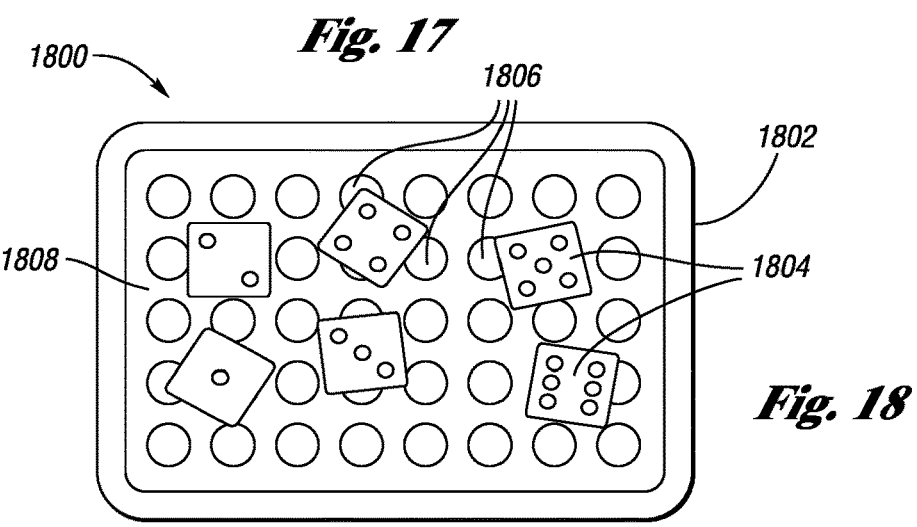
FIG. 18 illustrates a top plan view of the dice holding device embodiment of the present invention as illustrated in FIG. 17 which sterilizes, disinfects and decontaminates dice while in use in a casino.

FIG. 18 illustrates a top plan view of a dice holding device embodiment 1800 of the present invention which sterilize, disinfect and decontaminates dice while in use in a casino. As illustrated the dice holding device housing 1802 includes a generally rectangular opening 1808 which receives a plurality of dice 1804 which sit on the bottom structure 1810 which includes a plurality of openings 1806. The plurality of openings 1806 are provided to allow for the passage of UV radiation which sterilize, disinfect and decontaminate the dice 1804. Those skilled in the art will recognize that the openings 1806 or openings in any embodiment can be of many shapes or materials as long as they provide a means of transmission of the UV radiation. In addition, some materials may allow for the passage of UV radiation and as such, no openings may be required as long as the UV radiation can reach the gaming dice. Those familiar with the art will recognize that while the contamination of the dice 1804 may only be slightly reduced or even not reduced on a particular placement, the repeated placement and replacement into the dice holding device 1800 may be additive to the overall decontamination of the dice 1804. This repeated exposure of objects may occur in any embodiments of the present invention. The dice holding device embodiment 1800 may be permanently mounted to a gaming table, such as a craps table or similar or movable as long as movable placement allows for a power supply and controller, if needed.

Figure 19:
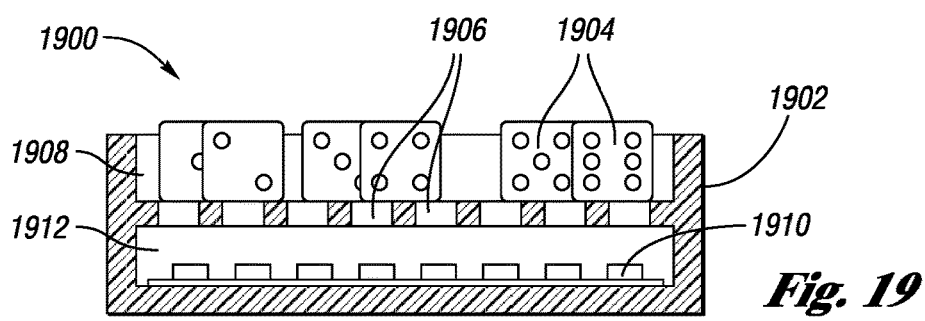
FIG. 19 illustrates a cross section view of dice holding device embodiment of the present invention as illustrated in FIG. 17 which sterilizes, disinfects and decontaminates dice while in use in a casino.

FIG. 19 illustrates cross section view of a dice holding device embodiment 1900 of the present invention which sterilize, disinfect and decontaminates dice while in use in a casino. As illustrated the dice holding device housing 1902 includes a rectangular opening 1908 which receives a plurality of dice 1904 which sit on the bottom structure 1910 which includes a plurality of openings 1906. The plurality of openings 1906 are provided to allow for the passage of UV radiation which sterilize, disinfect and decontaminate the dice 1904. Those skilled in the art will recognize that the openings 1906 can be of many shapes as long as they provide a means of transmission of the UV radiation provided by UV or RGB-UV LEDs 1910 which are located in the opening 1912. In addition, some materials may allow for the passage of UV radiation and as such, no openings may be required as long as the UV radiation can reach the gaming dice. Those familiar with the art will recognize that while the contamination of the dice 1904 may only be slightly reduced or even not reduced on a particular placement, the repeated placement and replacement into the dice holding device 1900 may be additive to the overall decontamination of the dice 1904. This repeated exposure of objects may occur in any embodiments of the present invention. The dice holding device 1900 may be permanently mounted to a gaming table, such as a craps table or similar or movable as long as movable placement allows for a power supply and controller, if needed.

Figure 20:
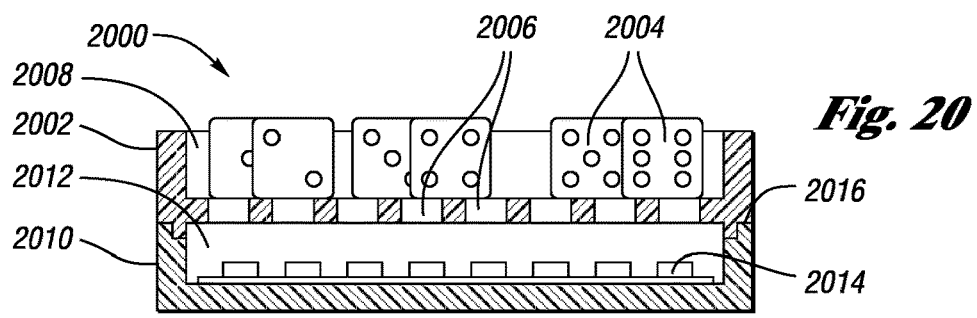
FIG. 20 illustrates another dice holding device embodiment of the present invention which sterilizes, disinfects and decontaminates dice while in use in a casino.

FIG. 20 illustrates cross section view of another dice holding device 2000 of the present invention which sterilize, disinfect and decontaminates dice while in use in a casino. As illustrated the dice holding device housing 2002 has a two-piece construction and includes a rectangular opening 2008 which receives a plurality of dice 2004 which sit on the bottom structure 2010 which includes a plurality of openings 2006. These structures in turn are mounted to a bottom section 2010 which interlocks with the top section 2002 through the step relationship of the construction 2016. The plurality of openings 2006 are provided to allow for the passage of UV radiation which sterilize, disinfect and decontaminate the dice 2004. Those skilled in the art will recognize that the openings 2006 can be of many shapes as long as they provide a means of transmission of the UV radiation provided by UV or RGB-UV LEDs 2014 which are located in the opening 2012. In addition, some materials may allow for the passage of UV radiation and as such, no openings may be required as long as the UV radiation can reach the gaming dice. Those familiar with the art will recognize that while the contamination of the dice 2004 may only be slightly reduced or even not reduced on a particular placement, the repeated placement and replacement into the dice holding device 2000 may be additive to the overall decontamination of the dice 2004. This repeated exposure of objects may occur in any embodiments of the present invention. The dice holding device embodiment 2000 may be permanently mounted to a gaming table, such as a craps table or similar or movable as long as movable placement allows for a power supply and controller, if needed. In addition, the upper portion 2002 which holds the dice 2004 is removable and can be passed to a dealer or player separately from the lower base portion 2010.

Figure 21:
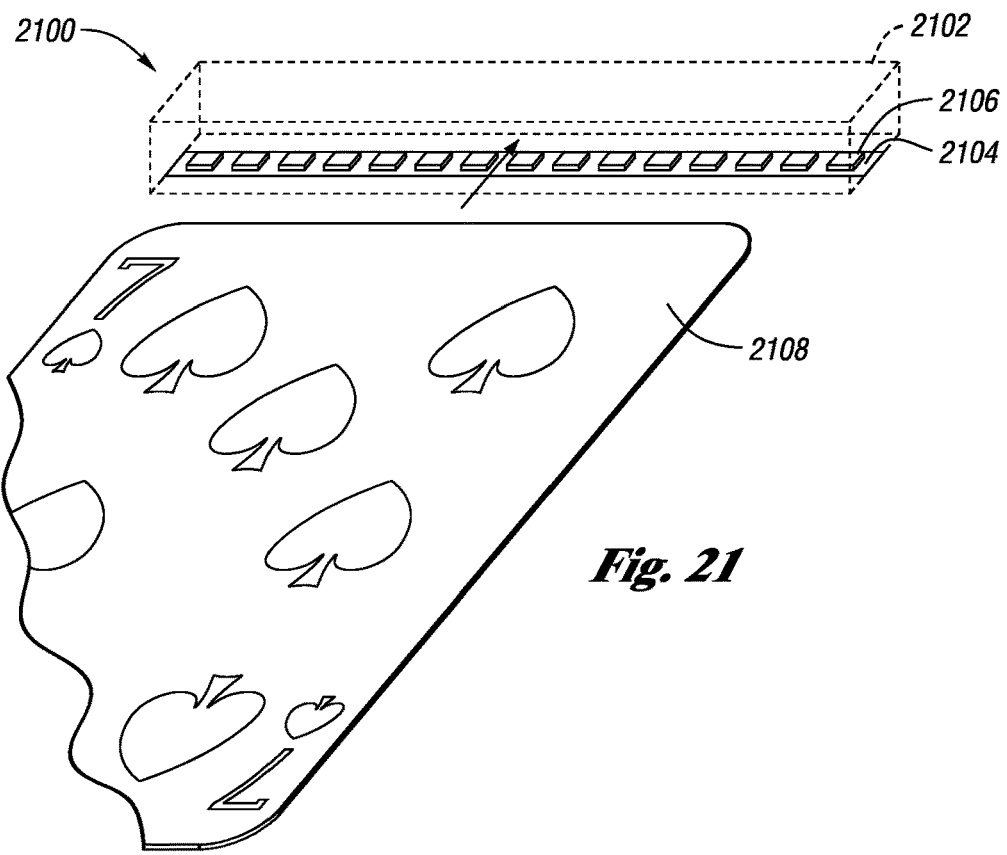
FIG. 21 illustrates a pass-through sterilization, disinfection and decontamination station embodiment used for playing cards and the like which is incorporated into an automatic card shuffler, an automatic playing card shoe, and similar devices.

FIG. 21 illustrates a pass-through sterilization, disinfection and decontamination station embodiment used for playing cards and the like which may be incorporated into an automatic card shuffler, an automatic playing card shoe, and similar devices. As illustrated, the pass-through sterilization, disinfection and decontamination station 2100 includes a housing 2102 shown in broken line which houses an LED strips 2104 located on one plane, the LED strip 2104 includes a plurality of UV or RGB-UV LEDs 2106. In operation, playing cards 2108 pass through the pass-through sterilization, disinfection and decontamination station to reduce or eliminate viruses and the like. Those skilled in the art will recognize that any of the pass-through sterilization, disinfection and decontamination station embodiments may be utilized to sterilize, disinfect and decontaminate any infected or potentially infected object.

Figure 22:
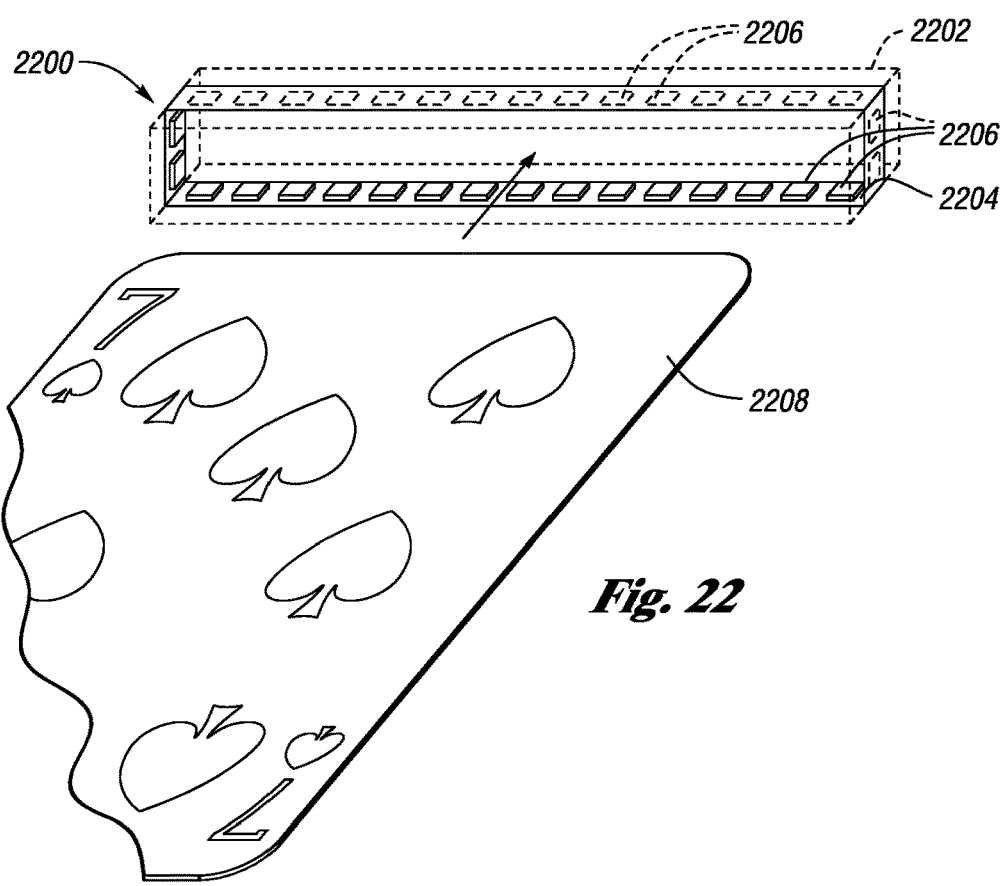
FIG. 22 illustrates another pass-through sterilization, disinfection and decontamination station embodiment used for playing cards and the like which is incorporated into an automatic card shuffler, an automatic playing card shoes, and similar devices.

FIG. 22 illustrates another pass-through sterilization, disinfection and decontamination station embodiment used for playing cards and the like which may be incorporated into an automatic card shuffler, an automatic playing card shoe, and similar devices. As illustrated, the pass-through sterilization, disinfection and decontamination station 2200 includes a housing 2202 shown in broken line which houses LED strips 2204 located on multiple planes, each with a plurality of UV or RGB-UV LEDs 2206. In operation, playing cards 2208 pass through the pass-through sterilization, disinfection and decontamination station to reduce or eliminate viruses and the like.

Figure 23:
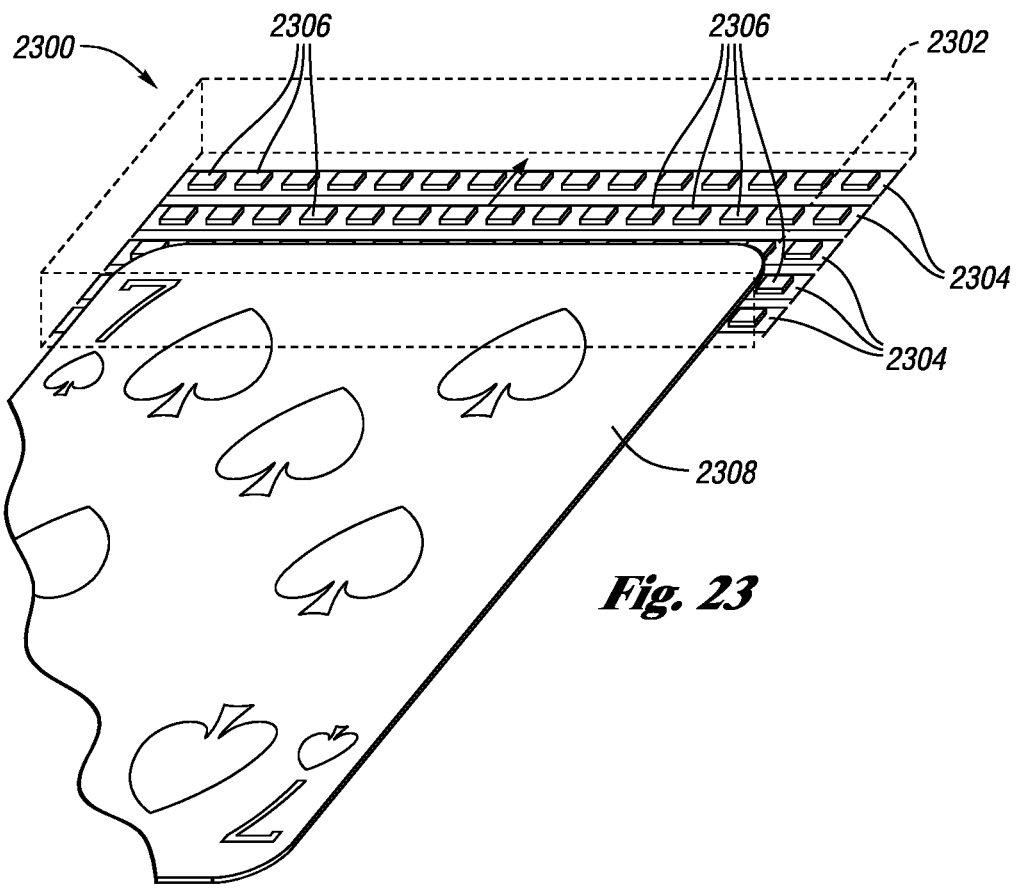
FIG. 23 illustrates another pass-through sterilization, disinfection and decontamination station embodiment used for playing cards and the like which is incorporated into an automatic card shuffler, an automatic playing card shoe, and similar devices.

FIG. 23 illustrates another pass-through sterilization, disinfection and decontamination station embodiment used for playing cards and the like which may be incorporated into an automatic card shuffler, an automatic playing card shoe, and similar devices. As illustrated, the pass-through sterilization, disinfection and decontamination station 2300 includes a housing 2302 shown in broken line which housed a plurality of LED strips 2304 located on one plane, each with a plurality of UV or RGB-UV LEDs 2306. In this embodiment, the LED strips 2304 are placed side-by-side. In operation, playing cards 2308 pass through the pass-through sterilization, disinfection and decontamination station to reduce or eliminate viruses and the like.

Figure 24:
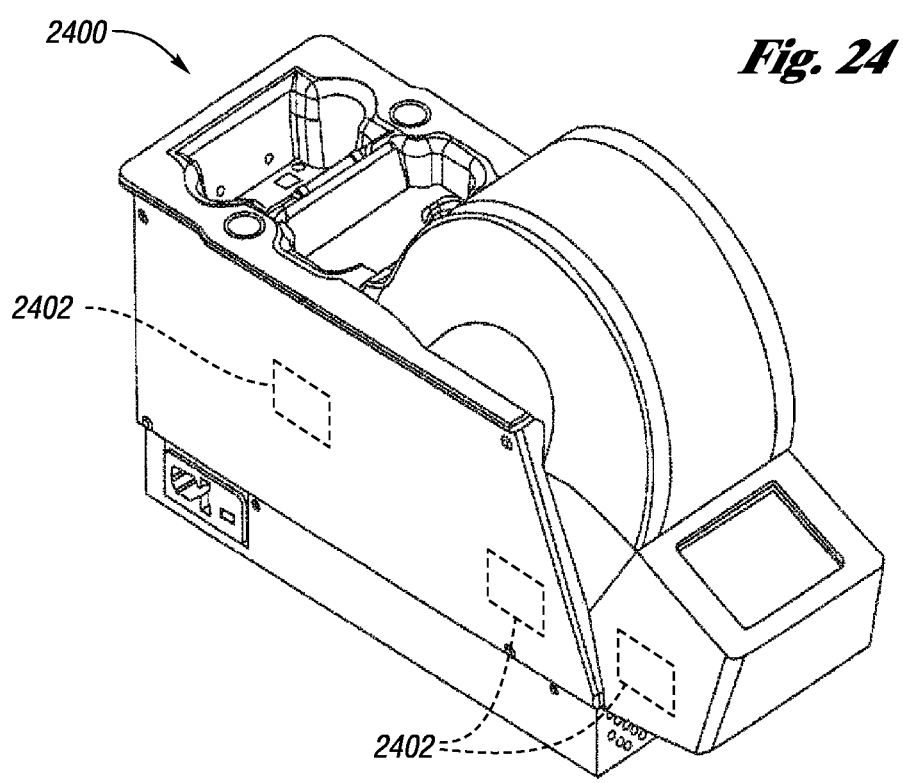
FIG. 24 illustrates a typical prior art automatic playing card shuffler of which there are many types and styles.

FIG. 24 illustrates a typical prior art automatic playing card shuffler 2400 of which there are many types and styles, includes mechanisms for playing card distribution such as manual or automatic playing cards shoes. As shown in broken line, a pass-through sterilization, disinfection and decontamination station or stations may be located in any convenient and effective location 2402 within the automatic playing card shuffler 2400.

Figure 25:
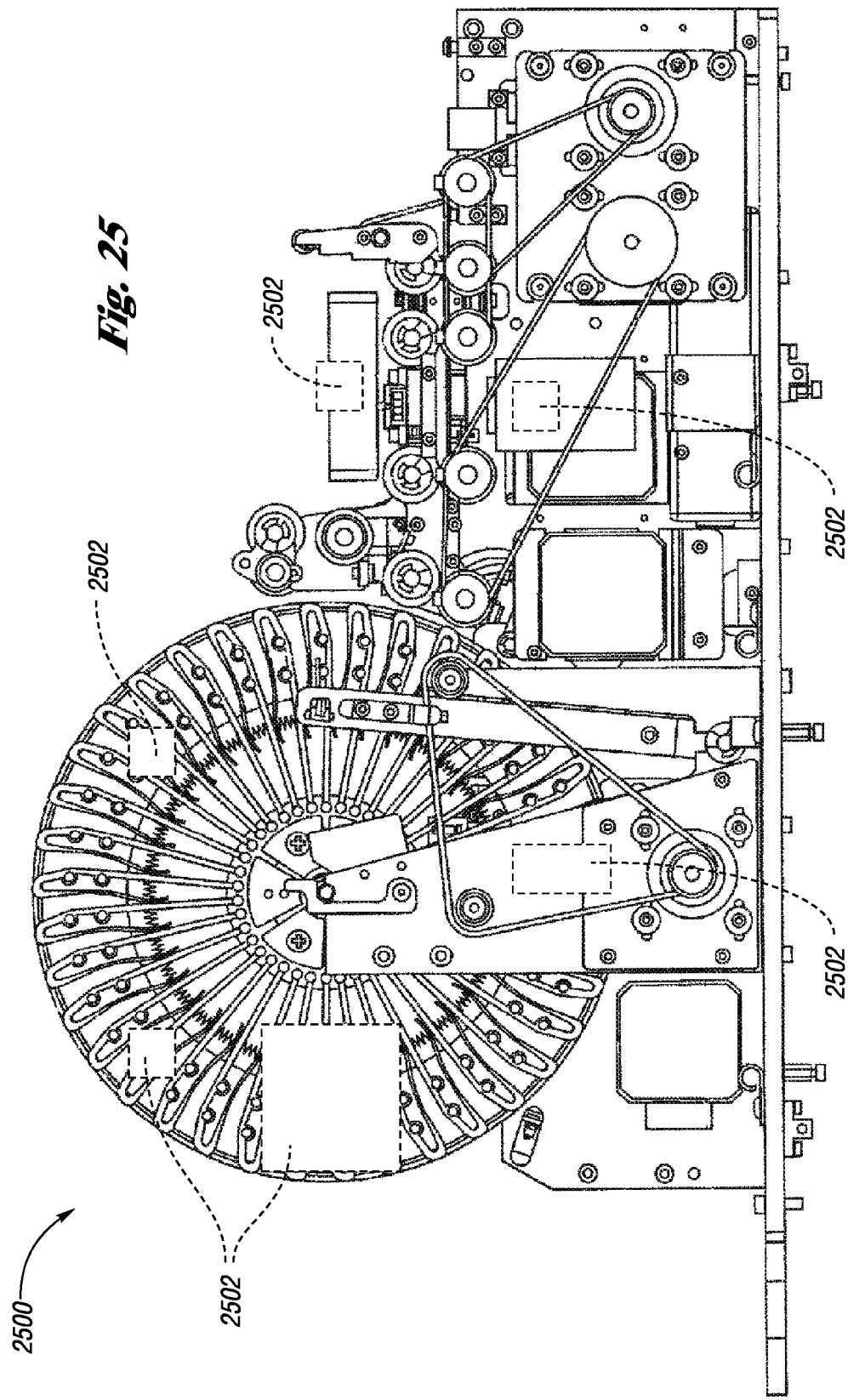
FIG. 25 illustrates side elevational view a typical prior art automatic playing card shuffler with the cover or housing removed, of which there are many types and styles.

FIG. 25 illustrates side elevational view a typical prior art automatic playing card shuffler 2500 with the cover or housing removed, of which there are many types and styles. As illustrated with broken lines, pass-through sterilization, disinfection and decontamination station(s) may be located in any convenient area of the playing card shuffler 2500. Those skilled in the art will recognize that some redesign of any device incorporating a pass-through sterilization, disinfection and decontamination station embodiment may be necessary to allow for the pass-through sterilization, disinfection and decontamination stations 2502. In this embodiment, either the rectangular opening pass-through sterilization and decontamination station(s) or a single or plurality of planar sterilization, disinfection and decontamination station(s), similar to that illustrated in FIG. 23, may be utilized. In many scenarios, it is possible to irradiate the entire or a large portion of the interior of such mechanisms for maximum effectiveness.

While automatic playing card shufflers have been described in detail, the same principles and scope apply to currency counting devices, automatic teller machines, etc., whereas, instead of playing cards being processed, currency is processed. Similarly, other gaming devices or peripheral devices may also be equipped with embodiments of the present invention. These devices include but are not limited to magnetic card reads, TITO printers, bill validators, etc.

While many of the embodiments set forth above detail the use of openings allowing the passage of UV radiation to contact the objects (e.g., chips, dice and cards) to be sterilized and decontaminated, those skilled in the art will recognize that the openings may be replaced with, or modified to, include translucent materials, such as glass and/or plexiglass, that permit the passage of UV radiation. By way of example, the plurality of openings 1512 shown in the chip tray 1500 of FIG. 15 may be covered with a translucent material or more appropriately the semi-circular profile recesses 1506 may be constructed of a translucent material obviating the need for separate openings 1512. Alternatively, the translucent material may also incorporate openings.

In one embodiment, the button deck buttons and other EGM features may be fabricated of translucent materials which allow the passage of UV light such that the UV light sources may be built into or installed into the button deck housing. In this manner, the sterilization, disinfection and/or decontamination of the buttons and other EGM features is done from within the EGM as opposed to via attachments of the sterilization, disinfection and decontamination mechanisms 150 on the external surface of the EGM cabinet or deck.

Figure 26:
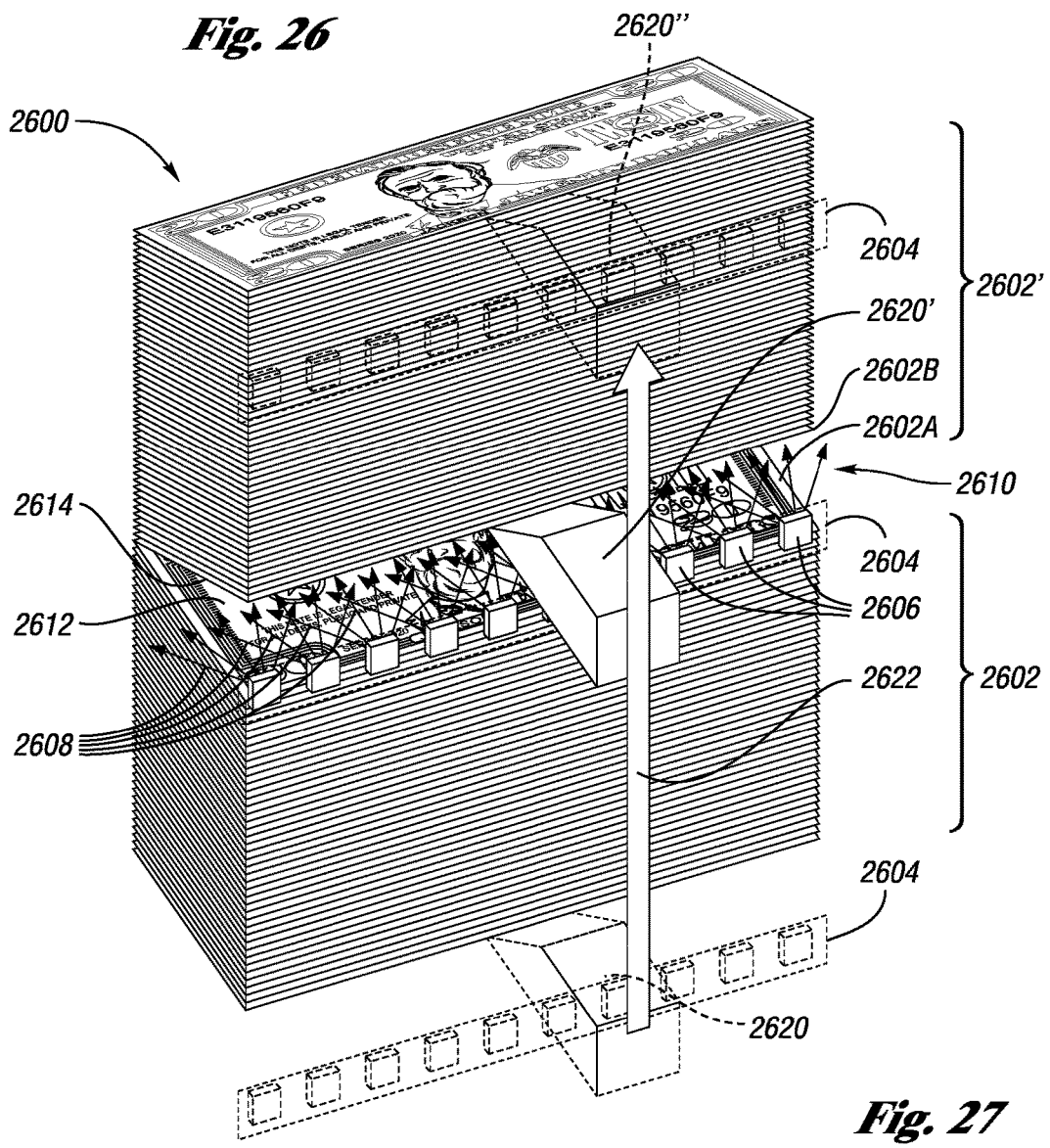
FIG. 26 illustrates a stack separator mechanism according to the embodiments of the present invention.

FIG. 26 illustrates a stack separator mechanism 2600 according to embodiments of the present invention which separates stacked items such as currency 2602 or similar items such as playing cards, gaming chips, or the like in devices and mechanisms such as automatic teller machines, EGM bill acceptors, currency counting machines, card shufflers, gaming chip trays, playing card shoes, manual or automated table games cash drop boxes, and the like. Generally, items are stacked on top of one another as shown in currency stack 2602. Those skilled in the art will recognize the stacked items need not be stacked vertically as items may be stacked horizontally or in any convenient angular relationship. Stacked items may limit or prohibit the effective use the embodiments of the present invention as there is little or no room between stacked items resulting in the inability for UV radiation to reach the top or bottom surfaces of the stacked items such as currency 2602, playing cards, or the like. The stack separator mechanism 2600 provides for on opening between stacked items 2602 and 2602' (and 2602") that allows for the UV radiation to reach the top surface 2612 and bottom surface 2614 of the stacked items 2602 via use of a stack separator block 2620. Typically, the stack separator block 2620 will move in a parallel fashion with the stacked items 2602, starting from the bottom of the stacked items 2602. Those skilled in the art will recognize that the stack separator block 2620 may be movable in any convenient direction as long as it results in adequate separation of the stacked items. As shown, a stack separator block 2620 starts at the bottom of stacked items 2602 and is placed slightly under the stacked items 2602. As the stack separator block 2620' moves upwardly as shown by direction arrow 2622, it incrementally lifts the stacked items 2602' upwardly to provide a separation 2610, revealing surfaces 2612 and 2614. The separation 2610 allows for UV radiation 2608, provided by UV LED strip 2604 and UV LEDs 2606, to reach surfaces 2612 and 2614. The UV strip 2604 and UV LEDs 2606 may move with stack separator block 2620 or remain stationary. In a stationary embodiment, a plurality of LED strips 2604 may be employed to allow for a more complete exposure to the UV radiation. As the stack separator block moves, it may move upwardly just enough to release the top stacked item 2602A therefore providing a new separation 2610 for the stacked item 2602B directly above the previous stacked item 2602A. Movement of stack separator block 2620, may be incremental or indexed where the stack separator block 2620 moves a distance to reveal the next set of separated items and then stop to allow for prolonged exposure to the UV radiation 2608. Preferably the movement distance is about that of the item or currency thickness. Alternatively, stack separator block may have continuous movement from bottom to top, retract, return to the original bottom location and extend and then repeat as often as desired, similar to paging through a book, over and over. Accordingly, utilizing the stack separator mechanism 2600 will allow for sterilization, disinfecting and decontaminating of the entire stack of items, either partially or fully. Those skilled in the art will recognize that while a mechanical mechanism is illustrated, similar separating means such as utilizing air pressure mechanisms, rollers, stacker wheels, etc., may be employed to provide similar separation of stacked items.

Figure 27:
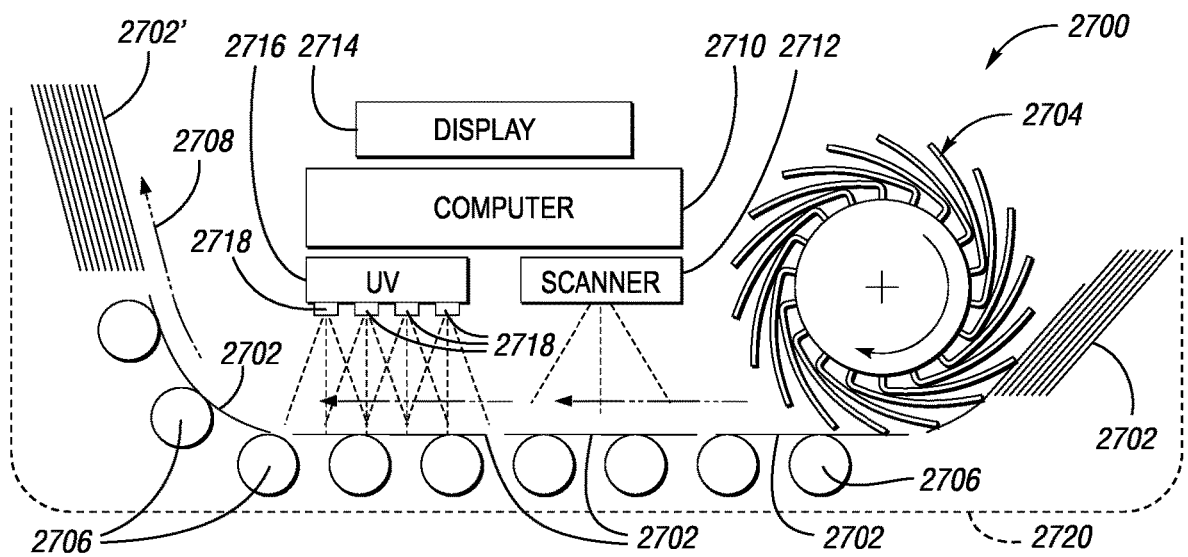
FIG. 27 illustrates a schematic side view of a currency counting device according to the embodiments of the present invention.

FIG. 27 illustrates a schematic side view of a currency counting device 2700 embodiment of the present invention. Currency is loaded as a stack of currency 2702. During operation, stacker wheel 2704 rotates to pull the top item into the currency counting device 2700. The currency items 2702 then proceed individually through the various stations of currency counting device 2700 as shown by arrows 2708 through use of rollers 2706 or similar means as schematically illustrated. As the items moves through the currency counting device 2700, it is scanned by scanner 2712 to determine the currency denomination, number of items, determination of counterfeit items, etc. Scanner 2712 is controlled by computer 2710 which also operates display 2714 which may show total dollar amount, number of currency items, number of counterfeit items (if applicable), etc. Computer 2710 may also be in communication with additional computers for accounting and other purposes. As the currency item proceeds through the currency counting device 2700, it is exposed to the UV radiation station 2716 and UV LEDs 2718 for sterilization, disinfecting and decontaminating. Typically, the UV radiations station will expose little or no radiation outside of the currency counting device 2700 as it is contained within housing 2720 allowing for increased intensity for more rapid processing. Following scanning and UV radiation, the currency items will leave the processing and transfer area of the currency counting device 2700 and be stacked as shown 2702'. Those skilled in the art will recognize that the sequence of stations or operations may be in any convenient order. Moreover, those skilled in the art will recognize that the principles of the various UV sterilization, disinfecting and decontaminating embodiments may apply to any type or design currency counting device.

Figure 28:
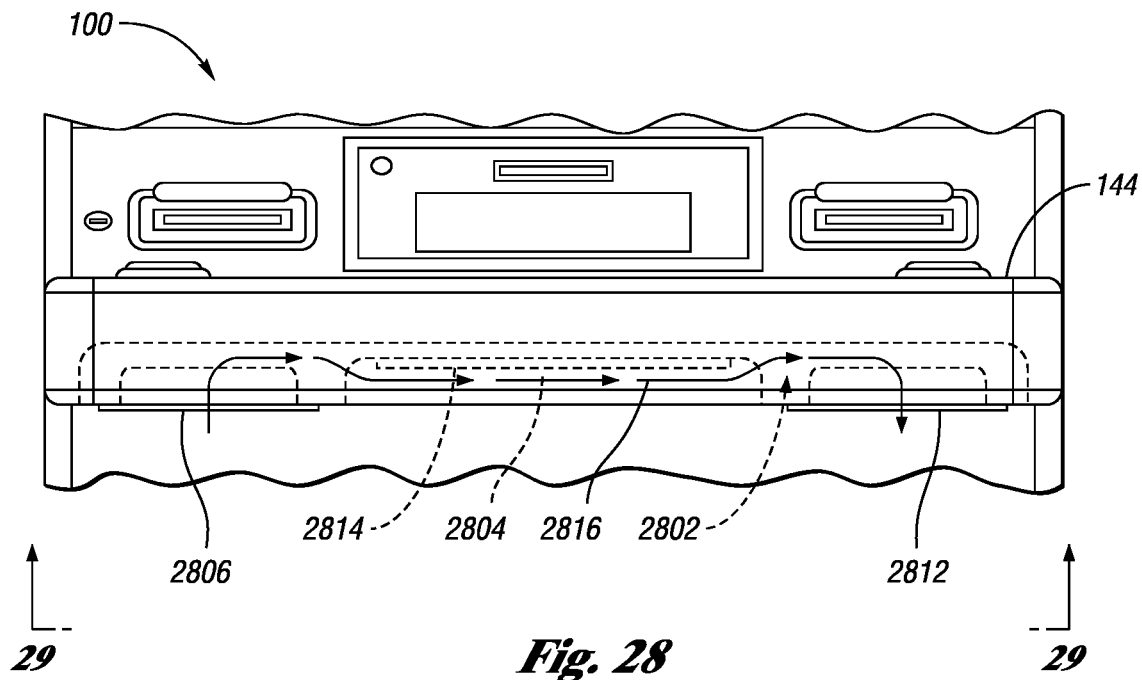
FIG. 28 illustrates a front elevation view of the button deck area of the EGM of FIG. 1 with an air purification system according to the embodiments of the present invention.

FIG. 28 illustrates a broken away front elevation view of the button deck area of the EGM of FIG. 1 with another embodiment of the present invention incorporating an UV air purification system 2802. As illustrated, preferably the UV air purification system 2802 is located below the button deck 144 of the EGM 100. The UV air purification system 2802 includes an air purification chamber 2804 within UV air purification system 2802. Within the air purification chamber 2804, one or more UV lighting elements 2814 are located. Air is brought into the air purification chamber 2804 via intake 2806 and then treated in air purification chamber 2804 and then forced out via the exhaust mechanism 2812, after processing as illustrated by air flow arrows 2816. The UV air purification system 2802 may operate at all times, may be operator controlled or timed via the EGM administrative settings, or turned on or off by a player, for example. Those skilled in the art will recognize that while two separate fans are illustrated in FIG. 28, a single individual fan may also be utilized to serve both intake and exhaust functions. Those skilled in the art will recognize that while the UV air purification system 2802 is illustrated as located underneath the button deck 144, it may be located in other areas of the EGM 100 such as the lower support structure of the EGM 100, above the display or any other convenient location.

Figure 29:
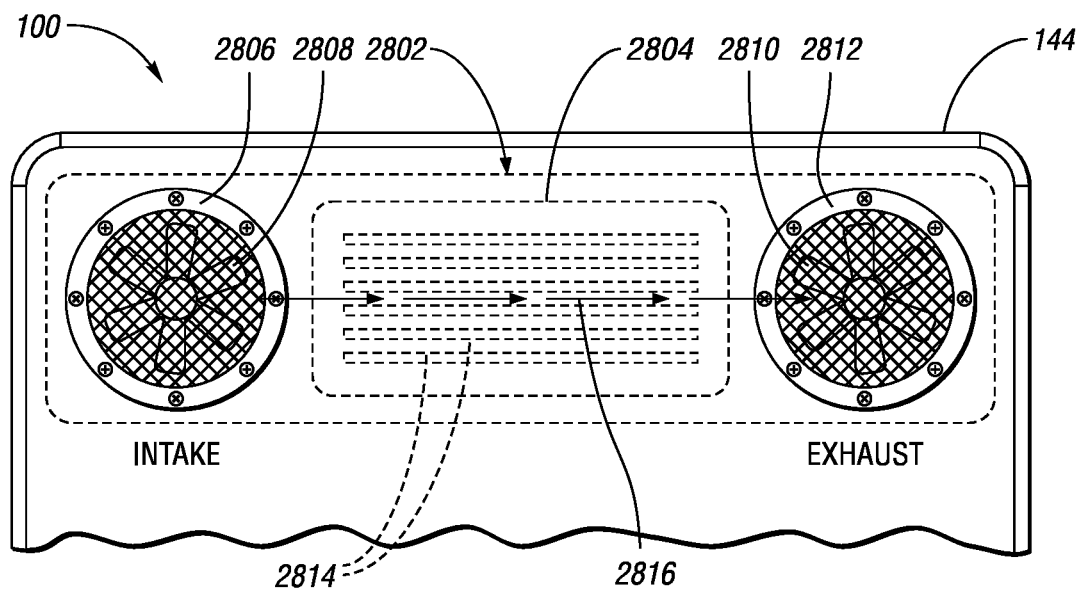
FIG. 29 illustrates a bottom plan view of the EGM of FIG. 1 with an air purification system according to the embodiments of the present invention.

FIG. 29 illustrates a partial bottom plan view of the button deck area of the EGM 100 of FIG. 1 with incorporating an UV air purification system 2802. As illustrated, the UV air purification system 2802 may be located below the button deck 144 of the EGM 100. The UV air purification system 2802 includes an air purification chamber 2804 within UV air purification system 2802. Within the air purification chamber 2804, one or more UV lighting elements 2814 are located. Air is brought into the air purification chamber 2804 via intake 2806 via fan 2808 and treated in air purification chamber 2804 and then forced out via the fan 2810 of exhaust mechanism 2812, after processing as illustrated by air flow arrows 2816. The UV air purification system 2802 may operate at all times, may be operator controlled or timed via the EGM administrative settings, or turned on or off by a player. Those skilled in the art will recognize that while two separate fans are illustrated in FIG. 28, an individual fan may also be utilized to serve both intake and exhaust functions. Those skilled in the art will recognize that while the UV air purification system 2802 is illustrated as located underneath the button deck 144, it may be located in other areas of the EGM 100 such as the lower support structure of the EGM 100, above the display or any other convenient location.

In another embodiment, the UV air purification system 2602 may incorporate a filter near exhaust mechanism 2612. In one embodiment, the filter is saturated with one or more agents (e.g., alcohol, sanitizer, etc.) known to reduce or kill viruses of the type the system herein is designed to control. For example, the air leaving the UV air purification system 2602 must pass through the filter before or after encountering fan 2610. In one embodiment, the blades of the fan 2610 may incorporate saturated filters for reducing or killing viruses.

Figure 30:
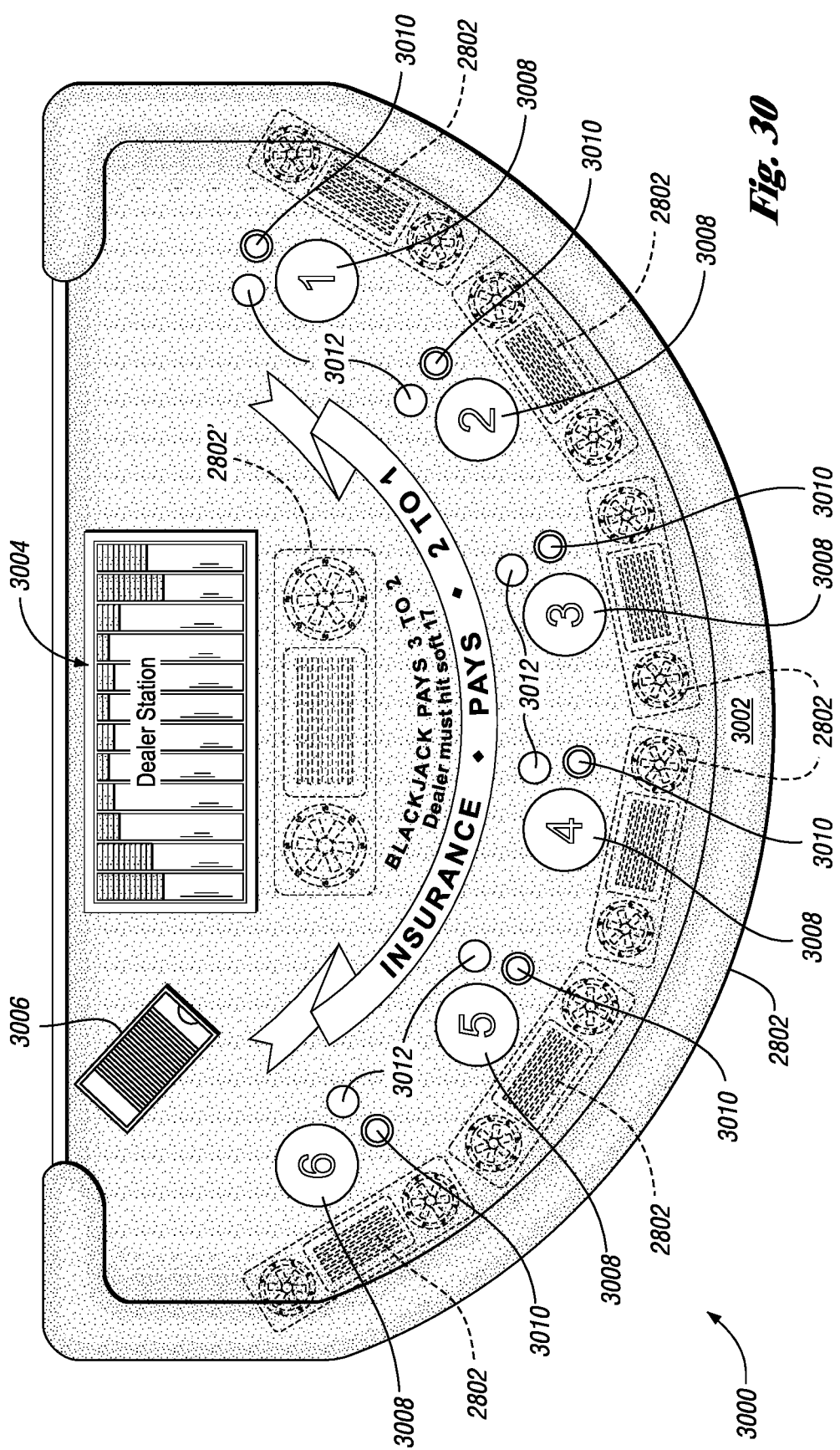
FIG. 30 illustrates a top plan view of an exemplar table game incorporating an UVC air purification system according to the embodiments of the present invention.

FIG. 30 illustrates a top plan view of an exemplar table game 3000 incorporating an UVC air purification system 2802. Those familiar with the art will recognize that although a typical blackjack table game is illustrated, similar embodiments of the present invention are adaptable to any type or style of table games including but not limited to craps, roulette, Pai Gow, poker, three card poker, big six wheel, baccarat, etc. As illustrated, the UVC air purification system 2802 may be located below the table in any convenient location either for new installations or in a retrofit model. As the UVC air purification units are low profile, e.g., relative thin in height, they will present little chance to be accidentally bumped by a player's knees or the like. Objects of these embodiments of the present invention are similar to those objects previously described for EGMs. Similarly, electronic table games (ETG) will also adapt well to the UVC air purification systems. Those skilled in the art will recognize that while EGMs have been described in detail, ETGs are essentially a sub-category of EGMs.

Blackjack table 3002 includes table top layout customized for the game of blackjack 3000, a chip rack 3004 wherein gaming chips are stored and distributed, a playing card dispenser, otherwise known as a dealer shoe 3006. The layout presented includes six player gaming positions or betting spots 3008. However, those skilled in the art will recognize that an alternative number of players may be utilized in blackjack games and the other table games or game layouts have little in common with the game of blackjack yet embodiments of the present invention are adaptable in the same or similar manner to all such table games. For each gaming position, a number of betting positions are offered including the main betting spots 3008, a side bet position 3012 and/or electronic betting positions 3010 which electronically track player bets. As illustrated, each player gaming position includes a UVC air purification system 2802 and an additional UVC air purification system 2802' located closer to the dealer. Those skilled in the art will recognize that any number of UVC air purification systems 2802 may produce the desired results to various degrees. For example, smaller more compact UVC air purification systems 2802 may be incorporated at each player gaming position or in the alternative, the UVC air purification systems 2802 may be spaced at a every other player gaming position or even utilize a larger UVC air purification system 2802' which is capable of processing larger volumes of air purification in which case one or two UVC air purification systems 2802' may suffice. Any of the UVC air purification systems 2802 may also optionally incorporate one or more air filters, such as polyester and pleated filters, high efficiency particulate arrestance (HEPA) filters, electrostatic filters, washable air filters, etc., to aid in reducing cigarette smoke or other particulates.

Figure 31:
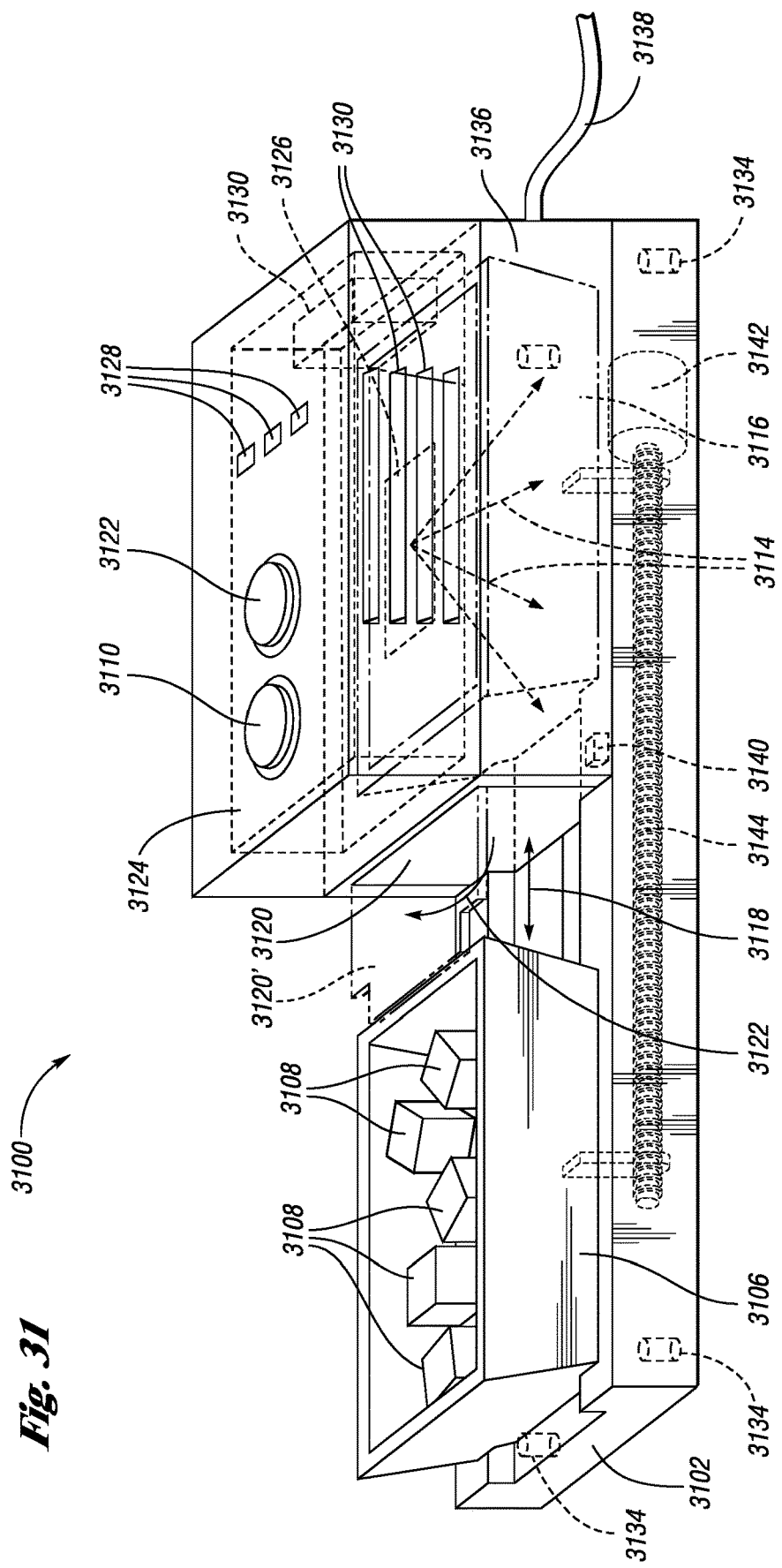
FIG. 31 illustrates a perspective view of an automated dice UVC disinfecting unit according to the embodiments of the present invention.

FIG. 31 illustrates a perspective view of an automated dice UVC disinfecting unit 3100 embodiment of the present invention. In general use, the automated dice UVC disinfecting unit may sit on top of a craps table layout, usually comprises of a printed felt or similar synthetic material, or may be affixed to a sidewall of the craps table or even reside outside of the craps table on any suitable support structure such as a table or the like. Mechanical fastening means such as drilled and tapped threaded holes 3134 may be provided to permanently affix the automated dice UVC disinfecting unit 3100 to an associated support structure. In some cases, the automated dice UVC disinfecting unit 3100 may be placed at the supervisory podium of a floor person who supervises a pit which contains a number of differing casino table games. In such cases, one automated dice UVC disinfecting unit may serve to disinfect the dice used in multiple craps tables. Automated dice UVC disinfecting unit includes a base portion 3102 that sits on top of the craps table or the like and includes a slideway 3104 that engages a slideable dice cradle 3106 which holds the dice 3108 before, during and after the disinfection process. Traditionally, many casinos will utilize a single sleeve of dice during the game which contains five separate dice but in practice, any number of dice may be used as long as they fit within the dice cradle 3106. To help ensure proper and smooth slide characteristics of the mechanism a dovetail type slideway may be employed or other suitable mechanisms such as a square slideway, one or more linear bearings, precision sliding fit rods, keyways or the like.

During operation, the dice 3108 and placed into the dice cradle 3108 and the start button 3110 is pressed to begin the UVC disinfection process and operation. Dice cradle 3108 moves along the slideway by means of a mechanical mechanism such as a drive motor 3142 and lead screw 3144 mechanically linked to the dice cradle 3108 (schematically illustrated). Those skilled in the art will recognize that many mechanisms such as gear drive, belt drive, pneumatic, electromagnetic drives, etc. may also accomplish moving the dice cradle 3108 along the slideway 3104. Following disinfection or to interrupt the disinfection operation, a push button 3112 is provided whereas the UVC light source 3114 is turned off. Alternatively, the operation may be more fully automated where a sensor is provided to detect when the dice are loaded into the dice cradle 3106 whereas the dice cradle 3106 automatically moves into the UVC chamber 3116. When the disinfection process ends, based on time and/or intensity, the dice cradle 3106 is moved out of the UVC chamber 3116 and into the original load/unload position. The longitudinal movement of the dice cradle 3106 in and out of the UVC chamber 3116 is indicated by arrow 3118. The dice cradle may be constructed with quartz or a quartz bottom portion that cooperates with a second UVC light source under the dice cradle 3106. Although quartz may be described in this embodiment of the present invention, other materials may also be effective as they possess UV transparency characteristics such as polymers like acrylic and silicone, ceramics, fused silica, specialized UV glass compositions, or similar. Those skilled in the art will recognize that any embodiment of the present invention that requires or may benefit from UVC light sources below a supporting structure or similar can utilize such a transparent UV material for the support structure.

The automated dice UVC disinfecting unit 3100 includes a door 3120 that opens for the longitudinal movement of the dice cradle 3106. In the loading or starting position the door swings open from its normally closed position on an arcuate path shown by arrow 3122. The arcuate movement may be controlled by use of a spring, such as an extension spring or similar, or motorized by use of an electronically controlled servo motor or the like. Those skilled in the art will recognize that there are many alternatives to the arcuate swinging door such as vertical travel or the like. Not only does the door 3120 open to allow the dice cradle 3106 to travel to or from the UVC chamber 3116, it acts to seal the UVC chamber 3116 so little or no UVC radiation exits the automated dice UVC disinfecting unit 3100. A mechanical, magnetic, electronic, or similar interlock 3140 is provided to ensure that the door 3120 is in the closed position prior to energizing the UVC light source. The maximum escaping UVC radiation for the automated dice UVC disinfecting unit 3100 may be dictated by FDA maximum human exposure times. Those skilled in the art will recognize that UV or UVC radiation and UV or UVC light are used interchangeably herein. In addition, those skilled in the art will recognize that other light outside of the UV range may also be beneficial in the disinfection process for any embodiments of the present invention. For example, lighting in the 405 nm range may provide some disinfecting properties, they also provide visible blue light to indicate that the disinfecting process is underway, reassuring the public that the disinfected objects are relatively safe to use or at least partially disinfected.

The automated dice UVC disinfecting unit 3100 includes a UVC distribution module 3124 that contains the UVC light producing means 3126 which may utilize UVC LEDs, UVC lamps, UVC excimer lamps or the like, including any future means for producing UVC radiation. Differing operational characteristics, cost, efficiency, life expectancy, etc., may dictate which lamp type is best suited for any embodiment of the present invention. Accordingly, any embodiment of the present invention illustrated or described herein may, in many cases, utilize differing UVC light sources than those shown. Different operational states are indicated by LED indicators 3128. These states may include on, off, disinfecting, lamp failure, jammed dice cradle, etc. Alternatively, a PCB may be provided with a LED or LCD display capable of displaying any applicable information to the operator. As UVC light producing means 3126 may generate excessive heat, one or more fans 3130 may be provided to dissipate heat produced. Assisting in this regard are a plurality of vents 3132 that allow the heat to vent from the automated dice UVC disinfecting unit 3100. Located under the UVC distribution module 3124 is the UVC chamber housing 3136 which accepts the dice cradle 3106 during the disinfection process and which supports the door 3120. The UVC chamber housing is mounted to the base portion 3102 below and supports the UVC distribution module 3124 above. Power for the automated dice UVC disinfecting unit 3100 is supplied using a wired power connection 3138.

FIG. 32 illustrates a perspective view of an automated dice boat UVC disinfecting unit embodiment of the present invention 3200. The term "dice boat" originates from a conventional dice holding tray that is commonly utilized for craps and other dice table games. Generally, a "dice boat" is a semicircular open tray which holds a plurality of dice during game play. This embodiment of the present invention emulates a conventional "dice boat" in overall shape and size so that players and/or dealers may be more comfortable with the configuration of the device.

Automated dice boat UVC disinfecting unit 3200 includes a housing 3202, an upper housing portion 3204, and lower housing 3206. Located between the upper housing 3204 and lower housing 3206 is a rotatable dice tray 3208 which receives dice 3224 (not shown in this figure) for disinfection when the dice tray 3208 is in the closed position. Rotatable dice tray 3208 rotates about the axis 3219 of shaft 3218. To assist in a smoother operation, shaft 3218 may be supported by bearing or bushings. Operational buttons 3210 and 3112 are provided and may be assigned different tasks such as, start, stop, interrupt, etc. Also provided is a display 3214 which provides operation information to the user such as disinfecting on, disinfecting off, disinfecting complete, dice tray open, dice tray locked, unit jammed, elapsed time of use, need for service, etc. Any of the embodiments of the present invention may also employ such a display. The display may be a LCD, LED, OLED, or the like.

FIG. 33 illustrates a perspective view of an automated dice boat UVC disinfecting unit embodiment of the present invention shown in a loading/unloading position. Automated dice boat UVC disinfecting unit 3200 includes a housing 3202, an upper housing portion 3204, and lower housing 3206. Located between the upper housing 3204 and lower housing 3206 is a rotatable dice tray 3208 which receives dice 3224 for disinfection when the dice tray 3208 is in the closed position. Rotatable dice tray 3208 rotates about the axis 3219 of shaft 3218 as illustrated by arcuate path 3226. To assist in a smoother operation, shaft 3218 may be supported by bearing or bushings. Operational buttons 3210 and 3112 are provided and may be assigned different tasks such as, start, stop, interrupt, etc. Also provided is a display 3214 which provides operation information to the user such as disinfecting on, disinfecting off, disinfecting complete, dice tray open, dice tray locked, unit jammed, elapsed time of use, need for service, etc. Any of the embodiments of the present invention may also employ such a display. The display may be a LCD, LED, OLED, or the like. A first array of UVC LEDs 3220 are located within upper housing 3204 and a second array of UVC LEDs 3222 are located within lower housing 3206. As illustrated, dice tray 3208 is preferably constructed with a quartz or similar UV transparent material 3209 that allows for transmission of the UV light from the bottom to more effectively treat all surfaces of the objects to be disinfected. In this and similar embodiments of the present invention, only the bottom of the dice tray 3208 would be UV transmissive so as to contain the UV light within UVC chamber 3211. Conversely, for this and all embodiments of the present invention, non-transmissive materials may be incorporated to ensure little or no UV radiation passes through components which may be harmful to humans or to certain other materials. To ensure that little or no light escapes from the automated dice boat UVC disinfecting unit 3200, a first mechanical, magnetic, electronic, or similar interlock device cooperates with a second mechanical, magnetic, electronic, or similar interlock device 3228 is provided to ensure that the dice tray 3208 is in the closed position prior to energizing the UVC light source. The maximum escaping UVC radiation for the automated dice boat UVC disinfecting unit 3200 may be dictated by FDA maximum human exposure times.

During operation, the dice 3224 are placed into the rotatable dice tray 3208 and the start button 3210 is pressed to begin the UVC disinfection process and operation. Dice tray 3208 rotates about axis 3219 along the rotatable path 3226 until it is in the closed and interlocked position. Those skilled in the art will recognize that while this embodiment of the present invention illustrated automatically opens and closes, similar movement and functions can be achieved by manual mechanical means. Similarly, any embodiment of the present invention that includes automated opening and closing mechanisms may also utilize a manual mechanism alternative.

Once the dice tray 3208 is in the closed and interlocked position, the UVC LEDs may be energized via push button 3210 to provide for the UVC disinfecting radiation. Alternatively, the operation may be more fully automated where a sensor is provided to detect when the dice are loaded into the dice tray 3208 whereas the dice tray 3208 automatically moves into the UVC chamber 3211. The cycle time for the disinfecting of the dice 3224 is generally based on time and/or intensity to ensure that at least a portion of the dice have been disinfected. Once the dice have been at least partially disinfected, the dice tray 3208 of the automated dice boat UVC disinfecting unit 3200 opens and returns to the load/unload position as shown in FIG. 4. Once opened, the disinfected dice 3224 can then be used in service for the game.

FIG. 34 illustrates a top plan view of an automated dice boat UVC disinfecting unit embodiment of the present invention shown in a loading/unloading position. As illustrated, automated dice boat UVC disinfecting unit 3200 includes a housing 3202, an upper housing portion 3204, and lower housing 3206. Located between the upper housing 3204 and lower housing 3206 is a rotatable dice tray 3208 which receives dice 3224 for disinfection when the dice tray 3208 is in the closed position. Rotatable dice tray 3208 rotates about shaft 3218 as illustrated by arcuate path 3226. To assist in a smoother operation, shaft 3218 may be supported by bearing or bushings. Operational buttons 3210 and 3112 are provided and may be assigned different tasks such as, start, stop, interrupt, etc. Also provided is a display 3214 which provides operation information to the user such as disinfecting on, disinfecting off, disinfecting complete, dice tray open, dice tray locked, unit jammed, elapsed time of use, need for service, etc. Any of the embodiments of the present invention may also employ such a display. The display may be a LCD, LED, OLED, or the like. A first array of UVC LEDs 3220 are located within upper housing 3204 and a second array of UVC LEDs 3222 are located within lower housing 3206. As illustrated, dice tray 3208 is preferably constructed with a quartz or similar UV transparent material bottom 3209 that allows for transmission of the UV light from the bottom to more effectively treat all surfaces of the objects to be disinfected. In this and similar embodiments of the present invention, only the bottom 3209 of the dice tray 3208 would be UV transmissive so as to contain the UV light within UVC chamber 3211. To ensure that little or no light escapes from the automated dice boat UVC disinfecting unit 3200, a first mechanical, magnetic, electronic, or similar interlock device cooperates with a second mechanical, magnetic, electronic, or similar interlock device 3228 is provided to ensure that the door 3120 is in the closed position prior to energizing the UVC light source. The maximum escaping UVC radiation for the automated dice boat UVC disinfecting unit 3200 may be dictated by FDA maximum human exposure times.

During operation, the dice are placed into the rotatable dice tray 3208 and the start button 3210 is pressed to begin the UVC disinfection process and operation. Servo motor 3232 is engaged to rotate shaft 3234 which in turn drives drive belt 3236 which in turn drives shaft 3218 which is connected to the dice tray 3208 and move the dice tray into the closed position. When the disinfection process ends or the stop button 3512 is pressed or similar condition, the opposite occurs and the dice tray 3208 moves into the load/unload position. Dice tray 3208 rotates about axis 3219 along the rotatable path 3226 until it is in the closed and interlocked position. Those skilled in the art will recognize that while this embodiment of the present invention illustrated automatically opens and closes, similar movement and functions can be achieved by manual mechanical means. Similarly, any embodiment of the present invention that includes automated opening and closing mechanisms or other automated features may also utilize manual mechanism alternatives. Moreover, those skilled in the art will recognize that while mechanical, magnetic or electronic interlocks are illustrated in many embodiments of the present invention, similar interlock may be achieved by mechanical or electromechanical means utilizing latches, springs, pins, microswitches, etc.

Once the dice tray 3208 is in the closed and interlocked position, the UVC LEDs may be energized via push button 3210 to provide for the UVC disinfecting radiation. Alternatively, the operation may be more fully automated where a sensor is provided to detect when the dice are loaded into the dice tray 3208 whereas the dice tray 3208 automatically moves into the UVC chamber 3211. The cycle time for the disinfecting of the dice is generally based on time and/or intensity to ensure that at least a portion of the dice have been disinfected. Once the dice have been at least partially disinfected or the stop button pressed, the dice tray 3208 of the automated dice boat UVC disinfecting unit 3200 opens and returns to the load/unload position as shown in broken line. Once opened, the disinfected dice can then be used in service for the game.

FIG. 35 illustrates a perspective view of an automated dice boat UVC disinfecting unit embodiment of the present invention 3500. The term "dice boat" originates from a conventional dice holding tray that is commonly utilized for craps and other dice table games. Generally, a "dice boat" is a semicircular open tray which holds a plurality of dice during game play. This embodiment of the present invention emulates a conventional "dice boat" in overall shape and size so that players and/or dealers may be more comfortable with the configuration of the device.

Automated dice boat UVC disinfecting unit 3500 includes a housing 3502, an upper housing portion 3504, and lower housing 3506. Located between the upper housing 3504 and lower housing 3506 is a slideable dice tray 3508 which receives dice 3524 (not shown in this figure) for disinfection when the dice tray 3508 is in the closed position. Slideable dice tray 3508 slides in and out of housing 3502. To assist in a smoother operation, shaft 3518 may be supported by linear bearing, bushings, or similar. Operational buttons 3510 and 3112 are provided and may be assigned different tasks such as, start, stop, interrupt, etc. Also provided is a display 3514 which provides operation information to the user such as disinfecting on, disinfecting off, disinfecting complete, dice tray open, dice tray locked, unit jammed, elapsed time of use, need for service, etc. Any of the embodiments of the present invention may also employ such a display. The display may be a LCD, LED, OLED, or the like.

FIG. 36 illustrates a perspective view of an automated dice boat UVC disinfecting unit embodiment of the present invention shown in a loading/unloading position. Automated dice boat UVC disinfecting unit 3500 includes a housing 3502, an upper housing portion 3504, and lower housing 3506. Located between the upper housing 3504 and lower housing 3506 is a slidable dice tray 3508 which receives dice 3524 for disinfection when the dice tray 3508 is in the closed position. Slidable dice tray 3508 slides into and out of the housing 3502 as illustrated by path 3526. To assist in a smoother operation, shaft 3518 may be supported by linear bearings, bushings, or similar. Operational buttons 3510 and 3112 are provided and may be assigned different tasks such as, start, stop, interrupt, etc. Also provided is a display 3514 which provides operation information to the user such as disinfecting on, disinfecting off, disinfecting complete, dice tray open, dice tray locked, unit jammed, elapsed time of use, need for service, etc. Any of the embodiments of the present invention may also employ such a display. The display may be a LCD, LED, OLED, or the like. A first array of UVC LEDs 3520 are located within upper housing 3504 and a second array of UVC LEDs 3522 are located within lower housing 3506. As illustrated, dice tray 3508 is preferably constructed with a quartz or similar UV transparent bottom material 3509 that allows for transmission of the UV light from the bottom to more effectively treat all surfaces of the objects to be disinfected. In this and similar embodiments of the present invention, only the bottom of the dice tray 3508 would be UV transmissive so as to contain the UV light within UVC chamber 3511. To ensure that little or no light escapes from the automated dice boat UVC disinfecting unit 3500, a first mechanical, magnetic, electronic, or similar interlock device cooperates with a second mechanical, magnetic, electronic, or similar interlock device 3528 is provided to ensure that the dice tray 3508 is in the closed position prior to energizing the UVC light source. The maximum escaping UVC radiation for the automated dice boat UVC disinfecting unit 3500 may be dictated by FDA maximum human exposure times.

During operation, the dice 3524 are placed into the slidable dice tray 3508 and the start button 3510 is pressed to begin the UVC disinfection process and operation. Dice tray 3508 slides into and out of on path 3526 until it is in the closed and interlocked position. Those skilled in the art will recognize that while this embodiment of the present invention illustrated automatically opens and closes, similar movement and functions can be achieved by manual mechanical means. Similarly, any embodiment of the present invention that includes automated opening and closing mechanisms may also utilize a manual mechanism alternative.

Once the dice tray 3508 is in the closed and interlocked position, the UVC LEDs may be energized via push button 3510 to provide for the UVC disinfecting radiation. Alternatively, the operation may be more fully automated where a sensor is provided to detect when the dice are loaded into the dice tray 3508 whereas the dice tray 3508 automatically moves into the UVC chamber 3511. The cycle time for the disinfecting of the dice 3524 is generally based on time and/or intensity to ensure that at least a portion of the dice have been disinfected. Once the dice 3524 have been at least partially disinfected, the dice tray 3508 of the automated dice boat UVC disinfecting unit 3500 opens and returns to the load/unload position as shown in FIG. 7. Once opened, the disinfected dice 3524 can then be used in service for the game.

FIG. 37 illustrates a top plan view of an automated dice boat UVC disinfecting unit embodiment of the present invention shown in a loading/unloading position. As illustrated, automated dice boat UVC disinfecting unit 3500 includes a housing 3502, an upper housing portion 3504, and lower housing 3506. Located between the upper housing 3504 and lower housing 3506 is a slidable dice tray 3508 which receives dice 3524 for disinfection when the dice tray 3508 is in the closed position. Slidable dice tray 3508 slides along path 3526. To assist in a smoother operation, shaft 3518 may be supported by linear bearing, bushings, or similar. Operational buttons 3510 and 3112 are provided and may be assigned different tasks such as, start, stop, interrupt, etc. Also provided is a display 3514 which provides operation information to the user such as disinfecting on, disinfecting off, disinfecting complete, dice tray open, dice tray locked, unit jammed, elapsed time of use, need for service, etc. Any of the embodiments of the present invention may also employ such a display or in the alternative utilize a series of LED indicator lights signifying various conditions. The display may be a LCD, LED, OLED, or the like.

A first array of UVC LEDs 3520 are located within upper housing 3504 and a second array of UVC LEDs 3522 are located within lower housing 3506. As illustrated, dice tray 3508 is preferably constructed with a quartz or similar UV transparent material bottom 3509 that allows for transmission of the UV light from the bottom to more effectively treat all surfaces of the objects to be disinfected. In this and similar embodiments of the present invention, only the bottom 3509 of the dice tray 3508 would be UV transmissive so as to contain the UV light within UVC chamber 3511. To ensure that little or no light escapes from the automated dice boat UVC disinfecting unit 3500, a first mechanical, magnetic, electronic, or similar interlock device cooperates with a second mechanical, magnetic, electronic, or similar interlock device 3528 is provided to ensure that the dice tray 3508 is in the closed position prior to energizing the UVC light source. The maximum escaping UVC radiation for the automated dice boat UVC disinfecting unit 3500 may be dictated by FDA maximum human exposure times.

During operation, the dice are placed into the slidable dice tray 3208 and the start button 3210 is pressed to begin the UVC disinfection process and operation. Servo motor 32535 is engaged to rotate shaft 3534 which in turn drives pinion gear 3235 which in turn drives rack 3236 which is connected to the dice tray 3208 and move the dice tray into the closed position. When the disinfection process ends or the stop button 3512 is pressed or similar condition, the opposite occurs and the dice tray 3208 moves into the load/unload position. Dice tray 3508 slides along path 3526 until it is in the closed and interlocked position. Those skilled in the art will recognize that while this embodiment of the present invention illustrated automatically opens and closes, similar movement and functions can be achieved by manual mechanical means. Similarly, any embodiment of the present invention that includes automated opening and closing mechanisms or other automated features may also utilize manual mechanism alternatives. Moreover, those skilled in the art will recognize that while mechanical, magnetic or electronic interlocks are illustrated in many embodiments of the present invention, similar interlock may be achieved by mechanical or electromechanical means utilizing latches, springs, pins, microswitches, etc.

Once the dice tray 3508 is in the closed and interlocked position, the UVC LEDs may be energized via push button 3510 to provide for the UVC disinfecting radiation. Alternatively, the operation may be more fully automated where a sensor is provided to detect when the dice are loaded into the dice tray 3508 whereas the dice tray 3508 automatically moves into the UVC chamber 3511. The cycle time for the disinfecting of the dice is generally based on time and/or intensity to ensure that at least a portion of the dice have been disinfected. Once the dice have been at least partially disinfected or the stop button pressed, the dice tray 3508 of the automated dice boat UVC disinfecting unit 3500 opens and returns to the load/unload position as shown in broken line. Once opened, the disinfected dice can then be used in service for the game.

Figure 38:
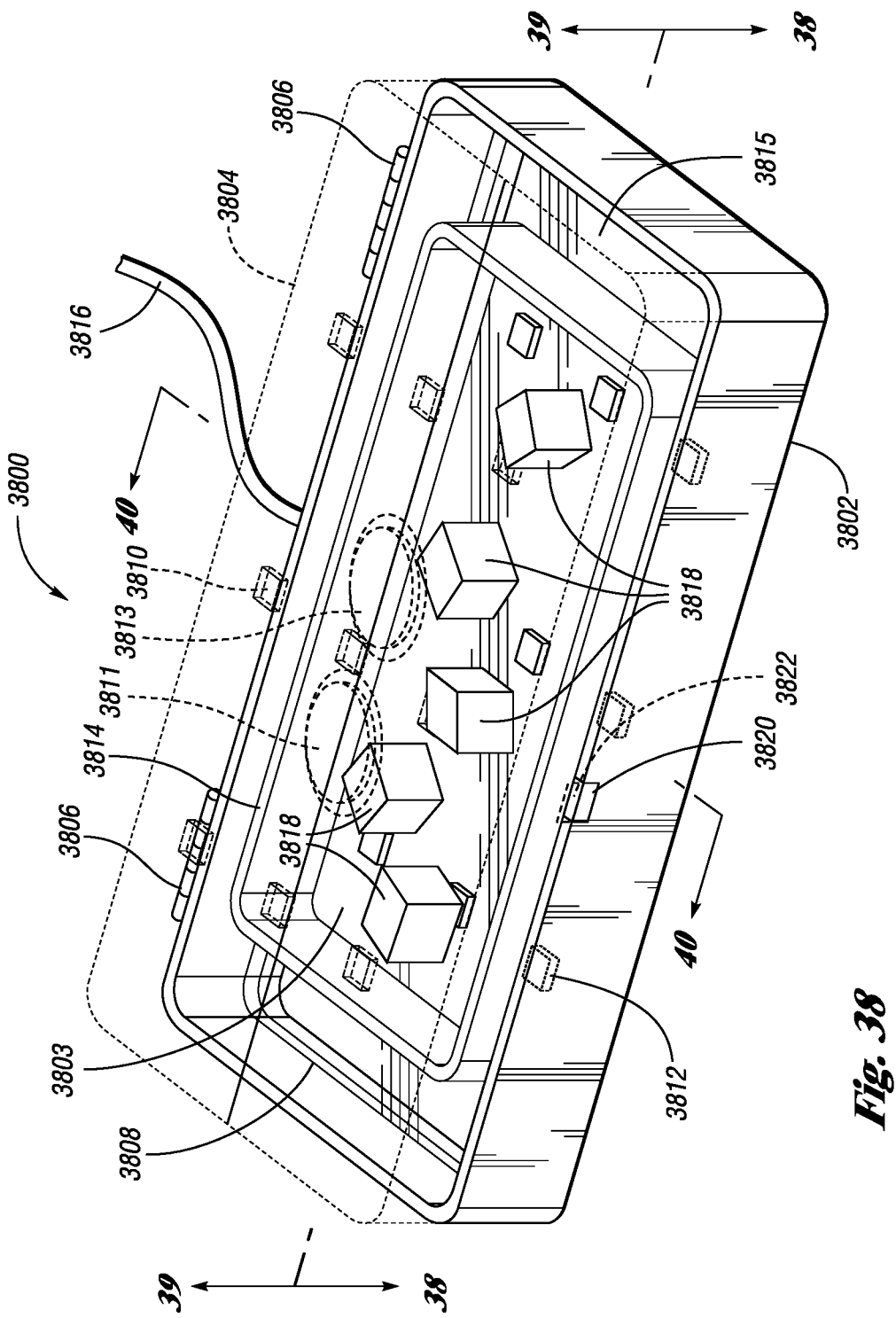
FIG. 38 illustrates a perspective view of a manual opening UVC dice disinfecting unit according to embodiments of the present invention.

FIG. 38 illustrates a manually operated dice UVC disinfecting unit embodiment of the present invention. Manually operated dice UVC disinfecting unit 3800 includes a lower housing 3802 and an upper housing 3804 which are pivotably connected by hinges 3806. Upper housing member 3804 includes an array of UVC LEDs 3810 which are mounted on one or more printed circuit boards (PCBs). Lower housing member 3802 also includes an array of UVC LEDs 3812 which are mounted on one or more PCBs 3817. For any embodiment of the present invention, PCBs are commonly employed to support UVC LEDs and associated functionality or monitoring. Those skilled in the art will recognize that various PCBs, integrated circuits, etc., may be employed to control and monitor operation of the various embodiments of the present invention. Electronic circuitry of this type are well known in the art and may include such functionality or monitoring of fan circuit, low voltage detection, high voltage detection, LCD module, interlocks, inductive load switches, optical interrupt, temperature sensors, LED drivers, power detection, module switches, servo motors, radiation leakage, position sensors, timing switches, lamp failure, etc. This list of functionality or monitoring is representative only and not intended to be a full exhaustive list and each embodiment of the present invention may have differing circuitry controlling functionality or monitoring than other embodiments of the present invention. Manually operated dice UVC disinfecting unit 3800 also include operational buttons 3811 and 3813 which may be assigned different tasks such as, start, stop, interrupt, etc. These buttons may include RGB LED lighting to signify differing states of operation such as yellow in the off state, green for the start state, red in the disinfecting state, blue in the finished disinfecting state, etc. Although this embodiment of the present invention does not include LED indicators or as previously described, they may be included to enhance operability. Power for the manually operated dice UVC disinfecting unit 3800 is supplied via power input 3816. To ensure the manually operated dice UVC disinfecting unit 3800 cannot energize UVC LED arrays 3810 and 3812 with the unit open, a magnetic interlock 3820 cooperating with 3822 is provided to ensure the energizing of UVC LED arrays 3810 and 3812 can only occur when the manually operated dice UVC disinfecting unit 3800 is in the fully closed position. In such enclosures, it is common that certain areas withing the UVC chamber 3803 may have lower intensity than other areas more proximate to the UVC LED arrays 3810 and 3812. For instance, the periphery of the UVC chamber 3803 will naturally have a lower intensity than areas directly below the UVC LED arrays, 3810 and 3812. Although this condition may be somewhat improved by utilizing UVC reflective materials, it often remains that there is a significant variance in intensity levels along the periphery. To ensure that the dice are all effectively disinfected to the approximate same degree, a constant intensity perimeter structure is established by providing an open enclosure 3814 for dice placement which is centrally located withing the UVC chamber 3803. Open enclosure 3814 may either be constructed of UVC reflective materials or UVC transparent materials as previously discussed. To further ensure that the dice are treated on all sides, a quartz plate or similar material plate 3808 is provided to allow the transmission of the UVC radiation to the bottom of the dice as the dice rest on this surface. The reflective inner surfaces of upper housing 3804 and lower housing 3802 along with open enclosure 3814 cooperate to allow for UVC treatment of the sides of the dice.

FIG. 39 illustrates a section view taken along lines 39-39 in FIG. 38 of a manual opening UVC dice disinfecting unit embodiment 3800. As illustrated, the lower housing 3802 includes hinges 3806 for attachment to upper housing 3804. Power is supplied through power cord 3816 which supplies power to the electronic circuitry, PCBs and UVC arrays, 3810 and 3812. Although not shown, routing of power to the upper UVC LED array 3810 and associated PCB 3824 may be made by any convenient means as well known in the art. Lower housing 3802 provides for the lower portion of a UVC chamber 3803. UVC lighting is provided by the UVC LED array 3812 which is located below a UVC transmissive material such as a quartz plate 3808. A first interlock mechanism 3820 cooperates with second interlock mechanism 3822 to ensure the UVC LED arrays 3810 and 3812 cannot be energized without the manually operated dice UVC disinfecting unit 3800 being in a closed position. To ensure that the dice are all effectively disinfected to the approximate same degree, a constant intensity perimeter is established by providing an open enclosure 3814 for dice placement which is centrally located withing the UVC chamber 3803. Open enclosure 3814 may either be constructed of UVC reflective materials or UVC transparent materials as previously discussed.

FIG. 40 illustrates a section view taken along lines 40-40 in FIG. 38 of a manual opening UVC dice disinfecting unit 3800. As illustrated, the upper housing 3804 includes hinges 3806 for attachment to lower housing 3802. Although not shown, routing of power to the upper UVC LED array 3810 and associated PCB 3824 may be made by any convenient means as well known in the art. Upper housing 38042 provides for the upper portion of a UVC chamber 3803. UVC lighting is provided by the UVC LED array 3810. Although not always necessary, a UVC transmissive material such as a quartz plate may be added to allow for a safer working environment for the UVC LED array 3810. A second interlock mechanism 3822 cooperates with first interlock mechanism 3820 to ensure the UVC LED arrays 3810 and 3812 cannot be energized without the manually operated dice UVC disinfecting unit 3800 being in a closed position.

FIG. 41 illustrates a section view taken along lines 41-41 in FIG. 38 of a manual opening UVC dice disinfecting unit 3800. As illustrated, the lower housing 3802 includes hinges 3806 for attachment to upper housing 3804. Power is supplied through power cord 3816 which supplies power to the electronic circuitry, PCBs and UVC arrays, 3810 and 3812. Although not shown, routing of power to the upper UVC LED array 3810 and associated PCB 3824 may be made by any convenient means as well known in the art. Lower housing 3802 provides for the lower portion of a UVC chamber 3803. UVC lighting is provided by the UVC LED array 3812 which is located on a PCB 3824 below a UVC transmissive material such as a quartz plate 3808. A first interlock mechanism 3820 cooperates with second interlock mechanism 3822 to ensure the UVC LED arrays 3810 and 3812 cannot be energized without the manually operated dice UVC disinfecting unit 3800 being in a closed position. To ensure that the dice are all effectively disinfected to the approximate same degree, a constant intensity perimeter is established by providing an open enclosure 3814 for dice placement which is centrally located withing the UVC chamber 3803. Open enclosure 3814 may either be constructed of UVC reflective materials or UVC transparent materials as previously discussed. The upper housing 3804 is attached to hinges 3806 for attachment to lower housing 3802. The arcuate movement path is shown by arrow 3828 which rotates about the axis of the hinges 3806. Although not shown, routing of power to the upper UVC LED array 3810 and associated PCB 3824 may be made by any convenient means as well known in the art. Upper housing 3802 provides for the upper portion of a UVC chamber 3803. UVC lighting is provided by the UVC LED array 3810. Although not always necessary, a UVC transmissive material such as a quartz plate may be added to allow for a safer working environment for the UVC LED array 3810. A second interlock mechanism 3822 cooperates with first interlock mechanism 3820 to ensure the UVC LED arrays 3810 and 3812 cannot be energized without the manually operated dice UVC disinfecting unit 3800 being in a closed position.

Figure 42:
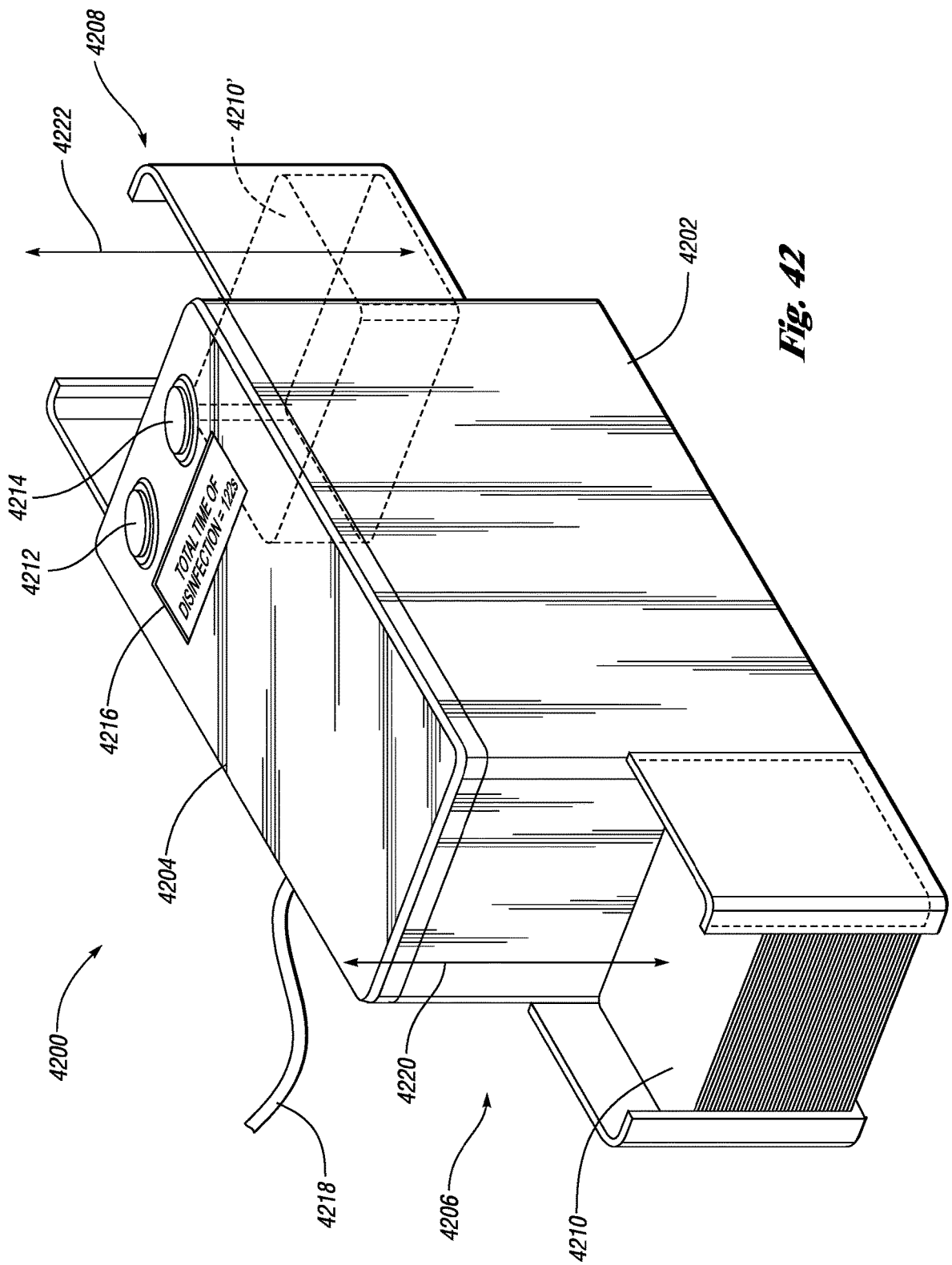
FIG. 42 illustrates a perspective view of a playing card disinfecting unit according to the embodiments of the present invention.

FIG. 42 illustrates a perspective view of a playing card UVC disinfection unit embodiment of the present invention 4200. UVC disinfection unit 4200 includes a main housing 4202 and a cover 4204 which is secured to the UVC disinfection unit housing 4202 in any conventional means via machine screws hinges or the like. Mounted on or in cover plate 4204 are one or more operational buttons such as a 4212 and button 4214 which may be assigned different tasks such as, start, stop, interrupt, etc. These buttons may include RGB LED lighting to signify differing states of operation such as yellow in the off state, green for the start state, red in the disinfecting state, blue in the finished disinfecting state, etc. UVC disinfection unit 4200 includes a display 4216 which provides operation information to the user such as disinfecting on, disinfecting off, disinfecting complete, unit jammed, elapsed time of use, need for service, etc. Any of the embodiments of the present invention may also employ such a display. The display may be a LCD, LED, OLED, touch screen, or the like. Power is supplied by power cord 4218 which feeds power to battery or storage unit 4236 (shown in FIG. 43) and powers display 4216 and operational buttons 4212, 4214 via connections 4264.

A first card receiving member 4206 receives cards 4210 to be sterilized while a second card receiving member 4208 receives cards 4210' that have been sterilized. Directional arrows 4220 and 4222 represent that the cards 4210, 4210' and/or the first and second receiving members 4206, 4208 may move vertically.

Figure 43:
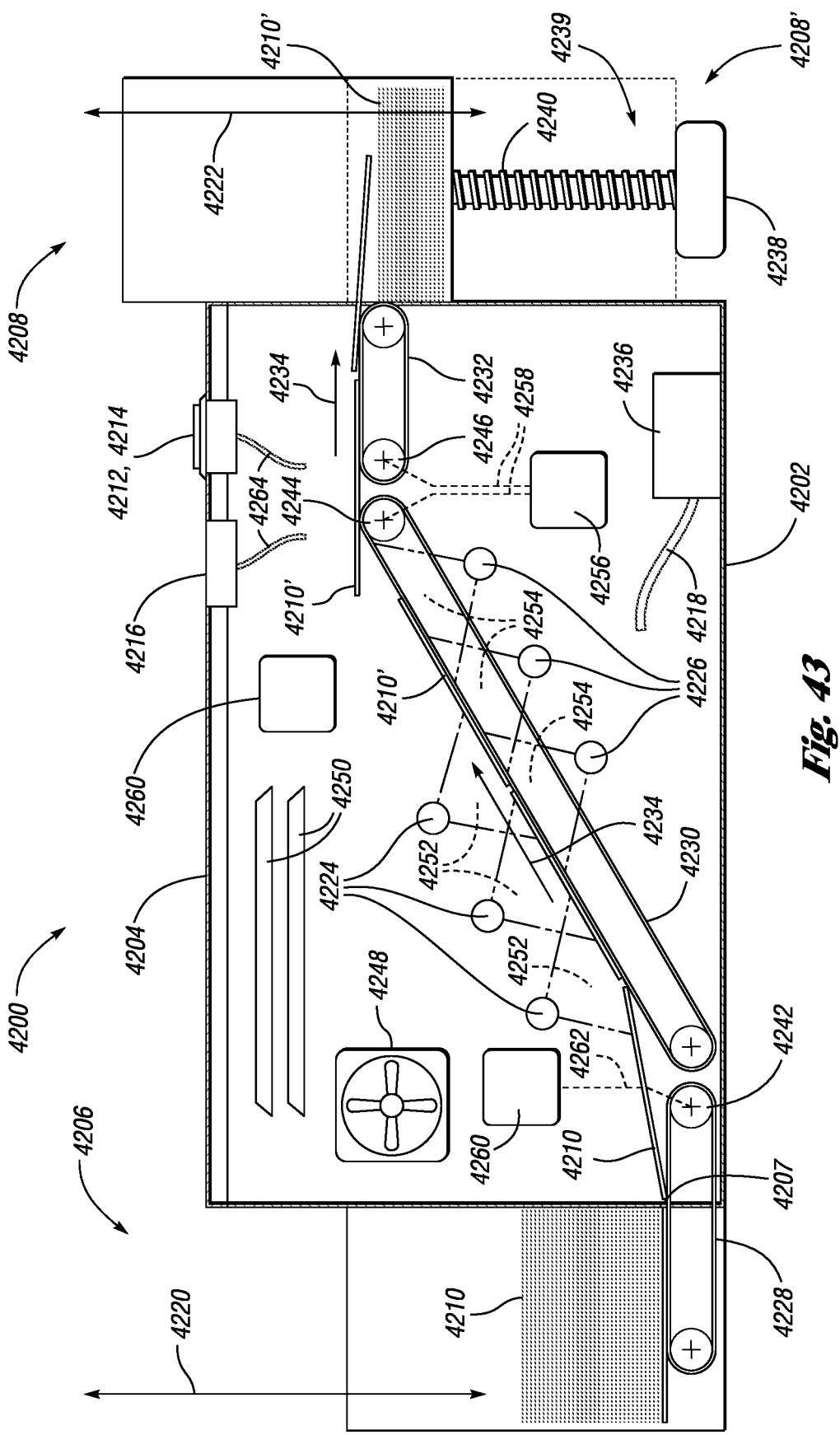
FIG. 43 illustrates a cross section view of a playing card disinfecting unit according to the embodiments of the present invention.

FIG. 43 illustrates a cross-sectional view of the playing card UVC disinfection unit 4200 shown in FIG. 42. Cards 4210 stacked in the first card receiving member 4206 are individually grabbed off the bottom of the card stack by a first conveyor belt 4228 driven by a first pair of spaced rollers 4242. Motor 4260, via connection 4262, powers at least one of the spaced rollers 4242 thereby moving the first conveyor belt 4228. After being grabbed by the first conveyor belt 4228, the individual cards 4210 are directed into the UVC disinfection unit 4200 via slot 4207 in the housing 4202. A second conveyor belt 4230 proximate to the first conveyor belt 4228 is driven by a second pair of spaced rollers 4244. The second conveyor belt 4230 carries the individual cards 4210 upwards (direction arrow 4234) passed a series of upper UVC LEDs 4224 and lower UVC LEDs 4226. The second conveyor belt 4230 may move continuously or intermittingly to provide the cards 4210 with sufficient UV light to sterilize the cards 4210. As positioned, each of the upper UVC LEDs 4224 subject an area 4252 near an upper surface of the cards 4210 to UV light and each of the lower UVC LEDs 4226 subject an area 4254 near a bottom surface of the cards 4210 to UV light. A third conveyor belt 4232 proximate to the second conveyor belt 4230 is driven by a third pair of spaced rollers 4246 and receives sterilized cards 4210' from the second conveyor belt 4230 and directs them horizontally (direction arrow 4234) into the second receiving member 4208. The second receiving member 4208 may be raised a lowered by a mechanism 4239 comprising, in one embodiment, a threaded rod 4240 and motor 4238. Motor 4256, via connections 4258, drives the second and third conveyor belts 4230, 4232. Separate, individual motors may be used as well.

Fans 4248 and vents 4250 in the housing serve to expel heat generated by the internal components including the various motors and UVC LEDs.

While the cards are shown being transported upwards within the UVC disinfection unit 4200, one skilled in the art will recognize that the cards may be transported horizontally or downward depending on the configuration of the conveyor belts.

FIG. 44 illustrates a perspective view of an upper and lower UVC chamber embodiment of the present invention. As illustrated, upper and lower UVC chamber assembly 4400 includes an upper UVC chamber assembly 4402 and a lower UVC chamber assembly 4404. Upper and lower UVC chambers 4402 and 4404, respectively, include an upper box like structures 4416 and a lower box like structure 4420, each with one open side facing the opposite UVC chamber to allow for UVC lighting to be applied to both a top and bottom surface of an object to be disinfected. In the embodiment illustrated, the disinfection target is a playing card 4406, however, those skilled in the art will recognize that a great many objects may be disinfected utilizing the UVC chamber embodiment of the present invention. As schematically shown by movement arrows 4422 and 4424, either one of the UVC chambers 4402 and 4404 may be fixed in a UVC chamber assembly 4400 or may be moveable, usually in a vertical direction to allow for UVC disinfection target objects to move easily into the space between the upper and lower UVC chambers 4402 and 4404. In addition, either one of the upper and lower UVC chambers 4402 and 4404 or both may move to clear jams that may occur during the disinfection operation. Preferably, one or more sides of the UVC chambers 4416 and 4420 are constructed of UVC reflective materials such as polished aluminum. However, depending on the desired UVC dispersion of UVC chambers 4416 and 4420, other materials may be utilized that either block UVC light such as stainless steel, glass or similar or materials that are UVC light transmissive such as quartz, fused silica, sapphire, polymers, etc. Each UVC chamber assembly 4402 and 4404 contain one or more UVC light sources 4408 and 4424, respectively, generally directed toward the opening in the box like structures 4416 and 4412. As illustrated, the UVC lighting sources are UVC LED modules which contain UVC LEDs 4424. Power for the UVC LEC modules is supplied vie electrical connections

4410 and 4416. Operational aspects of the UVC chamber and associated UVC light sources along with movement of both the disinfection target and/or UVC chambers may be controlled by a controller (not shown). In this embodiment of the present invention, the UVC disinfection target is a playing card 4406 which passes through a gap 4407 between upper UVC chamber assembly 4402 and lower UVC chamber assembly 4404 in the direction of arrow 4426. Movement of the UVC disinfection target is preferably longitudinal in one direction to allow sequential disinfection of a series of UVC target objects such as playing card 4406 or similar, such as gaming chips, currency, gaming vouchers, dice, etc. Those skilled in the art will recognize that although the movement illustrated is longitudinal, any desired movement may be employed such as lateral movement in one direction or either longitudinal or lateral movement in a number of directions or even orbital. Although the embodiment of the present invention illustrates a pass-through mechanism, the UVC target object may remain stationary between the UVC disinfection chambers for UVC disinfection if desired.

FIG. 45 illustrates a cross section view of an upper and lower UVC chamber embodiment of the present invention. As illustrated, upper and lower UVC chamber assembly 4400 includes an upper UVC chamber assembly 4402 and a lower UVC chamber assembly 4404. Upper and lower UVC chambers 4402 and 4404, respectively, include an upper box like structures 4416 and a lower box like structure 4420, each with one open side facing the opposite UVC chamber to allow for UVC lighting to be applied to both a top and bottom surface of an object to be disinfected. In the embodiment illustrated, the disinfection target is a playing card 4406, however, those skilled in the art will recognize that a great many objects may be disinfected utilizing the UVC chamber embodiment of the present invention. As schematically shown by movement arrows 4422 and 4424, either one of the UVC chambers 4402 and 4404 may be fixed in a UVC chamber assembly 4400 or may be moveable, usually in a vertical direction to allow for UVC disinfection target objects to move easily into the space between the upper and lower UVC chambers 4402 and 4404. In addition, either one of the upper and lower UVC chambers 4402 and 4404 or both may move to clear jams that may occur during the disinfection operation. Preferably, one or more sides of the UVC chambers 4416 and 4420 are constructed of UVC reflective materials such as polished aluminum. However, depending on the desired UVC dispersion of UVC chambers 4416 and 4420, other materials may be utilized that either block UVC light such as stainless steel, glass or similar or materials that are UVC light transmissive such as quartz, fused silica, sapphire, polymers, etc. Each UVC chamber assembly 4402 and 4404 contain one or more UVC light sources 4408 and 4424, respectively, generally directed toward the opening in the box like structures 4416 and 4412. As illustrated, the UVC lighting sources are UVC LED modules which contain UVC LEDs 4424. Power for the UVC LEC modules is supplied vie electrical connections 4410 and 4416. Operational aspects of the UVC chamber and associated UVC light sources along with movement of both the disinfection target and/or UVC chambers may be controlled by a controller (not shown). In this embodiment of the present invention, the UVC disinfection target is a playing card 4406 which passes through a gap 4407 between upper UVC chamber assembly 4402 and lower UVC chamber assembly 4404. As illustrated, due to direct and indirect UVC lighting, the upper and lower surfaces of the UVC target 4406 are well covered for a generally acceptable UVC disinfection. As the indirect UVC light is reflected off the internal walls utilizing highly reflective UVC materials, even the edges of the UVC disinfection target are treated. Moreover, due to the relatively thin gap 4407, little UVC light will escape from the UVC disinfecting unit 4400. If it is desirable that an even further reduction in UVC light escaping form the UVC disinfecting unit 4400 is necessary, flexible UVC blocking barriers, brushes, or similar may be attached to at least partially seal the gap 4407.

Figure 46:
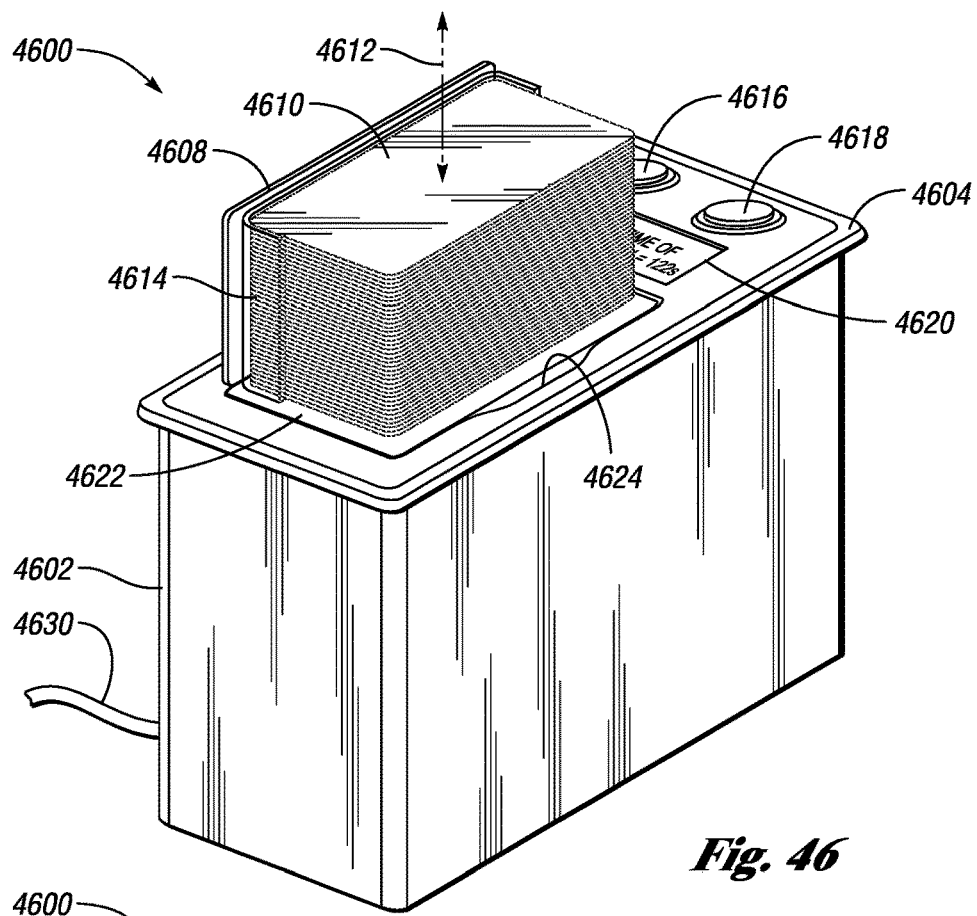
FIG. 46 illustrates a perspective view of a playing card disinfecting unit according to the embodiments of the present invention in the deck loading or ejecting position.

FIG. 46 illustrates a perspective view of a playing card disinfecting unit embodiment of the present invention in the deck loading or ejecting position. Playing card disinfecting unit 4600 includes housing 4602 and flanged cover plate 4604. Flanged cover plate 4604 is utilized for recessed placement into a gaming table or the like. In the alternative, for table top or similar placements, flanged cover plate 4604 may be flush with housing 4602 and therefore not require the flange illustrated. Located withing flanged cover plate 4604 is an opening 4624 for receiving and ejecting playing cards 4610. As illustrated by direction arrow 4612, the deck or decks of playing cards 4610 move vertically between the load position shown, the UVC disinfection processing area and the eject position via an elevator mechanism similar to those already or will be described in other embodiments of the present invention. To assist in positioning the deck or decks of cards 4610, an acrylic positioning member 4614 is attached to the elevator support 4622. Hinged door 4608 cooperates by opening against a spring bias for accepting or loading or removal or ejection of playing card 4610. One or more electrically connected buttons 4616 and 4618 are provided to control operation of the playing card disinfecting unit. An LED display 4620 is provided to inform the use of the current status of the playing card disinfecting unit 4600. Power for the playing card disinfecting unit 4600 is proved through electrical supply 4630. Playing card disinfecting unit also contains the necessary control circuitry to operate the playing card disinfecting unit 4600, to inform the user of current status via LED display 4620, control movement of servo motors and the like, etc.

Figure 47:
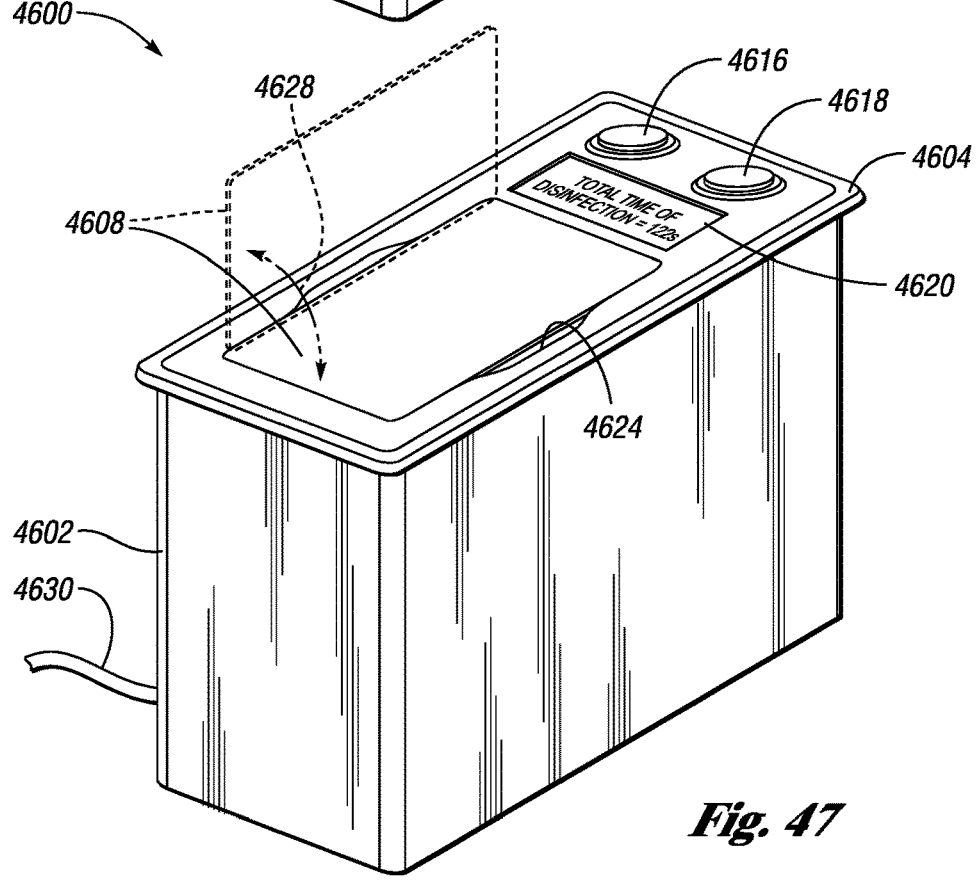
FIG. 47 illustrates a perspective view of a playing card disinfecting unit according to the embodiments of the present invention while the playing cards are inside the playing card disinfecting unit and being disinfected.

FIG. 47 illustrates a perspective view of a playing card disinfecting unit embodiment of the present invention while the playing cards are inside the playing card disinfecting unit and being disinfected. Playing card disinfecting unit 4600 includes housing 4602 and flanged cover plate 4604. Flanged cover plate 4604 is utilized for recessed placement into a gaming table or the like. In the alternative, for table top or similar placements, flanged cover plate 4604 may be flush with housing 4602 and therefore not require the flange illustrated. Located withing flanged cover plate 4604 is an opening 4624 for receiving and ejecting playing cards 4610. As illustrated, playing cards 4610 have been received and placed in the UVC disinfection chamber and therefore concealed by the spring biased closed door 4608. Door 4608 additionally acts to at least partially seal the playing card disinfecting unit 4600 from escaping UVC lighting. Additional sealing mechanisms may also be employed such as seals, brushes, doors, etc. Once the playing card disinfecting unit 4600 has finished the UVC disinfection cycle, the deck or decks of playing cards will be manually or automatically lifted to the removal or ejection position as shown in FIG. 46 via the elevator mechanism already described. One or more electrically connected buttons 4616 and 4618 are provided to control operation of the playing card disinfecting unit. An LED display 4620 is provided to inform the use of the current status of the playing card disinfecting unit 4600. Power for the playing card disinfecting unit 4600 is proved through electrical supply 4630. Playing card disinfecting unit also contains the necessary control circuitry to operate the playing card disinfecting unit 4600, to inform the user of current status via LED display 4620, control movement of servo motors and the like, etc.

FIG. 48A illustrates a schematic side elevation view of a playing card disinfecting unit including a stack separator mechanism embodiment of the present invention in a first position as it is about one third of the way through the UVC disinfecting cycle. As illustrated, stack separator mechanism 4800 accepts UVC disinfection target objects such as a deck or decks of playing cards 4802. The deck or decks of playing cards 4802 are separated into two groups during UVC disinfection processing including a first lower stack of playing cards 4804 that have been UVC disinfected and a second upper stack of playing cards 4806 that have yet to be UVC disinfected. Stack separator mechanism 4800 includes a ratcheting separating mechanism 4808 which separates each card from the next, starting from the bottom up of the deck or decks playing cards 4802. Ratcheting separator mechanism 4808 is linked to a UVC light source assembly 4809 so that both travel in the same direction and with the same spacing between. UVC light source assembly 4809 includes a UVC light source 4820 which may be a UVC mercury lamp, UVC excimer lamp, UVC LEDs, or any similar light source that is capable of emitting UVC light. Those skilled in the art will recognize that for any embodiment of the present invention, many alternative UVC light sources may be employed. UVC light source 4820 may preferably include a focusing shield 4822 which assists in limiting UVC lighting exposure of other objects or surfaces other than the UVC disinfecting target. When UVC light source 4820 is energized, it produces a general cone of UVC lighting 4824 that is utilized to disinfect the UVC disinfecting targets such as playing cards 4802 within the UVC disinfecting area 4826. Those skilled in the art will recognize that this general cone of UVC lighting 4824 or other light distribution illustrated in other embodiments of the present invention is not limited by the cone illustrated but may extend beyond the cone and either distributed to other areas of the UVC disinfecting mechanisms or a lesser intensity depending on the UVC light source and/or shielding employed. The deck or decks of playing cards 4802 are supported from the bottom by elevator support 4622, shown in broken line.

Stack separator mechanism 4800 includes a ratcheting separating mechanism 4808 which separates each card from the next, starting from the bottom up of the deck or decks UVC target object playing cards 4802. Ratcheting separating mechanism 4808 includes rachet bar 4814 which is spring biased via one or more torsion springs 4810 against ratchet support 4816 which pivotably supports rachet bar 4814 by pin 4812. Accordingly, ratchet bar 4814 is generally fixed in the horizontal position while in use and/or traveling in the upward vertical direction. Those skilled in the art will recognize that other paging through a stack of UVC disinfection targets embodiments of the present invention may also be utilized in this embodiment of the present invention. As illustrated, distance D1 represents the longitudinal length of a UVC target playing card 4804 from its leftmost edge to the rightmost edge. In the horizontal position, the ratchet bar tip 4815 has a distance D2 from the leftmost side of the UVC target playing card to the tip of the rachet bar 4815 which is lesser than distance D1. As ratcheting separating mechanism 4808 travels upward from a starting position, it will lift the right side of UVC target object playing cards 4804' to an angle of approximately 20 to 30 degrees from horizontal. As the ratcheting separating mechanism 4808 continues to travel in the upward vertical direction, the bottom UVC target playing card 4804 will be released and fall to a generally horizontal position 4830 while the UVC target playing card 4804' will remain in an angular relationship with bottom UVC target object playing card 4804. Those skilled in the art will recognize that any angularity sufficient to allow for an adequate angular separation between the horizontally disposed lower UVC target object playing card 4804 and the upper angularly disposed UVC target object playing card 4804' which provides for generally effective UVC disinfection to at least partially disinfect the UVC target object playing cards may be utilized as determined by the dimensional difference between distance D1 and distance D2. As illustrated, the ratchet bar 4814 comes into contact with the longitudinal edge of the UVC target object playing card 4804 but those skilled in the art will recognize that ratchet bar 4814 may also be poisoned to contact the lateral edges of UVC target object playing card 4804. Upward travel of ratcheting separating mechanism 4808 may be controlled using any conventional means such as a stepper motor and lead screw (not shown but illustrated in other embodiments of the present invention). Travel may be continuous in an upward vertical direction periodically releasing the next UVC target object playing card or in the alternative, the upward vertical travel may be incremental in upward vertical travel steps approximately equal to the thickness of the UVC target object playing card. Those skilled in the art will recognize that the UVC target object need not be a playing card as any similar UVC target object may also be at least partially disinfected by stack separator mechanism 4800 such as paper gaming voucher tickets, currency, etc.

FIG. 48B illustrates a schematic side elevation view of a playing card disinfecting unit including a stack separator mechanism embodiment of the present invention in a second position as it is about two thirds of the way through the UVC disinfecting cycle. As illustrated, stack separator mechanism 4800 accepts UVC disinfection target objects such as a deck or decks of playing cards 4802. The deck or decks of playing cards 4802 are separated into two groups during UVC disinfection processing including a first lower stack of playing cards 4804 that have been UVC disinfected and a second upper stack of playing cards 4806 that have yet to be UVC disinfected. Stack separator mechanism 4800 includes a ratcheting separating mechanism 4808 which separates each card from the next, starting from the bottom up of the deck or decks playing cards 4802. Ratcheting separator mechanism 4808 is linked to a UVC light source assembly 4809 so that both travel in the same direction and with the same spacing between. UVC light source assembly 4809 includes a UVC light source 4820 which may be a UVC mercury lamp, UVC excimer lamp, UVC LEDs, or any similar light source that is capable of emitting UVC light. Those skilled in the art will recognize that for any embodiment of the present invention, many alternative UVC light sources may be employed. UVC light source 4820 may preferably include a focusing shield 4822 which assists in limiting UVC lighting exposure of other objects or surfaces other than the UVC disinfecting target. When UVC light source 4820 is energized, it produces a general cone of UVC lighting 4824 that is utilized to disinfect the UVC disinfecting targets such as playing cards 4802 within the UVC disinfecting area 4826. Those skilled in the art will recognize that this general cone of UVC lighting 4824 or other light distribution illustrated in other embodiments of the present invention is not limited by the cone illustrated but may extend beyond the cone and either distributed to other areas of the UVC disinfecting mechanisms or a lesser intensity depending on the UVC light source and/or shielding employed. The deck or decks of playing cards 4802 are supported from the bottom by elevator support 4622, shown in broken line.

Stack separator mechanism 4800 includes a ratcheting separating mechanism 4808 which separates each card from the next, starting from the bottom up of the deck or decks UVC target object playing cards 4802. Ratcheting separating mechanism 4808 includes rachet bar 4814 which is spring biased via one or more torsion springs 4810 against ratchet support 4816 which pivotably supports rachet bar 4814 by pin 4812. Accordingly, ratchet bar 4814 is generally fixed in the horizontal position while in use and/or traveling in the upward vertical direction. Those skilled in the art will recognize that other paging through a stack of UVC disinfection targets embodiments of the present invention may also be utilized in this embodiment of the present invention. As illustrated, distance D1 represents the longitudinal length of a UVC target playing card 4804 from its leftmost edge to the rightmost edge. In the horizontal position, the ratchet bar tip 4815 has a distance D2 from the leftmost side of the UVC target playing card to the tip of the rachet bar 4815 which is lesser than distance D1. As ratcheting separating mechanism 4808 travels upward from a starting position, it will lift the right side of UVC target object playing cards 4804' to an angle of approximately 20 to 30 degrees from horizontal. As the ratcheting separating mechanism 4808 continues to travel in the upward vertical direction, the bottom UVC target playing card 4804 will be released and fall to a generally horizontal position 4830 while the UVC target playing card 4804' will remain in an angular relationship with bottom UVC target object playing card 4804. Those skilled in the art will recognize that any angularity sufficient to allow for an adequate angular separation between the horizontally disposed lower UVC target object playing card 4804 and the upper angularly disposed UVC target object playing card 4804' which provides for generally effective UVC disinfection to at least partially disinfect the UVC target object playing cards may be utilized as determined by the dimensional difference between distance D1 and distance D2. As illustrated, the ratchet bar 4814 comes into contact with the longitudinal edge of the UVC target object playing card 4804 but those skilled in the art will recognize that ratchet bar 4814 may also be poisoned to contact the lateral edges of UVC target object playing card 4804. Upward travel of ratcheting separating mechanism 4808 may be controlled using any conventional means such as a stepper motor and lead screw (not shown but illustrated in other embodiments of the present invention). Travel may be continuous in an upward vertical direction periodically releasing the next UVC target object playing card or in the alternative, the upward vertical travel may be incremental in upward vertical travel steps approximately equal to the thickness of the UVC target object playing card. Those skilled in the art will recognize that the UVC target object need not be a playing card as any similar UVC target object may also be at least partially disinfected by stack separator mechanism 4800 such as paper gaming voucher tickets, currency, etc.

FIG. 48C illustrates a schematic side elevation view of a playing card disinfecting unit including a stack separator mechanism embodiment of the present invention in a final vertical position at the end of the UVC disinfecting cycle and the beginning of the UVC disinfecting cycle, shown in broken line. As illustrated, stack separator mechanism 4800 accepts UVC disinfection target objects such as a deck or decks of playing cards 4802. Stack separator mechanism 4800 includes a ratcheting separating mechanism 4808 which separates each card from the next, starting from the bottom up of the deck or decks playing cards 4802. Ratcheting separator mechanism 4808 is linked to a UVC light source assembly 4809 so that both travel in the same direction and with the same spacing between. UVC light source assembly 4809 includes a UVC light source 4820 which may be a UVC mercury lamp, UVC excimer lamp, UVC LEDs, or any similar light source that is capable of emitting UVC light. Those skilled in the art will recognize that for any embodiment of the present invention, many alternative UVC light sources may be employed. UVC light source 4820 may preferably include a focusing shield 4822 which assists in limiting UVC lighting exposure of other objects or surfaces other than the UVC disinfecting target. When UVC light source 4820 is energized, it produces a general cone of UVC lighting 4824 that is utilized to disinfect the UVC disinfecting targets such as playing cards 4802 within the UVC disinfecting area 4826. Those skilled in the art will recognize that this general cone of UVC lighting 4824 or other light distribution illustrated in other embodiments of the present invention is not limited by the cone illustrated but may extend beyond the cone and either distributed to other areas of the UVC disinfecting mechanisms or a lesser intensity depending on the UVC light source and/or shielding employed. The deck or decks of playing cards 4802 are supported from the bottom by elevator support 4622, shown in broken line. Following the UVC target object playing card disinfection of all objects and once the ratcheting separating mechanism 4808 reaches its limit of upward vertical travel, it is preferable that UVC light source 4824 be deenergized to discontinue UVC disinfection lighting. Such deenergizing of UV light source 4824 may continue until the next UVC disinfection target playing card cycle begins once the deck or decks of playing cards are loaded and vertically travel downward to the start position by elevator mechanism 4828.

Stack separator mechanism 4800 includes a ratcheting separating mechanism 4808 which separates each card from the next, starting from the bottom up of the deck or decks UVC target object playing cards 4802. Ratcheting separating mechanism 4808 includes rachet bar 4814 which is spring biased via one or more torsion springs 4810 against ratchet support 4816 which pivotably supports rachet bar 4814 by pin 4812. Accordingly, ratchet bar 4814 is generally fixed in the horizontal position while in use and/or traveling in the upward vertical direction. Those skilled in the art will recognize that other paging through a stack of UVC disinfection targets embodiments of the present invention may also be utilized in this embodiment of the present invention. As illustrated, distance D1 represents the longitudinal length of a UVC target playing card 4804 from its leftmost edge to the rightmost edge. When ratcheting separating mechanism 4808 travel reaches its upward limit, the ratcheting separating mechanism 4808 will vertically lower to a starting position. During the vertical lowering of ratcheting separating mechanism 4808, ratchet bar 4814 will rotate, or ratchet, about pin 4812 against the spring bias of one or more torsion springs 4810 to rotationally disengage from the UVC target object playing cards 4802. Once ratcheting separating mechanism 4808 travels to its lower starting position, the spring bias of one or more torsion springs 4810 will rotate the ratchet bar 4814 into its normal horizontal position, starting position. As illustrated, the ratchet bar 4814 comes into contact with the longitudinal edge of the UVC target object playing card 4804 but those skilled in the art will recognize that ratchet bar 4814 may also be poisoned to contact the lateral edges of UVC target object playing card 4804. Upward travel of ratcheting separating mechanism 4808 may be controlled using any conventional means such as a stepper motor and lead screw (not shown but illustrated in other embodiments of the present invention). Travel may be continuous in an upward vertical direction periodically releasing the next UVC target object playing card or in the alternative, the upward vertical travel may be incremental in upward vertical travel steps approximately equal to the thickness of the UVC target object playing card. Those skilled in the art will recognize that the UVC target object need not be a playing card as any similar UVC target object may also be at least partially disinfected by stack separator mechanism 4800 such as paper gaming voucher tickets, currency, etc.

Figure 49:
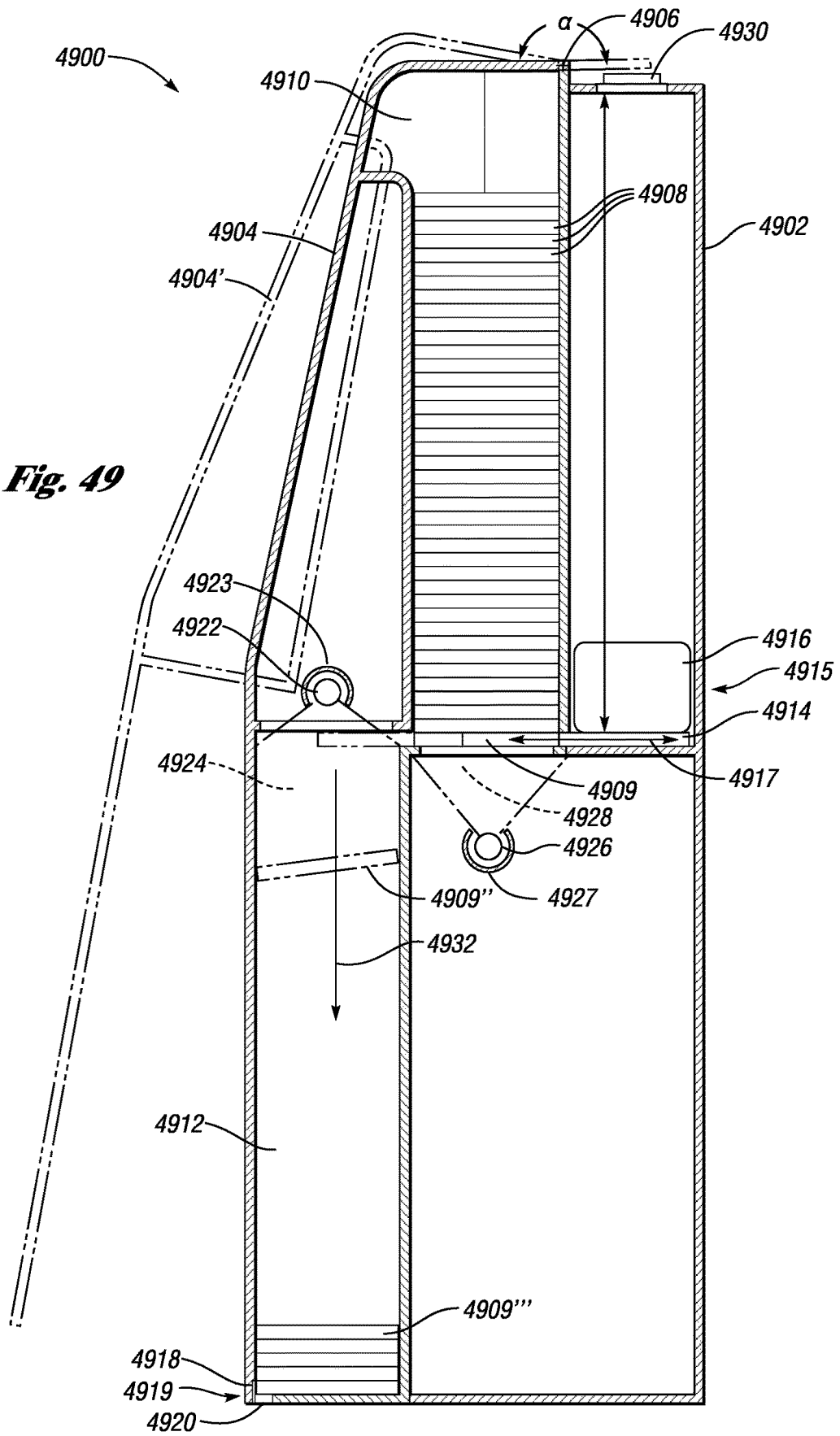
FIG. 49 illustrates a cross section view of a gaming chip disinfecting unit including a stack separator mechanism according to the embodiments of the present invention.

FIG. 49 illustrates a cross section view of a gaming chip disinfecting unit including a stack separator mechanism embodiment of the present invention. Gaming chip disinfecting unit 4900 includes a housing 4902 which supports gaming chips 4908 in both the load or undisinfected area 4910 and the disinfected area 4912. Gaming chip disinfecting unit 4900 also includes are rotatable cover 4904 which is connected via a hinge to housing 4902 and rotates about axis 4906. During the loading or unloading operations, cover 4904 may be rotated manually or by a servo motor or the like by angle α to provide convenient loading or unloading of gaming chips 4908. Cover 4904 is shown during rotation or partial opening by broken line 4904'. Those familiar with the art will recognize that certain materials will respond differently to UNV lighting and may affect material selection such as aluminum for reflective properties as opposed to stainless steel which is nonreflective of UVC light or other materials discussed herein. Generally, gaming chips are first transferred from a gaming chip tray into the upper load or undisinfected area 4910 by the game dealer. After UVC disinfection, chips may be unloaded from the unload area 4912 and returned to the chip tray by the dealer for use in the game. Those familiar with the art will recognize that this embodiment of the present invention may also serve as a chip tray itself. Once the chips 4908 are loaded into the loading or disinfection area 4910, cover 4904 is rotatably returned to the closed position. A magnetic interlock 4919 is provided comprised of primary electronic magnetic interlock component 4918 which is attached to the cover 4904 and secondary electronic magnetic interlock component 4920 which is attached to housing 4902 to insure at least the UVC operation of gaming chip disinfecting unit 4900 cannot be activated unless the interlock is in the closed position to reduce any potential exposure to the dealer or operator of the gaming chip disinfecting unit 4900 or others. Although a magnetic interlock is illustrated, those familiar with the art will recognize that there are a wide variety of sensors that may also serve to ensure closure of the gaming chip disinfecting unit 4900 prior to the starting the UVC disinfection operation or process. Once the gaming chips 4908 are loaded into the loading or undisinfected area 4910 and cover 4904 is closed, the disinfection operation may begin automatically or by the operator pressing a start button 4930, similar to those already described. Button 4930 may also provide for additional functions such as stop, interrupt, etc., or multiple buttons may be incorporated into the gaming chip disinfecting unit 4900. Additionally, and as previously described, a display may be provided to inform the user of the current status of the gaming chip disinfecting unit 4900. Such information may include operational status, ready to start status, unit failure, unit jammed, lamp failure, etc. Upon initiation of the UVC functionality of gaming chip disinfecting unit 4900, gaming chips 4908 have been loaded in to the upper load or undisinfected area 4910. Although the cross-section view of FIG. 49 only illustrates a single stack of gaming chips 4908, the gaming chip disinfecting unit 4900 may include a plurality of columns equal to or greater than the number of columns in the gaming chip tray on the table game or if utilized as the chip tray itself, any number of columns may be included but as commonly used in gaming, the number of columns may equal 12 or 15 columns or any other convenient number as will be illustrated in succeeding figures. As illustrated, a UVC light source 4929 is provided under the load or undisinfected area 4910, to illuminate the bottom surface of the bottom gaming chip 4909. Although this embodiment of the present invention is illustrated utilizing an elongated mercury UVC lamp 4926, or any suitable UVC light source may be utilized such as UVC LEDs, excimer UVC lamps, or the like. UVC lamp 4926, produces UVC light as shown and focused or directed 4928 to the underside of gaming chip 4909 by use of a UVC directional shield 4927. A corresponding UVC illumination assembly is illustrated which focused or directs UNV illumination to the top of a gaming chip 4909, when in the appropriate position, utilizing an elongated mercury UVC lamp 4922, or any suitable UVC light source may be utilized such as UVC LEDs, excimer UVC lamps, or the like. UVC lamp 4922, produces UVC light as shown and focused or directed 4924 to the topside of gaming chip 4909, when in the appropriate position by use of a UVC directional shield 4923. Those familiar with the art will recognize that while various embodiments of the present invention utilize UVC shields or enclosures to assist in concentrating or focusing the UVC illumination, they may not completely eliminate dispersed or reflective UVC illumination. Such dispersed or reflective UVC illumination may either be reduced by utilizing a non-reflective material such as stainless steel or other similar materials with similar properties or enhanced by reflective materials such as aluminum or similar materials.

As the gaming chip disinfecting unit 4900 begins operation, there is normally, but not necessarily, only gaming chips in the load or undisinfected area 4908. At this stage, only the bottom side of gaming chip 4909, or bottom of multiple bottom chips in a multi-column design, is at least partially disinfected by UVC lamp 4926. The time of adequate exposure to the bottom side of gaming chip 4909 to disinfect the surface of gaming chip 4909 is dependent on time and/or intensity of the UVC lamp 4926 and level of disinfection level desired. Those familiar with the art will recognize that any of the embodiments of the present invention may process a particular item to varying degrees of disinfection dependent on time and/or intensity. In addition, those familiar with the art will recognize that the intensity of the UVC source, relative to the object to be disinfected, of any embodiments of the present invention, are affected by the distance of the UVC light source to the target item to be disinfected. Moreover, various means may be provided, as illustrated and described herein, to enhance or focus the UVC light, shield the UVC light from certain areas, allow from reflection, diminish reflection, etc. By way of example, processing time may be provided to disinfect a surface to an approximate 75% level while additional time and/or intensity may raise the disinfection level to 90% or even 99% with additional time and/or intensity. Moreover, items to be disinfected may be repeatedly subjected to the UVC disinfection process to provide for a multi-step disinfection process to raise the disinfection levels, i.e., one pass processing results in 75% disinfection level, second pass processing increases to 90% disinfection level, third pass processing increases to 97% disinfection level, etc.

Once the bottom surface of gaming chip 4909 is at least partially disinfected, ejector 4914 pushes the bottom gaming chip 4909 away from the stack of gaming chips 4908. Ejector 4914 is driven by servo motor 4916 and its movement controlled by any conventional mechanical means or in the alternative, the ejector may be controlled electronically. Arrow 4917 illustrates the ejector movement first to the left to eject the gaming chip 4909 and then retracts to the right, as shown, to allow for the stack of gaming chips 4908 to drop by a distance approximately equal to a thickness of gaming chip 4909, thereby positioning the next gaming chip in the stack to be processed. Preferably, ejector 4914 ejects gaming chips 4909 at a predetermined rate, e.g., every 2 seconds. Alternatively, operation and movement of ejector 4917 may be a continuous in and out movement. During the ejecting cycle, the gaming chip is ejected at a rate which allows for the top surface of gaming chip 4909' to be illuminated by UVC lamp 4922 which is shielded by shield 4923 and at least partially disinfected. Eventually, the gaming chip 4909 moves laterally and reaches an area in the unload or partially disinfected area and losses all underside support, the gaming chip 4909' will drop by gravity feed, as illustrated in broken line to 4909" in the direction of arrow 4932, to the bottom of the unload or partially disinfected area as illustrated in broken line 4909''' at which time the top surface of gaming chip 4909 is further illuminated by UVC lamp 4922. If desired, an elevator support mechanism may be provided (similar to elevator mechanisms illustrated and discussed herein) to receive each gaming chip 4909 after the gaming chip 4909 enters the unload disinfected area 4912, indexing downward incrementally by approximately the thickness of the gaming chip 4909 for each gaming chip cycle. Preferably, some spacing is provided between the gaming chip 4909' and the side walls of the unload or disinfected area 4912 to allow for at least some UVC light exposure to the sides of gaming chip 4909''' to at least partially disinfect the gaming chip edges. Once ejector 4914 has retracted to its original starting position and the gaming chip stack drops, the cycle is repeated, chip by chip, until all gaming chips 4908 have been at least partially disinfected. Gaming chip disinfecting unit 4900 may always cycle the number of times equal to the maximum number of gaming chips in a stack 4908 to ensure all gaming chips 4908 have been processed or alternatively a sensor may be provided to detect when the last gaming chip 4908 has been processed. As previously described, gaming chip disinfecting unit 4900 includes a number of columns so multiple rows of gaming chips 4908 can be disinfected simultaneously. Once all gaming chips 4908 have been processed, cover 4904 may be manually or automatically opened to allow the game dealer access and to return the gaming chips 4908 to the chip tray on the gaming table. Alternatively, gaming chips may remain in the gaming chip disinfecting unit 4900 during play in which case gaming chip disinfecting unit 4900 serves as the gaming chip tray.

Figure 50:
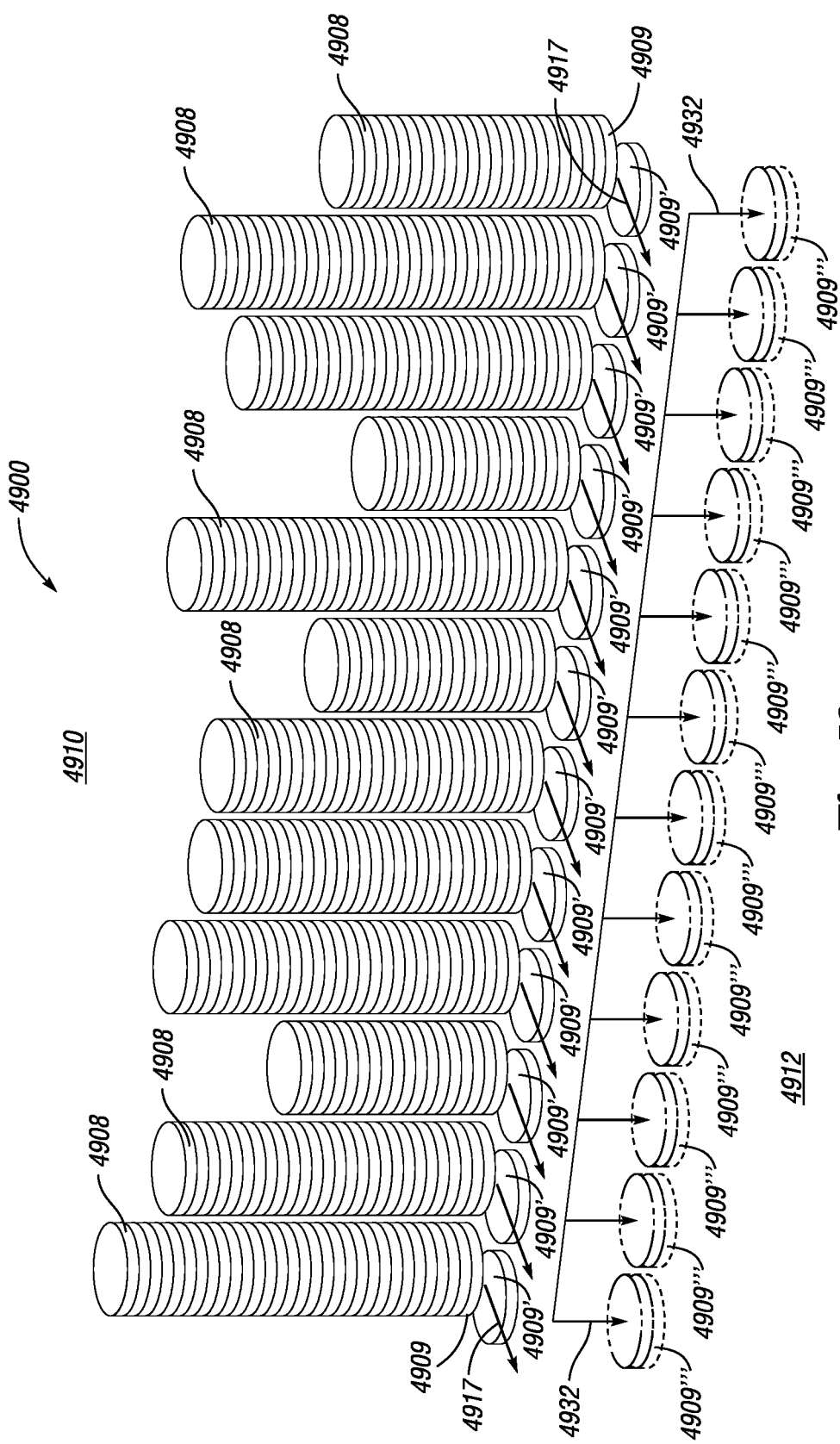
FIG. 50 illustrates a schematic perspective view of a gaming chip disinfecting unit including a stack separator mechanism according to the embodiments of the present invention.

FIG. 50 illustrates a schematic perspective view of the gaming chip disinfecting unit 4900 including a stack separator mechanism embodiment of the present invention during gaming chip 4908 movement to a first disinfecting position 4909 to a second ejecting position 4009' and to a final gaming chip resting position 4909''' following most or all UVC disinfecting processing. Initially, gaming chips 4908 are loaded into columns in the load or undisinfected area 4910. It is not necessary for all columns to be stacked with the same number of gaming chips 4908 and may operate with a number of columns entirely empty. As shown, there are 12 columns associated with the gaming chip disinfecting unit 4900 but any number of columns may be included. The ejector 4914 (not shown in this schematic view) pushed gaming chips 4909 forward to a position 4909' just prior to being released into the unload or disinfected area 4912 of gaming chip disinfecting unit 4900 where the gaming chips 4909''' come to rest. Once all gaming chips 4908 have been processed, the gaming chip disinfecting unit 4900 may be opened manually or automatically to remove and return the gaming chips to the game table chip tray. Generally, a game dealer will move the gaming chips 4908 in stacks or columns of chips with the same denomination as opposed to moving chip by chip, to their original position in the game chip tray.

FIG. 51A illustrates a cross section view of a gaming chip disinfecting unit 5100 including a stack separator mechanism embodiment of the present invention in a first position with gaming chips 5108 loaded and ready for UVC disinfection processing by UVC assembly 5131. Gaming chip disinfecting unit 5100 includes housing 5102 and chip support 5103. Preferably, pivotably attached to the chip support 5103 is rotatable door 5104. Alternatively, rotatable door 5104 may be attached to the housing 5102. Those familiar with the art will recognize many alternatives exist for closing the gaming chip disinfecting unit 5100 such as motorized doors, sliding doors, etc. As illustrated, rotatable door 5104 pivots around axis 5106 from a closed position to an open or unloading position 5104'. A magnetic interlock 5136 is provided comprised of primary electronic magnetic interlock component 5140 which is attached to the chip support 5103 and secondary electronic magnetic interlock component 5138 which is attached to rotatable door 5104 to ensure at least the UVC operation of gaming chip disinfecting unit 5100 cannot be activated unless the interlock is in the closed position to reduce any potential exposure to the dealer or operator of the gaming chip disinfecting unit 5100 or others. Although a magnetic interlock is illustrated, those familiar with the art will recognize that there are a wide variety of sensors that may also serve to ensure closure of the gaming chip disinfecting unit 5100 prior to the starting the UVC disinfection operation or process. When the rotatable door 5104 is in the open position 5104', as partially shown, gaming chips 5108 are loaded in a relatively flat orientation 5110', generally, parallel with the bottom surface of gaming chip support 5103. Generally, a game dealer will move the gaming chips 5108 in stacks or columns of chips with the same denomination as opposed to moving chip by chip, to their original position in the game chip tray.

Figure 52:
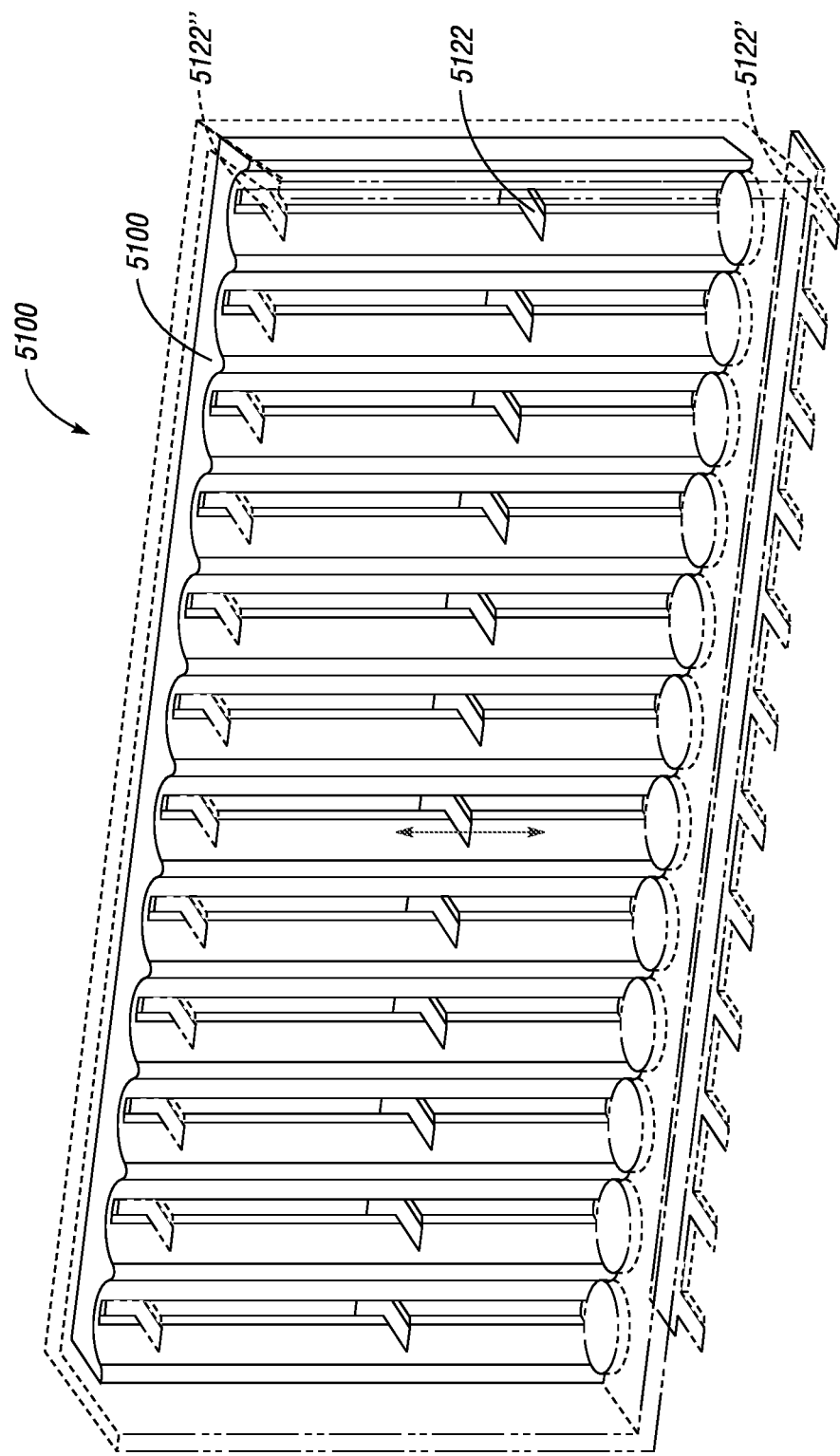
FIG. 52 illustrates a perspective view of a gaming chip disinfecting unit including a stack separator mechanism according to the embodiments of the present invention.

Gaming chip disinfecting unit 5100 includes moveable UVC assembly 5131 and ratchet bar assembly 5118 which preferably move in conjunction with one another as the gaming chips are at least partially disinfected. UVC assembly 5131 and ratchet bar assembly 5118 move parallel relative to the chip support 5103. Parallel travel is provided by mounting to lead screw 5114 which is driven by servo motor 5112. Servo motor 5112 drives lead screw 5114 by any convenient means as well known in the art such as gearing, belts, etc. Preferably, two lead screws 5114 are provided to ensure UVC assembly 5131 and ratchet bar assembly 5118 move consistently while they travel parallel with the chip support 5103. Alternatively, linear bearings or similar may be utilized to ensure consistent and reliable travel parallel with chip support 5103. Upon initiation of the UVC functionality of gaming chip disinfecting unit 5100, gaming chips 5108 have been loaded and supported by chip support 5103. Although the cross-section view of FIG. 51A and FIG. 51B only illustrates a single stack of gaming chips 5108, the gaming chip disinfecting unit 5100 may include a plurality of columns equal to or greater than the number of columns in the gaming chip tray on the table game or if utilized as the chip tray itself, any number of columns may be included but as commonly used in gaming, the number of columns may equal 12 or 15 columns or any other convenient number as will be illustrated in succeeding figures. As illustrated, a UVC light source 5130 is provided to illuminate the individual gaming chips 5110 as they are separated by spring-biased rachet bar 5122 connected to the ratchet bar assembly 5118. Spring-biased rachet bar 5122 are also shown in FIG. 52 as they extend into the chip stacks when present in the Gaming chip disinfecting unit 5100. Base member 5120 supports the spring-biased rachet bar 5122. Although this embodiment of the present invention is illustrated utilizing an elongated mercury UVC lamp 5130, or any suitable UVC light source may be utilized such as UVC LEDs, excimer UVC lamps, or the like. UVC lamp 5130, produces UVC light as shown and focused or directed 5134 to the underside of gaming chip 5110 by use of a UVC directional shield 5132 (shown best in FIG. 51C), although a UVC shield is preferable, it may not always be necessary in all cases. UVC lamp 5130, produces UVC light as shown and focused or directed 5134 only to the underside of gaming chip 5110 at the beginning of the UVC disinfection process. As the UVC assembly 5131 and ratchet bar assembly 5118 travel upwards on lead screw 5114, UVC assembly illuminate both the underside of an upper gaming chip 5110 and the top of lower gaming chip 5909'. This UVC disinfection of dual gaming chips continues throughout the gaming chip stack 5108 until the UVC assembly 5131 and ratchet bar assembly 5118 have reached the top gaming chip in the stack or traveled to a predetermined maximum upper travel at which time only the upper surface of top gaming chip will be exposed to the UVC illumination. Those familiar with the art will recognize while the upper surface of a lower gaming chip 5110' and lower surface of an upper gaming chip 5110 are the primary targets of UVC disinfection of focused or directed by UVC shield 5132, UVC illumination will intentionally disperse from these targets via reflection to illuminate edges of gaming chips 5108, thereby at least partially disinfect all surface of gaming chips 5108. Those familiar with the art will recognize that certain materials will respond differently to UVC lighting and may affect material selection such as aluminum for reflective properties as opposed to stainless steel which is nonreflective of UVC light or other materials discussed herein. In this and other embodiments, it may be advantageous to utilize a reflective material to assist in providing UVC illumination to all areas of the disinfection target while other UVC illumination may be restricted utilizing nonreflective materials.

FIG. 51B illustrates a cross section view of the gaming chip disinfecting unit 5100 including the stack separator mechanism embodiment of the present invention in a second position. As shown, UVC assembly 5131 and ratchet bar assembly 5118 have progressed upward to a midpoint of the stack of gaming chips 5108 and will continue until reaching the top of the stack of gaming chips 5108 as represented by UVC assembly 5131" and ratchet bar assembly 5118". In this manner, each gaming chip 5108 is sterilized. The ratchet bar assembly 5118 may progress continuously up the stack of gaming chips 5108 or may pause between each pair of neighboring gaming chips 5108 to provide a proper amount of UVC light.

FIG. 51C illustrates a detailed close-up, side view of a portion of the gaming chip disinfecting unit 5100, namely the UVC assembly 5131 and ratchet bar assembly 5118 and portion of the gaming chip stack. As the spring-biased rachet bar 5122 moves upward in the chip stack a space 5134 is created to allow UVC light to disinfect the top of one chip and the bottom of a neighboring chip. Relative distance D1 represents the width of the gaming chip 5110' at the beginning of a disinfection cycle when it is in a relatively horizontal position relative to the housing. As ratchet bar assembly 5118 travels upward, it will angularly lift the chip 5110 whereas the horizontal distance D1 decreases to a relative distance D2 which only engages a slight edge of the chip. During this time of chip movement, the bottom of chip 5110 is at least partially disinfected. As the ratchet bar assembly 5118 continues to travel upward, the angularity 5144 increases and relative distance D2 continues to decrease until such time the chip 5110' has been released and returns to a relatively horizontal relationship with the housing bottom whereas the top of the chip will be at least partially disinfected. After the chip 5110' has dropped to the relatively horizontal relationship with the housing, the ratchet bar assembly 5118 will then engage the next chip in the stack and the process is repeated until the entire stack has been disinfected. Once the stack has been disinfected and the ratchet bar assembly 5118 no longer engages any chips, the ratchet bar assembly 5118, along with the UVC assembly 5131, moves downward to a starting position below the first chip in the stack. During this downward travel, ratchet bar assembly 5118 is allowed to rotate about axis 5124 against the spring bias of torsion spring 5126 in order to clear the gaming chips 5110 during its downward travel.

As shown in FIGS. 51A-51C, once the stack has been disinfected and the ratchet bar assembly 5118 no longer engages any chips, the ratchet bar assembly 5118, along with the UVC assembly 5131, moves downward to a starting position below the first chip in the stack. During this downward travel, ratchet bar assembly 5118 is allowed to rotate about axis 5124 against the spring bias of torsion spring 5126 in order to clear the at least partially disinfected gaming chips 5110 during its downward travel to an initial or home position whereas it is positioned to begin another cycle of disinfecting chips.

Figure 53:
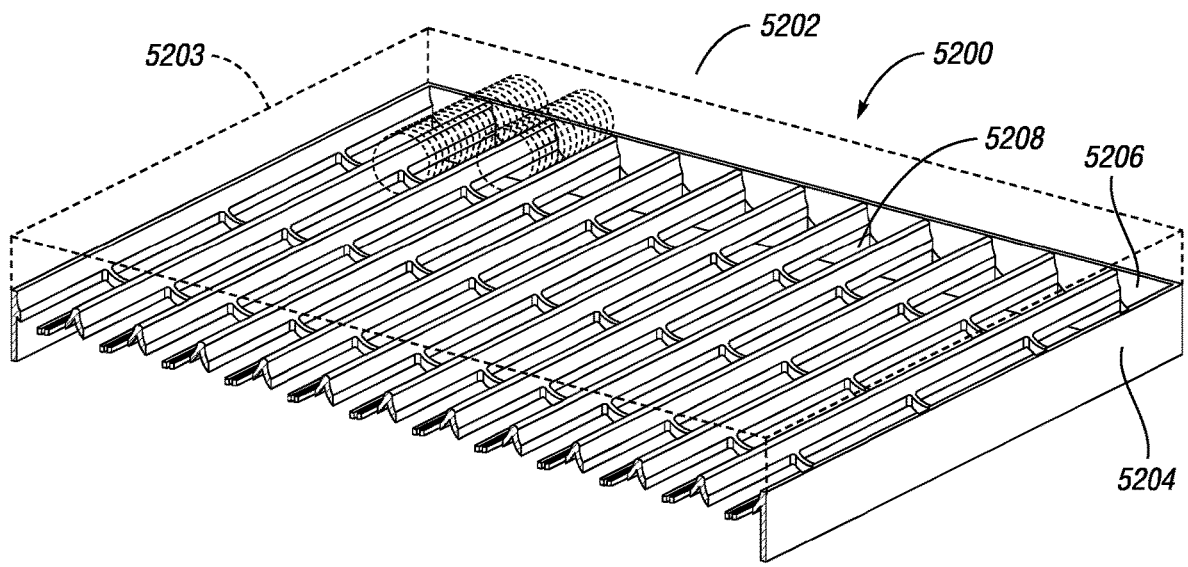
FIG. 53 illustrates an upper perspective view of a gaming chip disinfecting unit including a stack separator mechanism according to the embodiments of the present invention.
Figure 54:
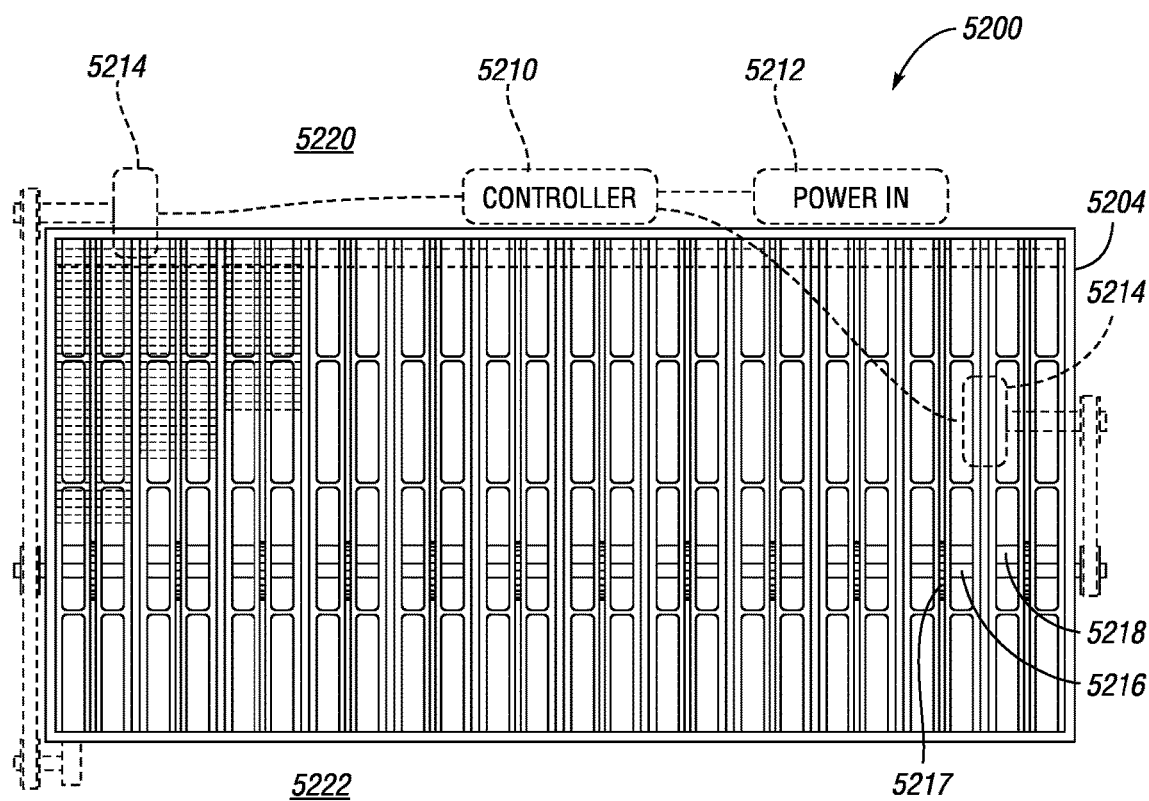
FIG. 54 illustrates a top plan view of a gaming chip disinfecting unit including a stack separator mechanism according to the embodiments of the present invention.

FIGS. 53-55 illustrate perspective and top plan views of a gaming chip disinfecting unit 5200 including a stack separator mechanism. In this embodiment, the gaming chips 5202 are sterilized while positioned in horizontal rows rather than in stacked columns. The gaming chip disinfecting unit 5200 comprises a housing/tray 5204 defining one or more channels 5206 configured to retain gaming chips 5202 in horizontal rows as best seen in FIG. 53. The bottom surface of the channels 5206, on which the gaming chips 5202 rest, include multiple elongated openings 5208 configured to provide access to a stack separator mechanism associated with the gaming chip disinfecting unit 5200 and provide apertures for allowing UVC illumination from below the housing 5204. Those familiar with the art will recognize that the gaming chip disinfection unit 5200 may alternatively be placed above the housing 5204 and gaming chips 5202 and act upon the top of the gaming chips. In another embodiment, each valley 5206 may include a single, elongated opening rather than multiple elongated openings 5208. While not shown, during sterilization a cover may be positioned over the housing 5204.

In this embodiment, the stack separator mechanism includes broadly a controller 5210, power source 5212, one or more motors 5214, shaft 5216 and UVC light source assembly 5218. Controller 5210 controls simultaneous movement of the shaft 5216 and UVC light source assembly 5218. The shaft 5216 and UVC light source assembly 5218 extend generally a width of the housing 5204 to disinfect multiple rows of gaming chips 5204. In a sterilization mode, the shaft 5216 and UVC light source assembly 5218 collectively move from a first side 5222 of the gaming chip disinfecting unit 5200 to a second side 5220 of the gaming chip disinfecting unit 5200 proximate a dealer position. While it is preferable to begin a disinfection cycle at the side opposite the dealer side, conversely, the disinfection cycle may begin at the dealer side of housing 5204 In practice, as shown best in FIGS. 56A-59D, as the shaft 5216 rotates and moves, the shaft 5216 along with associated wheels 5217 serve to separate neighboring gaming chips 5202 so that the UVC light source assembly 5218 may sterilize upper and lower surfaces of the gaming chips 5202.

Figure 56A:
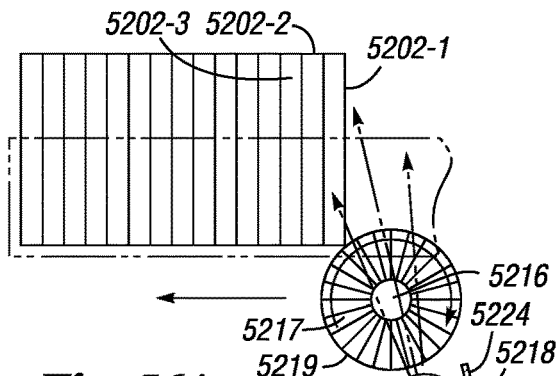
FIG. 56A illustrates a schematic side view of a gaming chip disinfecting unit including a rotating stack separator mechanism according to the embodiments of the present invention in a first position manipulating a first gaming chip.
Figure 57A:
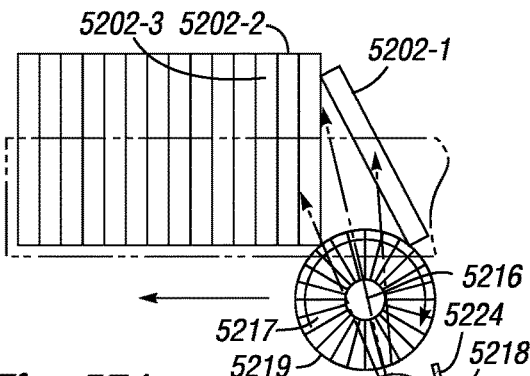
FIG. 57A illustrates a schematic side view of a gaming chip disinfecting unit including a rotating stack separator mechanism according to the embodiments of the present invention in a first position manipulating a second gaming chip.
Figure 56B:
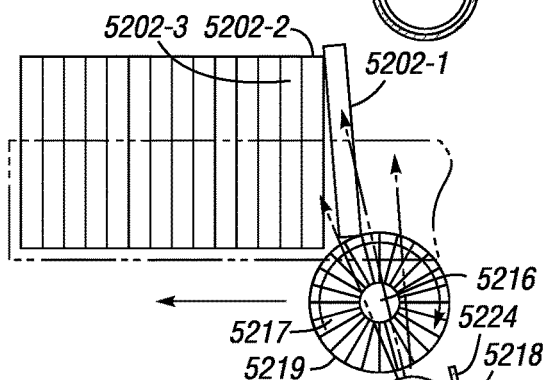
FIG. 56B illustrates a schematic side view of a gaming chip disinfecting unit including a rotating stack separator mechanism according to the embodiments of the present invention in a second position manipulating a first gaming chip.
Figure 57B:
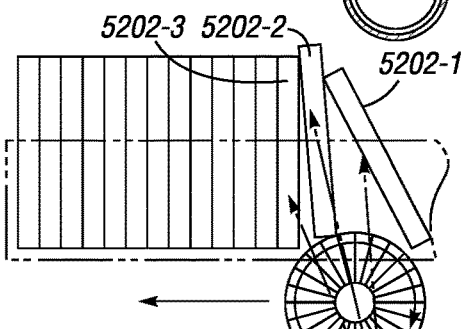
FIG. 57B illustrates a schematic side view of a gaming chip disinfecting unit including a rotating stack separator mechanism according to the embodiments of the present invention in a second position manipulating a second gaming chip.
Figure 56C:
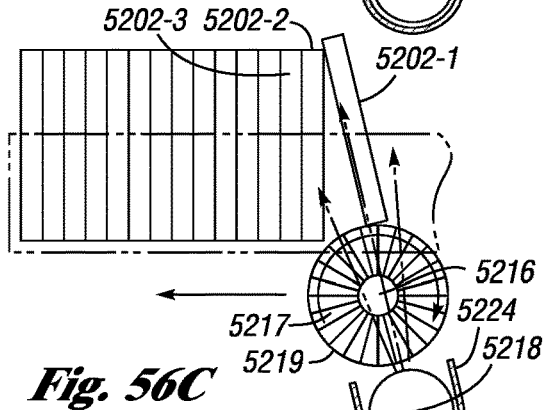
FIG. 56C illustrates a schematic side view of a gaming chip disinfecting unit including a rotating stack separator mechanism according to the embodiments of the present invention in a third position manipulating a first gaming chip.
Figure 57C:
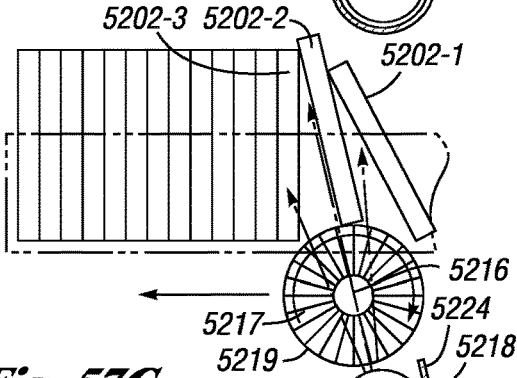
FIG. 57C illustrates a schematic side view of a gaming chip disinfecting unit including a rotating stack separator mechanism according to the embodiments of the present invention in a third position manipulating a second gaming chip.
Figure 56D:
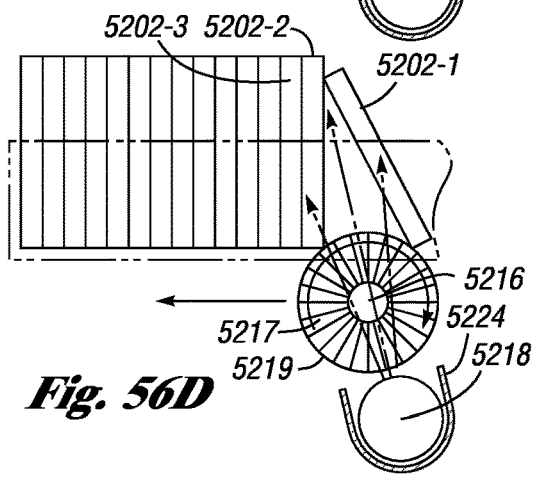
FIG. 56D illustrates a schematic side view of a gaming chip disinfecting unit including a rotating stack separator mechanism according to the embodiments of the present invention in a fourth position manipulating a first gaming chip.
Figure 57D:
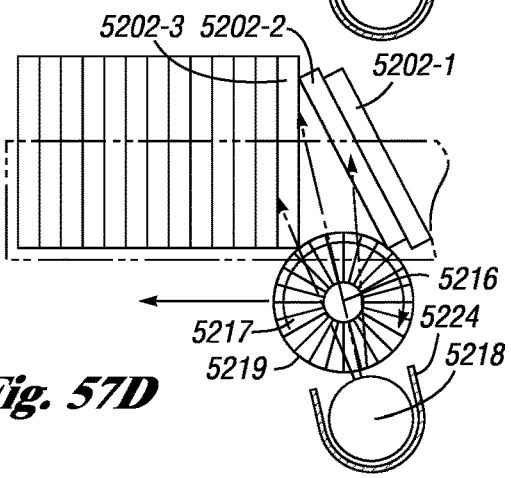
FIG. 57D illustrates a schematic side view of a gaming chip disinfecting unit including a rotating stack separator mechanism according to the embodiments of the present invention in a fourth position manipulating a second gaming chip.
Figure 58A:
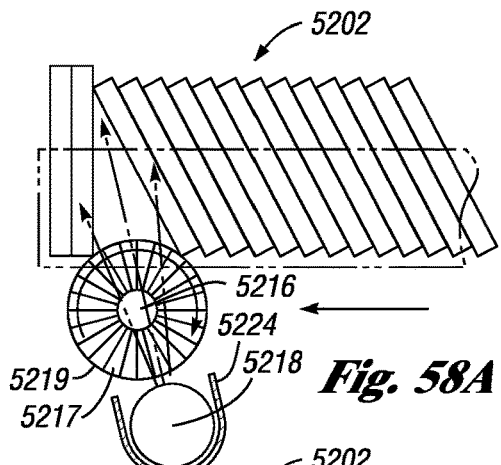
FIG. 58A illustrates a schematic side view of a gaming chip disinfecting unit including a rotating stack separator mechanism according to the embodiments of the present invention in a first position manipulating a later stage gaming chip.
Figure 59A:
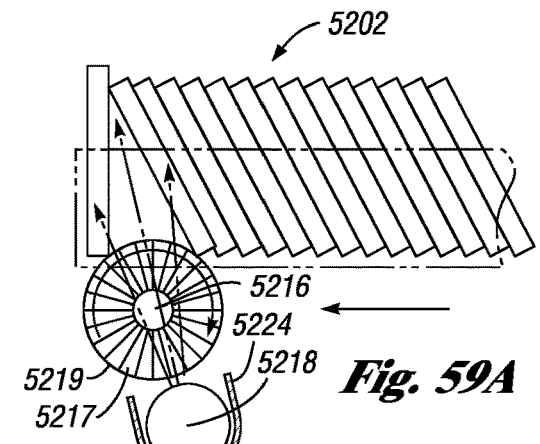
FIG. 59A illustrates a schematic side view of a gaming chip disinfecting unit including a rotating stack separator mechanism according to the embodiments of the present invention in a first position manipulating a final gaming chip.
Figure 58B:
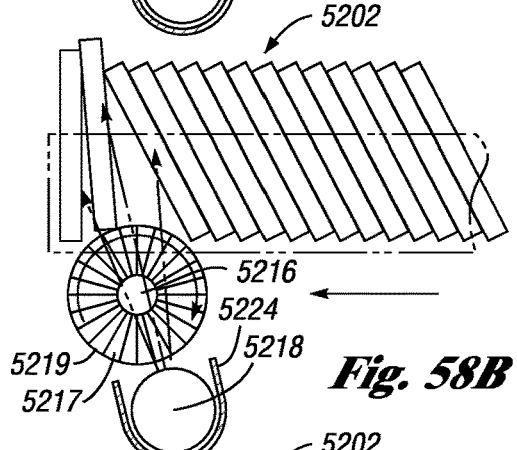
FIG. 58B illustrates a schematic side view of a gaming chip disinfecting unit including a rotating stack separator mechanism according to the embodiments of the present invention in a second position manipulating a later stage gaming chip.
Figure 59B:
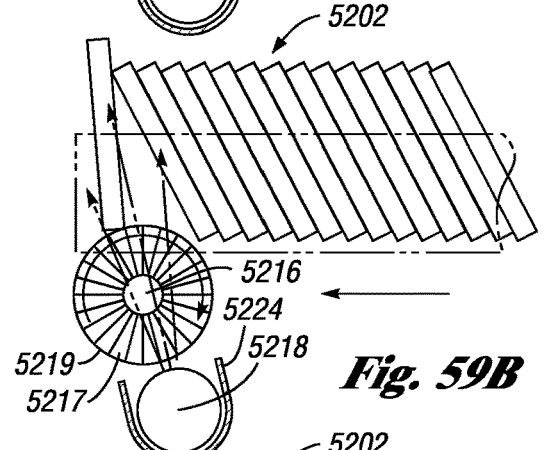
FIG. 59B illustrates a schematic side view of a gaming chip disinfecting unit including a rotating stack separator mechanism according to the embodiments of the present invention in a second position manipulating a final gaming chip.
Figure 58C:
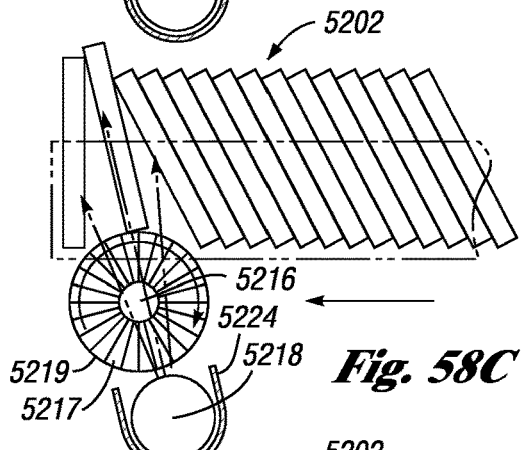
FIG. 58C illustrates a schematic side view of a gaming chip disinfecting unit including a rotating stack separator mechanism according to the embodiments of the present invention in a third position manipulating a later stage gaming chip.
Figure 59C:
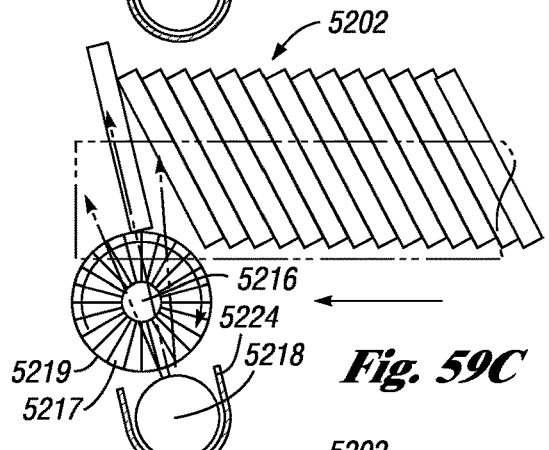
FIG. 59C illustrates a schematic side view of a gaming chip disinfecting unit including a rotating stack separator mechanism according to the embodiments of the present invention in a third position manipulating a final gaming chip.
Figure 58D:
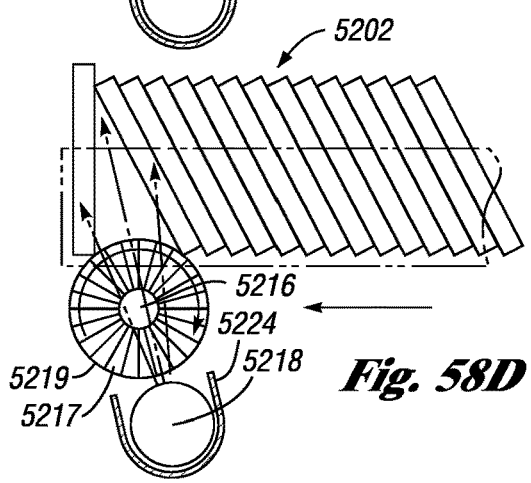
FIG. 58D illustrates a schematic side view of a gaming chip disinfecting unit including a rotating stack separator mechanism according to the embodiments of the present invention in a fourth position manipulating a later stage gaming chip.
Figure 59D:
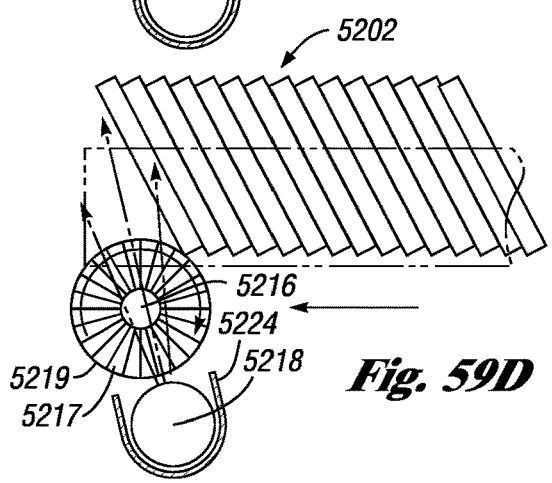
FIG. 59D illustrates a schematic side view of a gaming chip disinfecting unit including a rotating stack separator mechanism according to the embodiments of the present invention in a fourth position manipulating a final gaming chip.

FIGS. 56A-56D illustrate a cross-sectional view of the gaming chip disinfecting unit 5200 in operation. FIG. 56A illustrates the starting point of the shaft 5216 along with associated wheels 521 and UVC light source assembly 5218. The UVC light source assembly 5218 includes a shield or reflector 5224 for directing the UVC light towards the gaming chips 5202. In one embodiment, the reflector 5224 is fabricated of polished aluminum or similar material to reflect the UVC light in the proper direction. While reflector 5224 may assist in directing the UVC illumination, it is not always necessary for the sterilization process. The housing 5204 and/or cover may also incorporate reflective surfaces to increase the effectiveness of the UVC light. At this stage, the UVC light source assembly 5218 and reflector 5224 is directing UVC light onto a first surface of gaming chip 5202-1. Now referencing FIG. 56B, once controller 5210 triggers the one or more motors 5214 to activate responsive to a user input, the shaft 5216 along with associated wheels 5217 and UVC light source assembly 5218 begin jointly moving toward a dealer position (i.e., away from players). As the shaft 5216 rotates along with associated wheels 5217 (clockwise as shown) and move longitudinally, a first gaming chip 5202-1 is contacted by an outer surface 5219 of the wheel 5217. The outer surface 5219 of the wheel is ideally fabricated of a non-slip material (e.g., high friction rubber) and/or includes protrusions, roughened portions, or other surface treatments to facilitate non-slip interaction with the gaming chips 5202. As the shaft 5216 along with associated wheels 5217 continues moving longitudinally and rotating, the wheel 5217 causes the first gaming chip 5202-1 to separate from a neighboring gaming chip 5202-2 thereby allowing UVC light from the UVC light source assembly 5218 to treat both a second surface of gaming chip 5202-1 and a first surface of gaming chip 5202-2.

FIGS. 57A-57D illustrate the shaft 5216 and UVC light source assembly 5218 continuing to move longitudinally such that the second gaming chip 5202-2 has been moved so that a second surface thereof may be treated along with a first surface of a third gaming chip 5202-3. As shown in FIGS. 58A-59D, this process continues until all gaming chips 5202 in the row are treated. As described above relative to other embodiments, the controller 5210 may cause the shaft 5216 along with associated wheels 5217 and UVC light source assembly 5218 to move continuously or may pause when neighboring gaming chips are separated so that the UVC light is permitted to treat the surfaces for a pre-established period of time.

Figure 60:
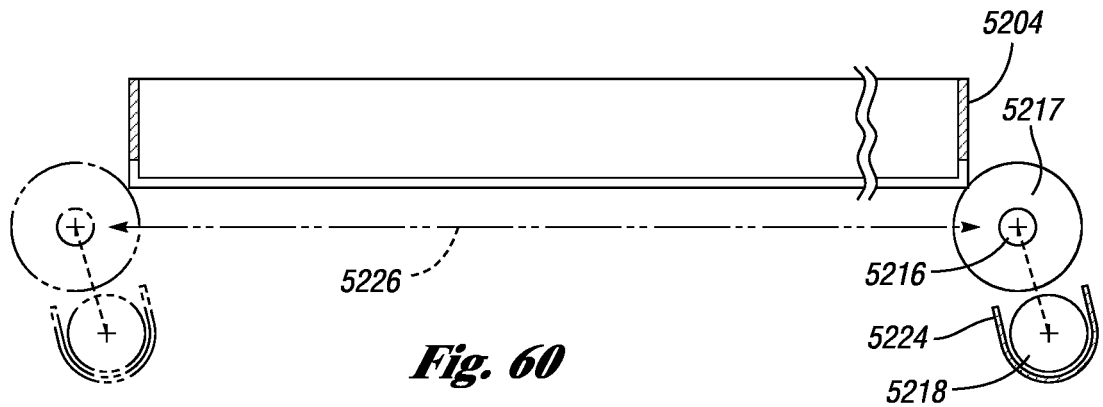
FIG. 60 illustrates a schematic side cross section view of a gaming chip disinfecting unit illustrating the movement of the stack separator carriage movement from a starting position, ending position and back to a starting position according to the embodiments of the present invention.
Figure 61:
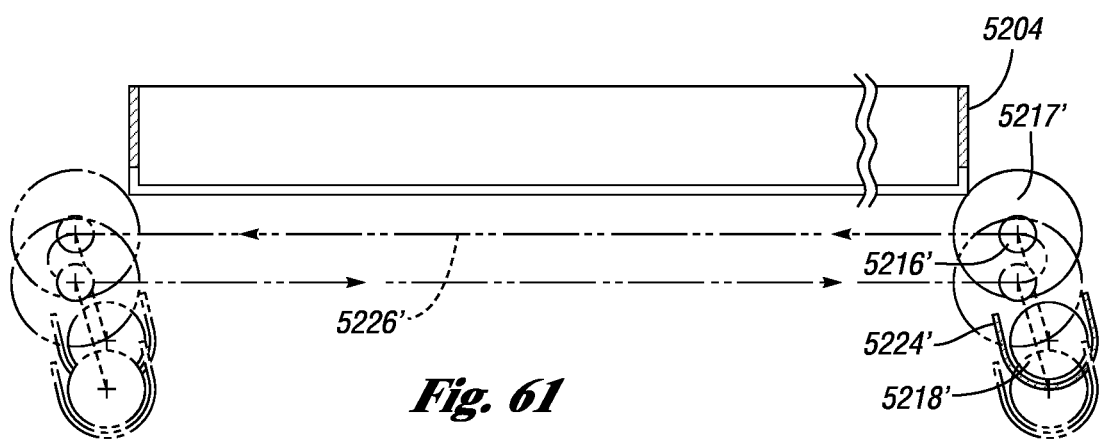
FIG. 61 illustrates a schematic side cross section view of a gaming chip disinfecting unit illustrating a second, different movement of the stack separator carriage movement from a starting position, ending position and back to a starting position according to the embodiments of the present invention.
Figure 62:
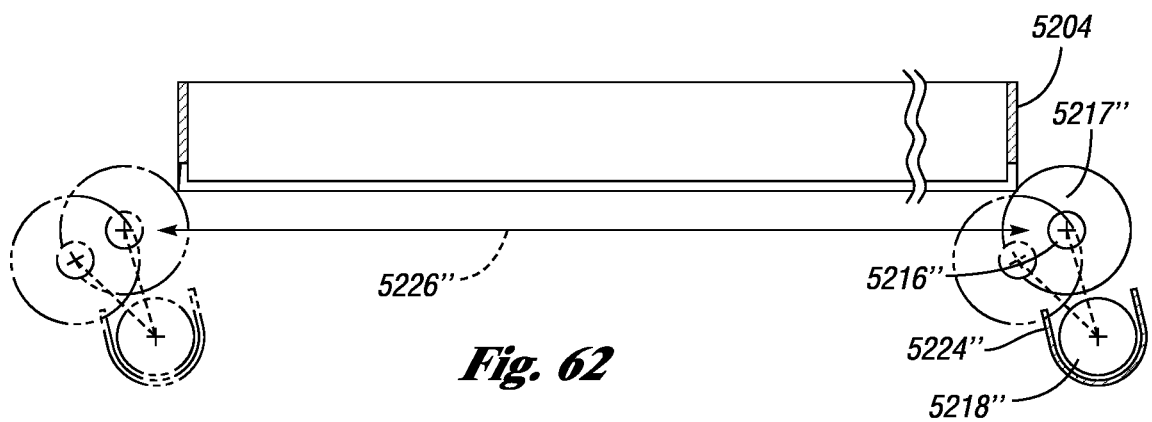
FIG. 62 illustrates a schematic side cross section view of a gaming chip disinfecting unit illustrating a third, different movement of the stack separator carriage movement from a starting position, ending position and back to a starting position according to the embodiments of the present invention.

FIGS. 60-62 illustrate cross-sectional views of the housing 5204, shaft 5216 and UVC light source assembly 5218. More particularly, FIG. 60 illustrates a path 5226 traveled by the shaft 5216 and UVC light source assembly 5218 during the gaming chip sterilization process and its return to an initial or home/start position. A home/start position of the shaft 5216 is represented to the right in full lines and a finish position is represented at the left in broken lines. When in the sterilization mode, the shaft 5216 and UVC light source assembly 5218 are in a first up position such that the shaft 5216 contacts the gaming chips 5202 as detailed above. FIGS. 61 and 62 illustrate the shaft 5216' and UVC light source assembly 5218' in a lowered position for returning to the home/start position during which the shaft 5216' does not contact the gaming chips 5202.

Figure 63:
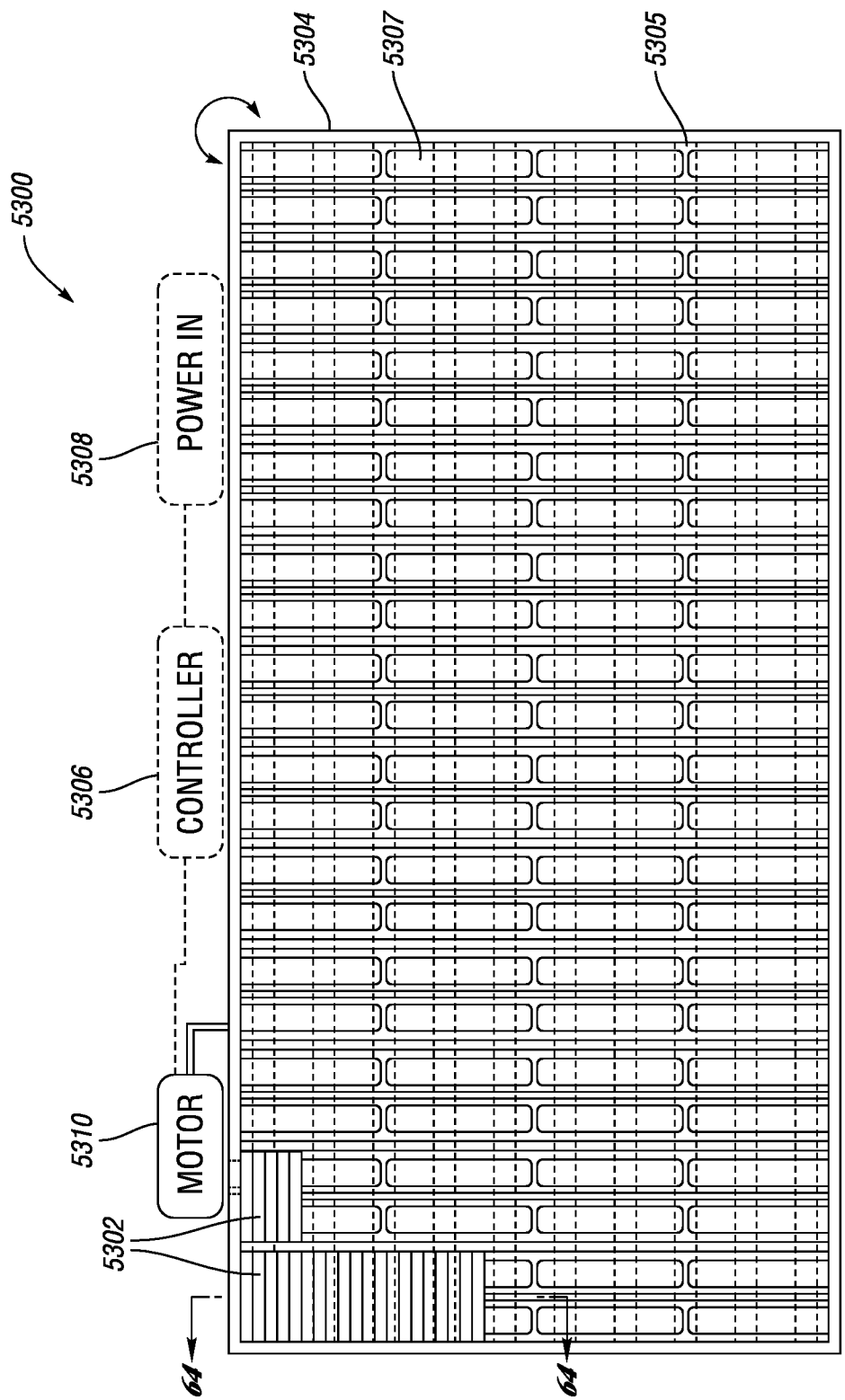
FIG. 63 illustrates a top plan view of a gaming chip disinfecting unit including a vibratory gaming chip separator mechanism according to the embodiments of the present invention.

FIG. 63 is a top down view of another embodiment of a gaming chip disinfecting unit 5300 which relies on vibration to separate neighboring gaming chips 5302 positioned in horizontal rows within a housing/tray 5304. The housing 5304 defines one or more channels 5207 for retaining horizontally stacked gaming chips 5302. In this embodiment, a stack separator mechanism includes broadly a controller 5306, power source 5308 and one or more vibration motors 5310. Those skilled in the art will recognize that the vibration may also be created by separate devices (e.g., shaker devices) driven by the one or more motors 5310. The one or more vibration motors 5310 serve to vibrate the housing 5304 and gaming chips 5302 positioned therein. In one embodiment, the one or more vibration motors 5310 vibrate the housing 5304 within a horizontal plane (i.e., two dimensions). It is conceivable that the one or more vibration motors 5310 may also vibrate the housing in three dimensions.

Figure 64A:
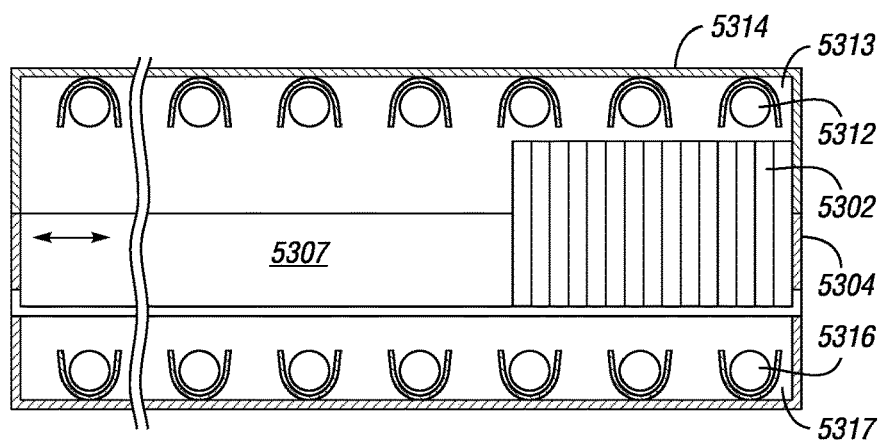
FIG. 64A illustrates a schematic side view of a gaming chip disinfecting unit including a vibratory gaming chip stack separator mechanism according to the embodiments of the present invention in a first position prior to any vibratory gaming chip stack separation.
Figure 64B:
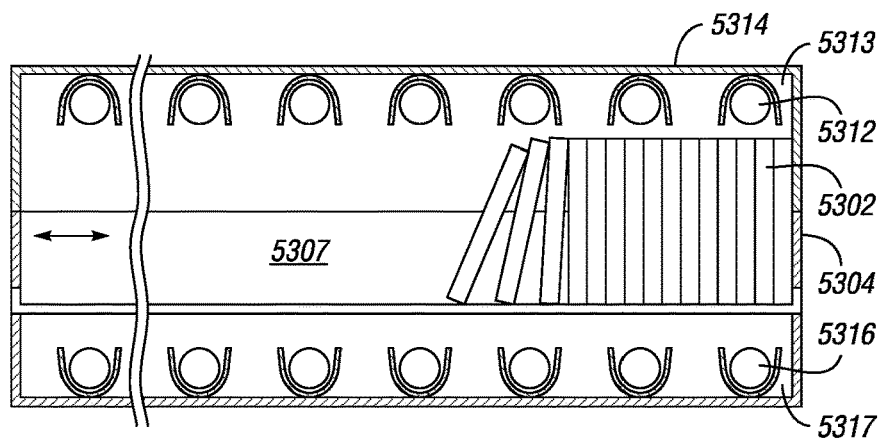
FIG. 64B illustrates a schematic side view of a gaming chip disinfecting unit including a vibratory gaming chip stack separator mechanism according to the embodiments of the present invention in a second position as the vibratory gaming chip stack separation begins.
Figure 64C:
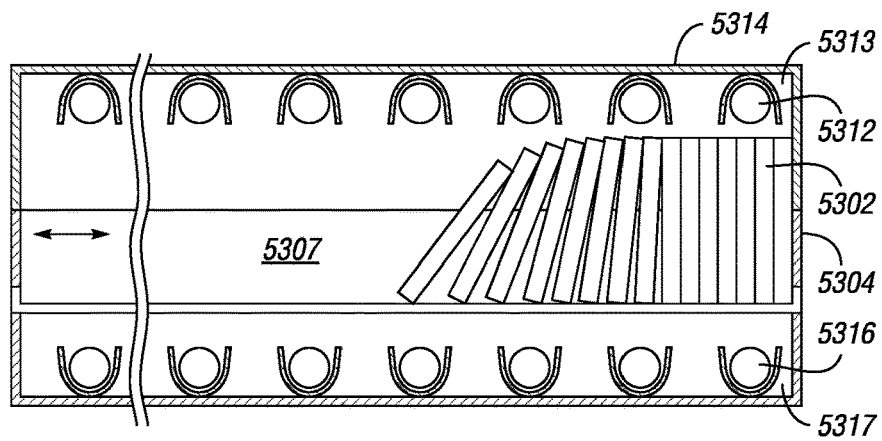
FIG. 64C illustrates a schematic side view of a gaming chip disinfecting unit including a vibratory gaming chip stack separator mechanism according to the embodiments of the present invention in a third position as the vibratory gaming chip stack separation continues.
Figure 64D:
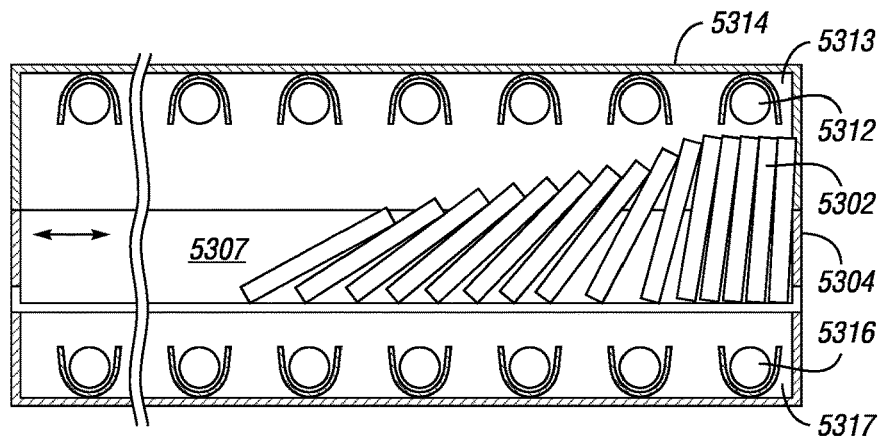
FIG. 64D illustrates a schematic side view of a gaming chip disinfecting unit including a vibratory gaming chip stack separator mechanism according to the embodiments of the present invention in a fourth position as the vibratory gaming chip stack separation further continues.

FIGS. 64A-64D illustrate cross-sectional views of the housing 5304 with gaming chips 5302 in one of the defined channels 5207. Upper UVC light sources 5312 are positioned on an under surface of a cover 5314 and lower UVC light sources 5316 are positioned beneath the channels 5207. Once controller 5306 triggers the one or more vibration motors 5310 to activate responsive to a user input, the vibration motors 5310 vibrate the housing 5304 causing the gaming chips 5302 to begin moving from an original compact stack, as shown in FIG. 64A, to a more separated arrangement as shown in FIGS. 64B-64D. As the gaming chips 5302 begin to move and separate, the upper UVC light sources 5312 and lower UVC light sources 5316 are able to act on upper and lower surfaces of the gaming chips 5302. As shown, the gaming chips 5302 are moving away from a dealer position but depending on a stacking arrangement, may move toward the dealer position. The vibration mode may be activated for a period time until the gaming chips 5302 have separated as much as they can and generally cover the bottom of the channel 5306.

FIG. 65 illustrates a cross section side view of an electronic gaming machine 5400 illustrating various placement options for UVC disinfection bars 5402-1 through 5402-4. As shown, a first UVC disinfection bar 5402-1 is placed near the game interface area 5404 at a bottom of primary game display 5406, a second UVC disinfection bar 5405-2 is placed near a top of the primary game display 5406, a third UVC disinfection bar 5405-3 is placed near a top of a bonus game display 5408 and a fourth UVC disinfection bar 5405-4 is placed near the top 5410 of the electronic gaming machine 5400. In each instance, the UVC disinfection bars 5402-1 through 5402-4 include a lip 5412-1 through 5412-4 extending downward from UVC disinfection bar housings 5414-1 through 5414-4. The lips 5412-1 through 5412-4 guide the UVC light onto the electronic gaming machine 5400 while limiting UVC light from being directed at areas around the electronic gaming machine 5400. While four UVC disinfection bars 5402-1 through 5402-4 are shown, it is well understood that more or less than four UVC disinfection bars 5402-1 through 5402-4 may be installed on an electronic gaming machine 5400 without departing from the spirit and scope of the present invention. Often, and preferably, only one UVC disinfection bar is necessary to perform the disinfection operation, depending on time and/or intensity. Moreover, electronic gaming machines are manufactured in a wide variety of sizes and configurations. Accordingly, one or more of the locations shown or others not shown, will suit one electronic gaming machine better than others while a different location will suit a different electronic gaming machine better.

In another embodiment, sensors attached to or associated with UVC disinfection bars on are in communication such that UVC disinfection bars on any electronic gaming machine are not activated until no players or other persons are at or near the electronic gaming machines to be disinfected. Many such sensors are well known, such as proximity sensors, motion detections, optical sensors and the like. In this manner, there is little or no risk that a player playing or seated at an electronic gaming machine is subjected to UVC light from UVC disinfection bars activated==. In many instances, multiple sensors may be provided to further ensure safety and redundancy in detection. A controller (not shown) may control the UVC light sources responsive to sensor outputs. Alternatively, the UVC lights sources may turn on and off based on directly receiving the sensor outputs. In operation, the UVC disinfection bar may be utilized on a continual basis or preferably may operate at shorter time cycles to further ensure safety for humans at the electronic gaming machine which is the target of disinfection or adjacent electronic gaming machines or other humans. Those familiar with the art will understand that electronic gaming machines are placed in many different style configurations with some side-by-side configurations offering little or no space therebetween. Further, the sensors will alert the controller that a player has taken a seat at the electronic gaming machine at which time the UVC disinfection bar will automatically turn off, if it was previously on or stays offs if it was previously off. When the player has left their seat at the electronic gaming machine, the sensors will communicate with the controller to start a disinfecting cycle or wait a predetermined time to start a disinfecting cycle. The disinfecting cycle time may be predetermined or determined by the time and/or intensity of the UVC exposure to at least partially disinfect the target area. In another embodiment, the controller is configured to activate said one or more UVC light sources responsive to one or more outputs of said one or more sensors indicating that a person proximate to the electronic machine is no longer proximate to the electronic machine. That is, to protect all persons, including non-players, the UVC light sources may not activate until the potential UVC exposure area surrounding the electronic gaming machine is clear. The potential UVC exposure area may be at least partially managed by using the reflectors, deflectors and baffles. In one embodiment, the controller provides only one or a limited number of disinfecting cycles between players and other persons being nearby since once the electronic gaming machine is at least partially disinfected, there is little or no need for further disinfection and such limited UVC disinfection cycles limit possible exposure to surrounding areas, players and/or staff. Those familiar with the art will recognize that partially or fully automatic or automated UVC disinfection assemblies of this type may be utilized on other or similar machines and devices where public safety is a concern or a plurality of persons may potentially enter or be in the disinfection area. The actual minimum safe physical area or distances from the UVC light source relative to exposure times may be determined by maximum human exposure limits and times as prescribed by the EPA, FDA or other regulatory bodies.

Figure 66:
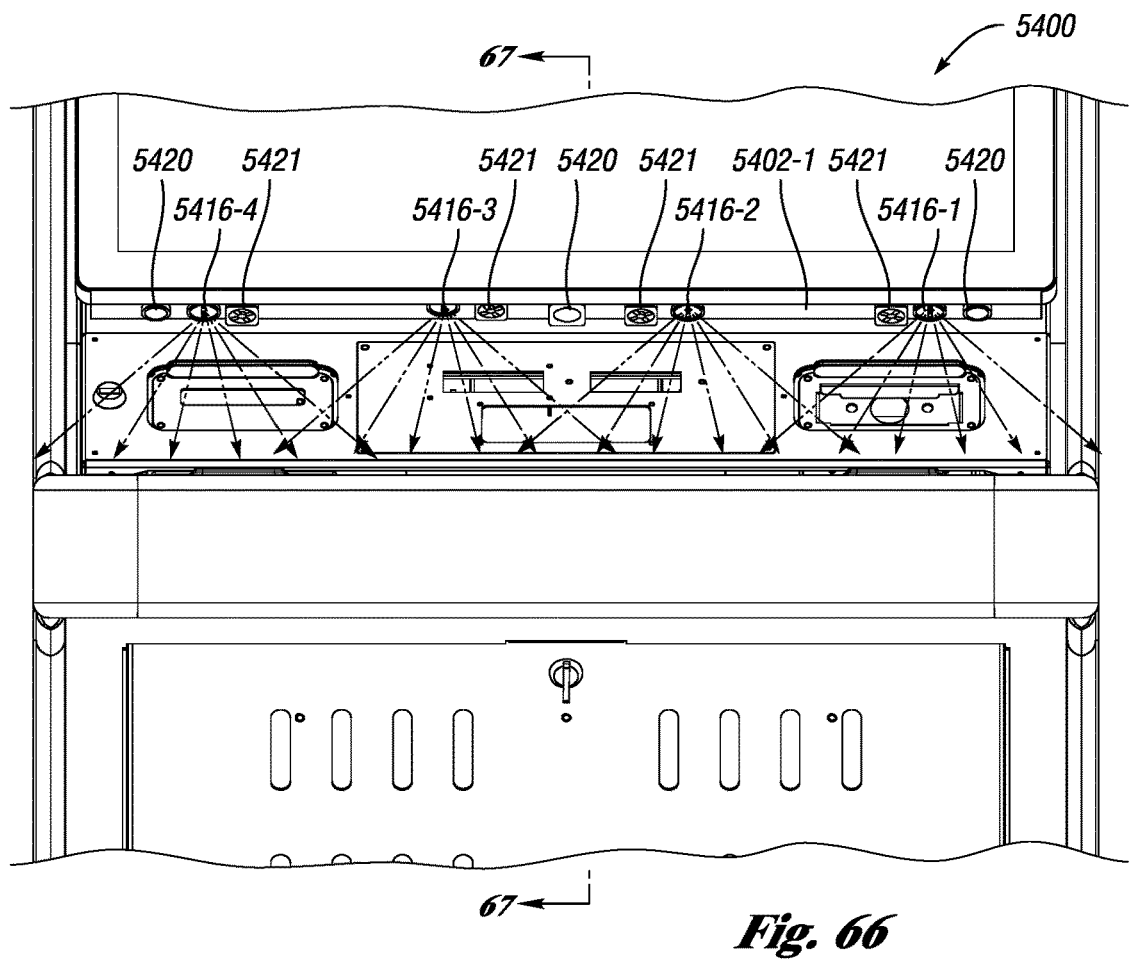
FIG. 66 illustrates a partial broken away front elevation view of an electronic gaming machine further illustrating the UVC light dispersion paths of UVC lighting of a UVC disinfection bar according to the embodiments of the present invention.

FIG. 66 illustrates a front view of the electronic gaming machine 5400 illustrating UVC light being provided by UVC disinfection bar 5402-1 near the game interface area 5404. In this instance, the UVC disinfection bar 5402-1 incorporate four UVC light sources 5416-1 through 5416-4 which effectively cover the game interface area 5404, a plurality of sensors 5420 and a plurality of cooling fans 5421. As shown by the directional arrows, the UVC illumination provided by the UVC light sources 5416-1 through 5416-4 illuminates a somewhat wide area or general cone of illumination as schematically shown. This cone of illumination is not exact and only intended to schematically show the primary areas of illumination as these are the areas of generally higher intensity.

Figure 67:
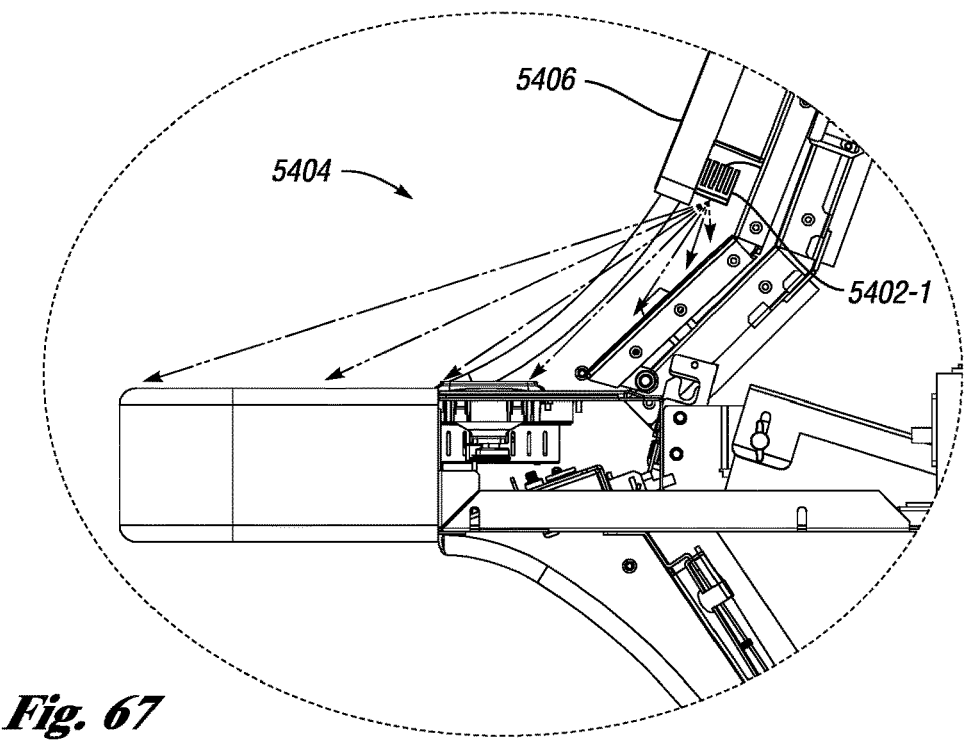
FIG. 67 illustrates a partial broken away side elevation view of an electronic gaming machine further illustrating the UVC light dispersion paths of UVC lighting of a first UVC disinfection bar according to the embodiments of the present invention.
Figure 68:
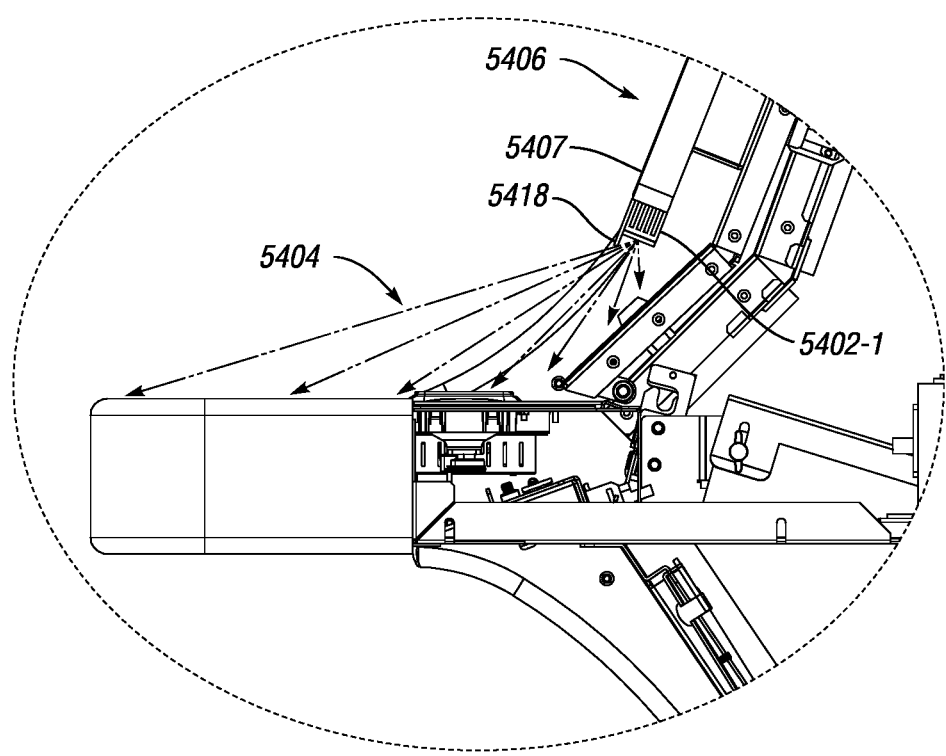
FIG. 68 illustrates a partial broken away side elevation view of an electronic gaming machine further illustrating the UVC light dispersion paths of UVC lighting of a second UVC disinfection bar according to the embodiments of the present invention.
Figure 69:
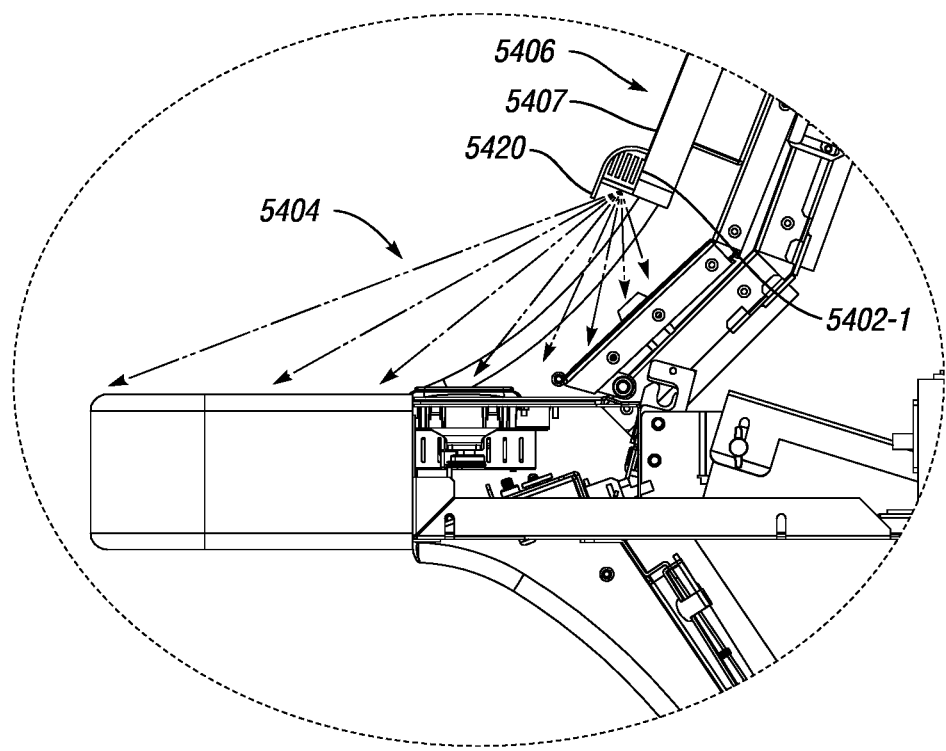
FIG. 69 illustrates a partial broken away side elevation view of an electronic gaming machine further illustrating the UVC light dispersion paths of UVC lighting of a third UVC disinfection bar according to the embodiments the present invention.

FIGS. 67-69 illustrate cross-sectional views as identified by arrows 67 shown in FIG. 66. FIG. 67 illustrates a first placement position for UVC disinfection bar 5402-1 behind a bottom edge of the primary game display 5406 near the game interface area 5404. In this instance, the primary game display 5406 acts a barrier limiting UVC light from extending beyond the game interface area 5404. FIG. 68 illustrates a second placement position for UVC disinfection bar 5402-1 on a bottom edge of the primary game display 5406. In this instance, the UVC disinfection bar 5402-1 includes a lip 5418 which acts as a barrier limiting UVC light from extending beyond the game interface area 5404. FIG. 69 illustrates a third placement position for UVC disinfection bar 5402-1 on a bottom, front portion of the primary game display 5406. In this instance, the UVC disinfection bar 5402-1 includes a lip 5420 which acts as a barrier limiting UVC light from extending beyond the game interface area 5404. A purpose of such barriers is to limit or at least partially direct the UVC illumination generally to the electronic gaming machine surfaces to be disinfected while limiting exposure to surrounding areas.

In one embodiment, as shown in FIGS. 70-72, the UVC disinfection bars 5402-1 through 5402-4 are activated responsive to motion and proximity sensor outputs indicating that no player is playing or seated at the electronic gaming machine 5400. In one embodiment, motion sensors and proximity sensors may be electrically connected in parallel so that if type of sensor fails, the other sensors will continue to provide output or in the alternative is series so that if any sensor fails the UVC disinfection bar will immediately cease operation In one embodiment, the UVC disinfection bars 5402-1 through 5402-4 may be activated for 3-6 minutes to effectively sterilize portions of the electronic gaming machine 5400. The at least partially disinfection activation time may vary by the time and/or intensity of the UVC illumination provided by the UVC disinfection bar.

FIGS. 70-72 illustrate perspective views of UVC disinfection bars according to different embodiments of the present invention. FIG. 70 illustrates a perspective view of a UVC disinfection bar 5500 utilizing four UVC LED modules 5502, four cooling fans 5504, three sensors 5506 and a controller PCB. As described above, the three sensors may be proximity sensors, motion sensors, optical sensors, similar function sensors or any combination thereof. The objective of the sensors 5506 is to determine when no player is seated at the electronic gaming machine 5400 so that the sterilization process may begin. It is not enough to know that the electronic gaming machine 5400 is not being played because players and persons sit at machines even if not playing. UVC disinfection bar 5500 optionally also incorporates a lip 5508 to block UVC light generated by the UVC LED modules 5502.

FIG. 71 illustrates a perspective view of a UVC disinfection bar 5600 utilizing a plurality of individual UVC LEDs 5602, two cooling fans 5604 and five sensors 5606 as previously described. In one embodiment, the individual UVC LEDs 5602 may project different colors for purposes of identifying the status of the sterilization process. For example, one or more of the LEDs may be programmed or otherwise controlled to project a blue color, such as a 405 nm LED, when the sterilization process in activated and ongoing and green when the sterilization process is complete.

FIG. 72 illustrates a perspective view of a UVC disinfection bar 5700 utilizing a pair of UVC lamps 5702, a cooling fan 5704 and a pair of sensors 5706. The pair of UVC lamps 5702 are positioned within the housing of the UVC disinfection bar 5700. Although two UVC lamps are shown, one or more UVC lamps may be utilized in the UVC disinfection bar 5700. Openings 5708, which may be covered with a transparent article such a quartz or others previously described or uncovered, allowing UVC light from the pair of UVC lamps 5702 to contact a portion of the electronic gaming machine. Those familiar with the art will recognize that any of the embodiments described herein may utilize such covers for a number of reasons including UVC lighting means protection and other.

Figure 73:
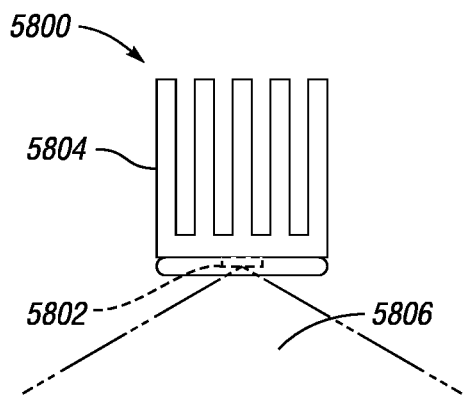
FIG. 73 illustrates a schematic end view of a UVC disinfection bar according to the embodiments of the present invention further illustrating the UVC light dispersion paths utilizing UVC LEDs mounted to a heat sink.
Figure 74:
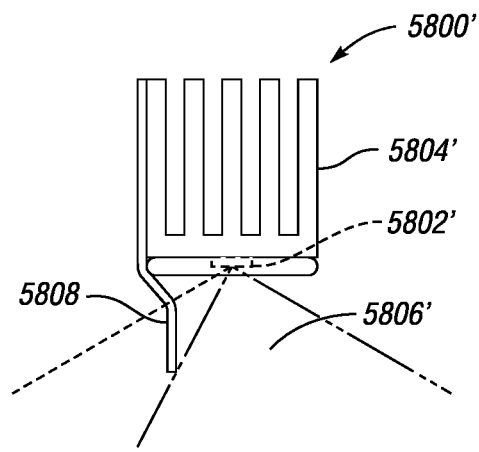
FIG. 74 illustrates a schematic end view of a UVC disinfection bar according to the embodiments of the present invention further illustrating the UVC light dispersion paths utilizing UVC LEDs mounted to a heat sink after a UVC light restriction baffle has been attached.

FIGS. 73-80 illustrate various views of UVC disinfection bars according to different embodiments of the present invention. FIG. 73 illustrates a schematic end view of a UVC disinfection bar 5800 comprising UVC LEDs 5802 mounted to a heat sink 5804. The heat sink 5804 carries away at least some of the heat created by the UVC LEDs 5802 mounted thereto to maintain a reasonable operating temperature range rather than allowing the heat to flow onto the electronic gaming device (or other device to which it is connected) or overheating the UVC disinfecting bar 5800, associated UVC LEDs, controllers, PCBs, or other components. UVC light dispersion 5806 is spread wide (approximately 105°) as no deflector or baffle is used. FIG. 74 illustrates a schematic end view of a UVC disinfection bar 5800' comprising UVC LEDs 5802' mounted to a heat sink 5804'. In this instance, a baffle 5808 serves to reduce or restrict the UVC light dispersion 5806' on one side of the UVC disinfection bar 5800'. Other embodiments include utilizing narrow viewing angle UVC LEDs, lenses or laser UVC LEDs to more precisely target areas to be disinfected while offering at least some protection for adjacent machines, players or staff by limiting UVC illumination to surrounding areas.

Figure 75:
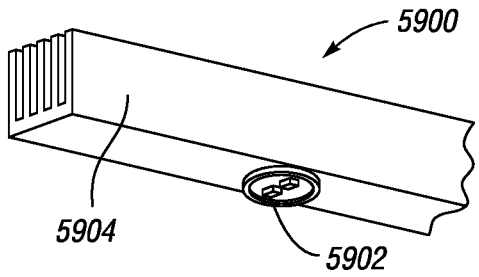
FIG. 75 illustrates a perspective view of a UVC disinfection bar according to the embodiments of the present invention with UVC LED modules mounted to a heat sink.
Figure 76:
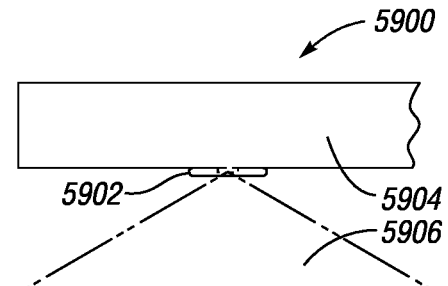
FIG. 76 illustrates a partial side elevation view of a UVC disinfection bar according to the embodiments of the present invention with UVC LED modules mounted to a heat sink further illustrating the UVC light dispersion paths utilizing UVC LEDs mounted to a heat.
Figure 77:
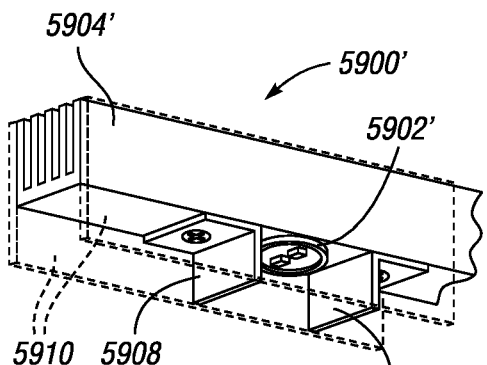
FIG. 77 illustrates a perspective view of a UVC disinfection bar according to the embodiments of the present invention with UVC LED modules mounted to a heat sink including left, right, front, and back UVC light baffles.
Figure 78:
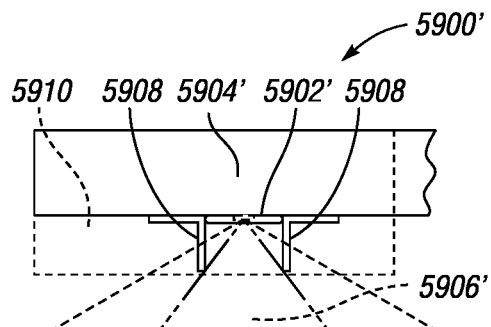
FIG. 78 illustrates a partial side elevation view of a UVC disinfection bar according to the embodiments the present invention with UVC LED modules mounted to a heat sink including left, right, front, and back UVC light baffles further illustrating the UVC light path restrictions.
Figure 79:
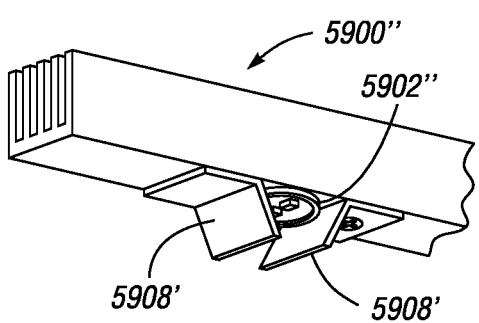
FIG. 79 illustrates a perspective view of a UVC disinfection bar according to the embodiments of the present invention with UVC LED modules mounted to a heat sink including left and right UVC light baffles.
Figure 80:
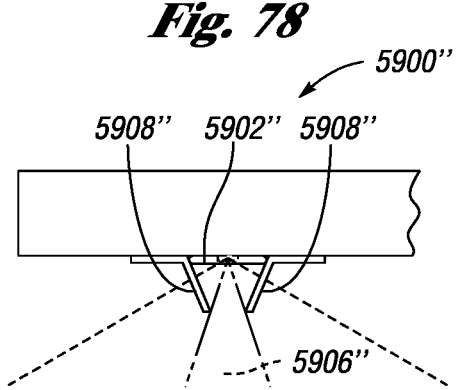
FIG. 80 illustrates a partial side elevation view of a UVC disinfection bar according to the embodiments of the present invention with UVC LED modules mounted to a heat sink including left and right UVC light baffles further illustrating the UVC light path restrictions.

FIG. 75 illustrates a schematic end view of a UVC disinfection bar 5900 comprising UVC LED modules 5902 mounted to a heat sink 5904. The heat sink 5904 carries away at least some of the heat created by the UVC LED modules 5902 mounted thereto to maintain a reasonable operating temperature range rather than allowing the heat to flow onto the electronic gaming device (or other device to which it is connected) or overheating the UVC disinfecting bar 5900, associated UVC LEDs, PCBs or other components. As shown in FIG. 76, UVC light dispersion 5906 is spread wide (approximately 105°) as no deflector or baffle is used. FIG. 77 illustrates a perspective view of UVC disinfection bar 5900' including orthogonal baffles 5908 on both sides of the UVC LED module 5902' mounted to a heat sink 5904'. In this instance, the baffles 5908 serve to reduce or restrict the UVC light dispersion 5906' along a length of the UVC disinfection bar 5900' as best seen in FIG. 78. FIG. 77 also illustrates other baffles 5910 (shown in broken lines) that may extend the length of the UVC disinfection bar 5900' thereby reducing the UVC light dispersion in the direction of players. FIG. 79 illustrates a perspective view of UVC disinfection bar 5900" including angled baffles 5908' on both sides of the UVC LED module 5902" mounted to a heat sink 5904". In this instance, the baffles 5908' serve to reduce or restrict the UVC light dispersion 5906" along a length of the UVC disinfection bar 5900" as best seen in FIG. 80. While not shown, UVC disinfection bar 5900" may also incorporate baffles, like those shown in FIG. 77, along its length. Those familiar with the art will recognize that baffles or similar structures, tubes, structural shapes, etc., may generally limit or direct the UVC to specific target areas in any embodiments of the present invention, described herein, providing enhanced performance and/or increased safety for players, staff or other humans. While at least the majority UVC radiation of some embodiments of the present invents are generally contained within the device where possible, UVC radiation emitted from other embodiments of the present invention cannot be entirely self-contained whereas focusing or directing of the UVC radiation provides the benefits of disinfection while limiting exposure to players, staff or other humans.

FIGS. 81-84 illustrate various views of UVC disinfection bars used with keypads according to embodiments of the present invention. FIG. 81 illustrates a partial front elevation view of a UVC disinfection bar 6000 attached above a keypad 6002 and FIG. 82 illustrates a side view of the same. Referencing FIG. 82, UVC disinfection bar 6000 includes a housing 6005, a UVC light source 6004 and deflector 6006 both angled inward to direct the light toward the keypad 6002. FIG. 83 illustrates a partial front elevation view of a UVC disinfection bar 6100 attached above a keypad 6102 and FIG. 84 illustrates a side view of the same. Referencing FIG. 84, UVC disinfection bar 6100 includes a UVC light source 6104 and deflector 6106 both angled inward to direct the light toward the keypad 6102. A spacer 6108 acts to move the UVC light source 6104 farther out away from the keypad 6102 improving the angle at which the UVC light may be directed towards the keypad 6102. In one embodiment, a spacer may be used to increase the angle by about 3°-10° or more depending on its thickness.

FIGS. 85-87 illustrate various views of UVC disinfection bars used with touch screen displays according to embodiments of the present invention. FIG. 85 illustrates a partial front elevation view of a UVC disinfection bar 6200 attached above a touch screen display 6202 and FIG. 86 illustrates a side view of the same. FIG. 87 illustrates the UVC disinfection bar 6200' attached above the touch screen display 6202' with the inclusion of a spacer 6206 to improve the angle at which the UVC light may be directed towards the touch screen display 6202'.

Figure 88:
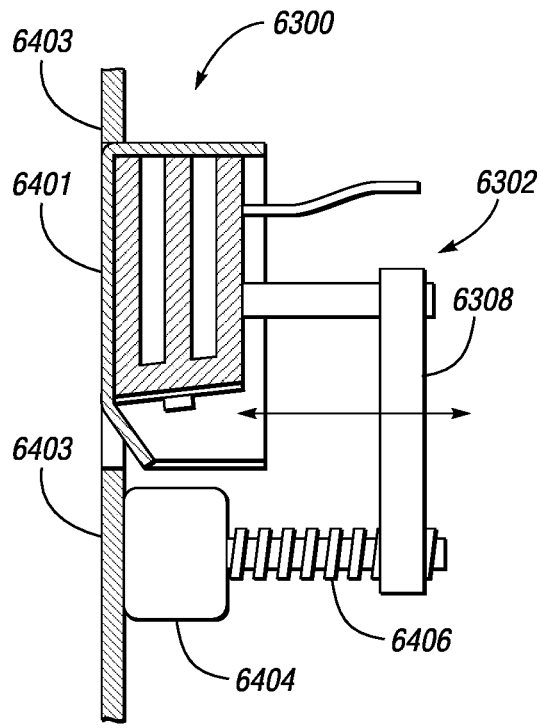
FIG. 88 illustrates a partial side cross section view of a UVC disinfection bar according to the embodiments of the present invention including a retracting mechanism further illustrating the UVC disinfection bar in the retracted position.
Figure 89:
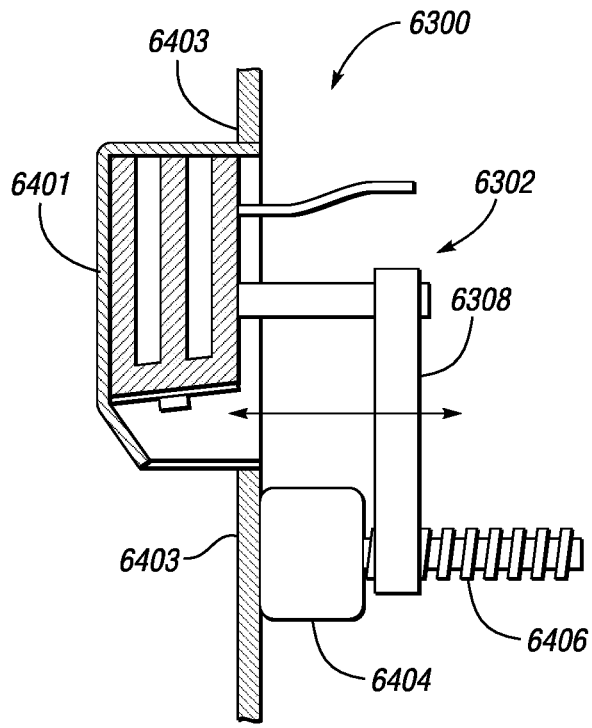
FIG. 89 illustrates a partial side cross section view of a UVC disinfection bar according to the embodiments of the present invention including a retracting mechanism further illustrating the UVC disinfection bar in the extended position.

FIGS. 88-91 illustrate various views of UVC disinfection bars including a retracting mechanism. FIG. 88 illustrates a partial side cross section view of a UVC disinfection bar 6300 in a retracted position and FIG. 89 illustrates the UVC disinfection bar 6300 in an extended position. The retracting mechanism 6302 includes a motor 6304, threaded rod 6306 and connector member 6308 joining the UVC disinfection bar 6300 to the threaded rod 6306. As motor 6304 drives the threaded rod 6306, connector member 6308 moves along the threaded rod 6306 causing the UVC disinfection bar 6300 to follow. When rotating in a first direction, the connector member 6308 moves along the threaded rod 6306 causing the UVC disinfection bar 6300 to move into a retracted position and when rotating in a second, opposite direction, the connector member 6308 moves along the threaded rod 6306 causing the UVC disinfection bar 6300 to move into an extended position. In the extended position, the UVC disinfection bar 6300 is available to sterilize a keypad, touch screen display or other article positioned there below. In the retracted position, an outer surface 6301 of the housing of the UVC disinfection bar 6300 remains flush with the surrounding surface providing an aesthetically pleasing installation.

Figure 90:
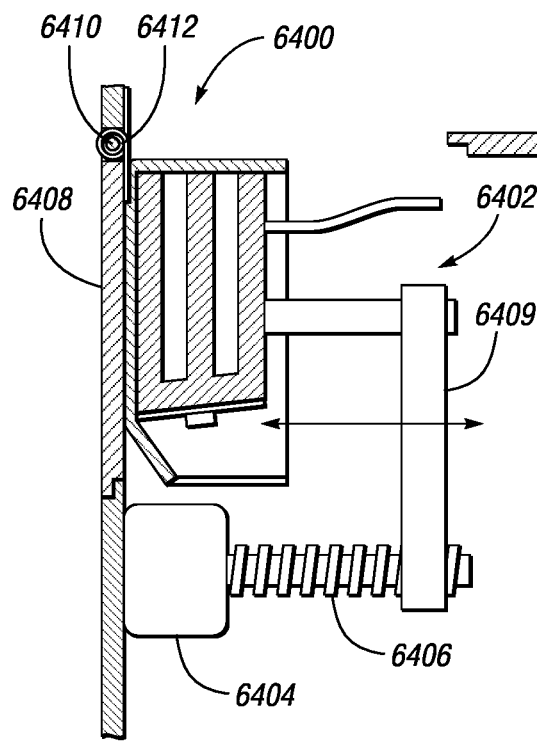
FIG. 90 illustrates a partial side cross section view of another UVC disinfection bar according to the embodiments of the present invention including a retracting mechanism further illustrating the UVC disinfection bar in the retracted position.
Figure 91:
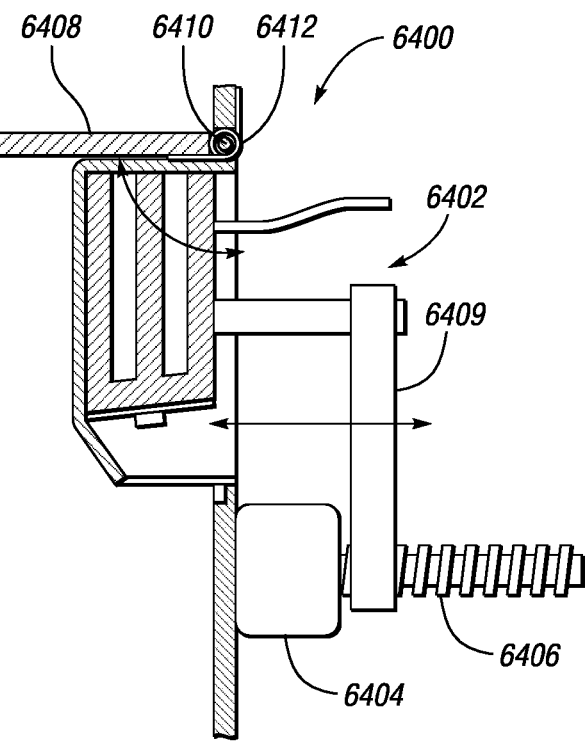
FIG. 91 illustrates a partial side cross section view of a another UVC disinfection bar according to the embodiments of the present invention including a retracting mechanism further illustrating the UVC disinfection bar in the extended position.

FIG. 90 illustrates a partial side cross section view of a UVC disinfection bar 6400 in a refracted position and FIG. 91 illustrates the UVC disinfection bar 6400 in an extended position. In this embodiment, retracting mechanism 6402, like above, includes a motor 6404, threaded rod 6406 and connector member 6409 joining the UVC disinfection bar 6400 to the threaded rod 6406. Retracting mechanism 6402 also operates like, as described above, retracting mechanism 6302. In this embodiment, a torsion spring biased hinged door 6408 conceals the UVC disinfection bar 6400 while in a refracted position. Door 6408 opens about the hinge 6410 allowing the UVC disinfection bar 6400 to move into an extended position as shown in FIG. 91. Those skilled in the art will recognize that the term UVC disinfecting bar does not necessarily denote any particular bar length, number of UVC LEDs, number of fans (if any), number of sensors (if any), etc., or even if heat sinks are desired or required. In some cases, a UVC disinfecting bar may only be long enough to contain a single UVC LED or may be long enough to contain multiple UVC LEDs while in other instances, smaller UVC disinfecting bars may be linked together to form a longer UVC disinfecting bar such as those daisy chained together.

Although the invention has been described in detail with reference to several embodiments, additional variations and modifications exist within the scope and spirit of the invention as described and defined in the following claims.

We claim:

1. A system for sterilizing portions of an electronic machine having a user interface, comprising:
   a bar member configured to mount to said electronic machine having a user interface, said bar member containing one or more UVC light sources, said one or more UVC light sources positioned to emit UVC light onto said user interface while at least partially limiting UVC light emissions to adjacent areas or structures;
   one or more fans contained within the bar member, said one or more fans forcing heat away from the UVC light sources and/or bar members;
   one or more sensors configured to detect the presence of one or more person(s) proximate said electronic machine;
   a controller configured to activate said one or more UVC light sources responsive to one or more outputs of said one or more sensors indicating that no persons are proximate said electronic machine and deactivate said one or more UVC light sources responsive to one or more outputs of said one or more sensors indicating that person(s) are proximate said electronic machine; and
   wherein the effectiveness of the sterilization by the UVC light increases with time of exposure and/or the intensity of the UVC light.

2. The system of claim 1 wherein the electronic machine is an electronic gaming machine, automated teller machine, kiosk, keypad, POS terminal, cash register or touch screen display.

3. The system of claim 1 further comprising one or more baffles or deflectors integral with or proximate to said bar member to more precisely direct the emitted UVC light.

4. The system of claim 1 wherein said bar member is further configured to mount above the user interface and emit UVC light downward on to the user interface.

5. The system of claim 1 further comprising one or more spacers contained within the bar member, said one or more spacers increasing the angle at which the UVC light is emitted on to the user interface.

6. The system of claim 1 wherein the one or more UVC light sources are UVC LED modules, individual UVC LEDs or UVC lamps.

7. The system of claim 1 wherein the at least a portion of the bar member is joined to or proximate to a heat sink, said heat sink configured to transfer heat from the UVC light source and/or bar member.

8. The system of claim 1 wherein the one or more sensors are motion sensors and/or proximity sensors.

9. The system of claim 1 wherein the UVC light sources produce far-UVC lighting with a wavelength between 207 nm and 222 nm.

10. The system of claim 1 wherein the controller is configured to deactivate said one or more UVC light sources after a predetermined period of time.

11. The system of claim 1 wherein the controller is configured to activate said one or more UVC light sources responsive to one or more outputs of said one or more sensors indicating that a person proximate to the electronic machine is no longer proximate to the electronic machine.

12. The system of claim 11 wherein the activation of said one or more UVC light sources is delayed for a predetermined period of time once a person is no longer proximate to the electronic machine.

13. An apparatus comprising:
   an electronic machine having a user interface;
   a bar member configured to mount to said electronic machine, said bar member containing one or more UVC light sources, said one or more UVC light sources positioned to emit UVC light onto said user interface while at least partially limiting UVC light emissions to adjacent areas or structures;
   one or more baffles or deflectors integral with said bar member to more precisely direct the emitted UVC light
   one or more sensors configured to detect the presence of one or more persons proximate said electronic machine;
   a controller configured to activate said one or more UVC light sources responsive to one or more outputs of said one or more sensors indicating that no person is proximate said electronic machine and deactivate said one or more UVC light sources responsive to one or more outputs of said one or more sensors indicating that no person is proximate said electronic machine; and
   wherein the effectiveness of the sterilization by the UVC light increases with time of exposure and/or the intensity of the UVC light.

14. The apparatus of claim 13 wherein the electronic machine is an electronic gaming machine, automated teller machine, kiosk, keypad, POS terminal, cash register or touch screen display.

15. The apparatus of claim 13 wherein said bar member is further configured to mount above the user interface and emit UVC light downward on to the user interface.

16. The apparatus of claim 13 further comprising one or more spacers contained within the bar member, said one or more spacers increasing the angle at which the UVC light is emitted on to the user interface.

17. The apparatus of claim 13 further comprising one or more fans contained within the bar member, said one or more fans forcing heat away from the bar member.

18. The apparatus of claim 13 wherein the one or more UVC light sources are UVC LED modules, individual UVC LEDs or UVC lamps.

19. The apparatus of claim 13 wherein at least a portion of the bar member is joined to or proximate to a heat sink, said heat sink configured to transfer heat from the bar member.

20. The apparatus of claim 13 wherein the one or more sensors are motion sensors and/or proximity sensors.

21. The apparatus of claim 13 wherein the UVC light sources produce far-UVC lighting with a wavelength between 207 nm and 222 nm.

22. The apparatus of claim 13 wherein the controller is configured to deactivate said one or more UVC light sources after a predetermined period of time.

23. The apparatus of claim 13 wherein the controller is configured to activate said one or more UVC light sources responsive to one or more outputs of said one or more sensors indicating that a person proximate to the electronic machine is no longer proximate to the electronic machine.

24. The apparatus of claim 21 wherein the activation of said one or more UVC light sources is delayed for a predetermined period of time once a person is no longer proximate to the electronic machine.

25. An electronic gaming machine comprising:
a user interface;
a bar member configured to mount to said electronic machine, said bar member containing one or more UVC light sources, said one or more UVC light sources positioned to emit UVC light onto said user interface while at least partially limiting UVC light emissions to adjacent areas or structures;
one or more baffles or deflectors integral with said bar member to more precisely direct the emitted UVC light
one or more sensors configured to detect the presence of one or more persons proximate said electronic gaming machine;
a controller configured to activate said one or more UVC light sources responsive to one or more outputs of said one or more sensors indicating that no person is proximate said electronic gaming machine and deactivate said one or more UVC light sources responsive to one or more outputs of said one or more sensors indicating that no person is proximate said electronic gaming machine; and
wherein the effectiveness of the sterilization by the UVC light increases with time of exposure and/or the intensity of the UVC light.

26. The electronic gaming machine of claim 25 wherein said bar member is further configured to mount above the user interface and emit UVC light downward on to the user interface.

27. The electronic gaming machine of claim 25 further comprising one or more spacers contained within the bar member, said one or more spacers increasing the angle at which the UVC light is emitted on to the user interface.

28. The electronic gaming machine of claim 25 further comprising one or more fans contained within the bar member, said one or more fans forcing heat away from the bar member.

29. The electronic gaming machine of claim 25 wherein the one or more UVC light sources are UVC LED modules, individual UVC LEDs or UVC lamps.

30. The electronic gaming machine of claim 25 wherein at least a portion of the bar member is joined to or proximate to a heat sink, said heat sink configured to transfer heat from the bar member.

31. The electronic gaming machine of claim 25 wherein the one or more sensors are motion sensors and/or proximity sensors.

32. The electronic gaming machine of claim 25 wherein the UVC light sources produce far-UVC lighting with a wavelength between 207 nm and 222 nm.

33. The electronic gaming machine of claim 25 wherein the controller is configured to deactivate said one or more UVC light sources after a predetermined period of time.

34. The system of claim 25 wherein the controller is configured to activate said one or more UVC light sources responsive to one or more outputs of said one or more sensors indicating that a person proximate to the electronic machine is no longer proximate to the electronic machine.

35. The system of claim 34 wherein the activation of said one or more UVC light sources is delayed for a predetermined period of time once a person is no longer proximate to the electronic machine.

36. A sterilizing apparatus comprising:
a bar member configured to mount to an electronic machine, said bar member containing one or more UVC light sources, said one or more UVC light sources positioned to emit UVC light onto at least a user interface of the electronic machine while at least partially limiting UVC light emissions to adjacent areas or structures;
one or more baffles positioned proximate to said one or more UVC light sources to direct the UVC light to a desired portion of the electronic machine;
one or more sensors configured to detect the presence of one or more persons proximate said electronic machine, said one or more sensors integral with said bar member;
a controller configured to activate said one or more UVC light sources responsive to one or more outputs of said one or more sensors indicating that no person is proximate said electronic machine and deactivate said one or more UVC light sources responsive to one or more outputs of said one or more sensors indicating that no person is proximate said electronic machine, said controller integral with said bar member.

37. The sterilizing apparatus of claim 36 wherein the electronic machine is an electronic gaming machine, automated teller machine, kiosk, keypad, POS terminal, cash register or touch screen display.

38. The sterilizing apparatus of claim 36 wherein said bar member is further configured to mount above the user interface and emit UVC light downward on to the user interface.

39. The sterilizing apparatus of claim 36 further comprising one or more spacers contained within the bar member, said one or more spacers increasing the angle at which the UVC light is emitted on to the user interface.

40. The sterilizing apparatus of claim 36 further comprising one or more fans contained within the bar member, said one or more fans forcing heat away from the bar member.

41. The sterilizing apparatus of claim 36 wherein the one or more UVC light sources are UVC LED modules, individual UVC LEDs or UVC lamps.

42. The sterilizing apparatus of claim 36 wherein at least a portion of the bar member is joined to or proximate to a heat sink, said heat sink configured to transfer heat from the bar member.

43. The sterilizing apparatus of claim 36 wherein the one or more sensors are motion sensors and/or proximity sensors.

44. The sterilizing apparatus of claim 36 wherein the UVC light sources produce far-UVC lighting with a wavelength between 207 nm and 222 nm.

45. The sterilizing apparatus of claim 36 wherein the controller is configured to deactivate said one or more UVC light sources after a predetermined period of time.

46. The sterilizing apparatus of claim 36 wherein the controller is configured to activate said one or more UVC light sources responsive to one or more outputs of said one or more sensors indicating that a person proximate to the electronic machine is no longer proximate to the electronic machine.

47. The sterilizing apparatus of claim 46 wherein the activation of said one or more UVC light sources is delayed for a predetermined period of time once a person is no longer proximate to the electronic machine.

48. An electronic gaming machine comprising:
a user interface;
one or more bar members mounted to said electronic machine, said one or bar members containing one or more UVC light sources, said one or more bar members including baffles positioned to direct the UVC light while at least partially limiting UVC light emissions to adjacent areas or structures;
one or more sensors configured to detect the presence of one or more persons proximate said electronic gaming machine; and
wherein said one or more UVC light sources are configured to activate responsive to one or more outputs of said one or more sensors indicating that no person is proximate said electronic gaming machine and deactivate responsive to one or more outputs of said one or more sensors indicating that no person is proximate said electronic gaming machine.

49. The gaming machine of claim 48 wherein one or more bar members are positioned proximate to one or more of said user interface, a first display and a second display.

50. The gaming machine of claim 48 wherein a bar member is positioned behind a lower portion of a primary display, beneath a lower portion of the primary display or on a front lower portion of the primary display.

51. The gaming machine of claim 48 wherein the one or more bar members contain a number of UVC light sources to cover a width of the electronic gaming machine.

52. The gaming machine of claim 51 wherein the one or more bar members contain three or more UVC light sources to cover a width of the electronic gaming machine.

53. The gaming machine of claim 48 wherein the one or more bar members include a frontal lip to block UVC light.

54. The gaming machine of claim 48 wherein the one or more UVC light sources are UVC LED modules, individual UVC LEDs or UVC lamps.

55. The gaming machine of claim 48 wherein the one or more UVC light sources are individual UVC LEDs.

56. The gaming machine of claim 55 wherein one or more of said UVC light sources are configured to illuminate to indicate a status of sterilization associated with said UVC light sources.

57. The gaming machine of claim 48 further comprising a controller to activate and deactivate said UVC light sources.

58. The gaming machine of claim 48 wherein the UVC light sources produce far-UVC lighting with a wavelength between 207 nm and 222 nm.

59. The gaming machine of claim 48 wherein the controller is configured to deactivate said one or more UVC light sources after a predetermined period of time.

60. The system of claim 48 wherein the controller is configured to activate said one or more UVC light sources responsive to one or more outputs of said one or more sensors indicating that a person proximate to the electronic machine is no longer proximate to the electronic machine.

61. The system of claim 60 wherein the activation of said one or more UVC light sources is delayed for a predetermined period of time once a person is no longer proximate to the electronic machine.

62. An automatic UVC sterilization apparatus of comprising:
a bar member containing one or more UVC light sources, said one or more UVC light sources positioned to emit UVC light onto a sterilization target while at least partially limiting UVC light emissions to adjacent areas or structures by the use of baffles or deflectors;
one or more spacers contained within the bar member, said one or more spacers increasing the angle at which the UVC light is emitted on to the sterilization target
one or more sensors configured to detect the presence of one or more persons proximate said automatic UVC sterilization apparatus;
a controller configured to activate said one or more UVC light sources responsive to one or more outputs of said one or more sensors indicating that no person is proximate said electronic machine and deactivate said one or more UVC light sources responsive to one or more outputs of said one or more sensors indicating that no person is proximate said UVC disinfection apparatus; and
wherein the effectiveness of the sterilization by the UVC light increases with time of exposure and/or the intensity of the UVC light.

63. The automatic UVC sterilization apparatus of claim 62 wherein said bar member is further configured to mount above the sterilization target and emit UVC light downward on to the sterilization target.

64. The automatic UVC sterilization apparatus of claim 62 further comprising one or more fans contained within the bar member, said one or more fans forcing heat away from the bar member.

65. The automatic UVC sterilization apparatus of claim 62 wherein the one or more UVC light sources are UVC LED modules, individual UVC LEDs or UVC lamps.

66. The automatic UVC sterilization apparatus of claim 62 wherein at least a portion of the bar member is joined to or proximate to a heat sink, said heat sink configured to transfer heat from the bar member.

67. The automatic UVC sterilization apparatus of claim 62 wherein the one or more sensors are motion sensors and/or proximity sensors.

68. The automatic UVC sterilization apparatus of claim 62 wherein the UVC light sources produce far-UVC lighting with a wavelength between 207 nm and 222 nm.

69. The automatic UVC sterilization apparatus of claim 62 wherein the controller is configured to deactivate said one or more UVC light sources after a predetermined period of time.

70. The automatic UVC sterilization apparatus of claim 62 wherein the controller is configured to activate said one or more UVC light sources responsive to one or more outputs of said one or more sensors indicating that a person proximate to the electronic machine is no longer proximate to the electronic machine.

71. The automatic UVC sterilization apparatus of claim 70 wherein the activation of said one or more UVC light sources is delayed for a predetermined period of time once a person is no longer proximate to the electronic machine.

72. The system of claim 62 wherein the baffles or deflectors are constructed of non-reflective UVC materials.

73. The system of claim 62 wherein the baffles or deflectors are constructed of reflective UVC materials.

74. An automatic system for sterilizing a sterilization target, comprising:
- a bar member configured to mount to said sterilization target, said bar member containing one or more UVC light sources, said one or more UVC light sources positioned to emit UVC light onto said sterilization target while at least partially limiting UVC light emissions to adjacent areas or structures by the use of baffles or deflectors, wherein the at least a portion of the bar member is joined to or proximate to a heat sink, said heat sink configured to transfer heat from the UVC light source and/or bar members;
- one or more sensors configured to detect the presence of one or more person(s) proximate said sterilization target;
- a controller configured to activate said one or more UVC light sources responsive to one or more outputs of said one or more sensors indicating that no persons are proximate said sterilization target and deactivate said one or more UVC light sources responsive to one or more outputs of said one or more sensors indicating that person(s) are proximate said sterilization target; and wherein the effectiveness of the sterilization by the UVC light increases with time of exposure and/or the intensity of the UVC light.

75. The system of claim 74 wherein said bar member is further configured to mount above the sterilization target and emit UVC light downward on to the sterilization target.

76. The system of claim 74 further comprising one or more spacers contained within the bar member, said one or more spacers increasing the angle at which the UVC light is emitted on to the sterilization target.

77. The system of claim 74 further comprising one or more fans contained within the bar member, said one or more fans forcing heat away from the UVC light sources and/or bar member.

78. The system of claim 74 wherein the one or more UVC light sources are UVC LED modules, individual UVC LEDs or UVC lamps.

79. The system of claim 74 wherein the one or more sensors are motion sensors and/or proximity sensors.

80. The system of claim 74 wherein the UVC light sources produce far-UVC lighting with a wavelength between 207 nm and 222 nm.

81. The system of claim 74 wherein the controller is configured to deactivate said one or more UVC light sources after a predetermined period of time.

82. The system of claim 74 wherein the controller is configured to activate said one or more UVC light sources responsive to one or more outputs of said one or more sensors indicating that a person proximate to the electronic machine is no longer proximate to the electronic machine.

83. The system of claim 82 wherein the activation of said one or more UVC light sources is delayed for a predetermined period of time once a person is no longer proximate to the electronic machine.

84. The system of claim 74 wherein the baffles or deflectors are constructed of non-reflective UVC materials.

85. The system of claim 74 wherein the baffles or deflectors are constructed of reflective UVC materials.

\* \* \* \* \*